(12) United States Patent
White et al.

(10) Patent No.: US 12,269,892 B2
(45) Date of Patent: Apr. 8, 2025

(54) ANTI-GLYCO-MUC1 ANTIBODIES AND THEIR USES

(71) Applicant: GO Therapeutics, Inc., Cambridge, MA (US)

(72) Inventors: Thayer White, Boxford, MA (US); Hans H. Wandall, Charlottenlund (DK)

(73) Assignee: GO Therapeutics, Inc., Cambridge, MA (US)

( * ) Notice: Subject to any disclaimer, the term of this patent is extended or adjusted under 35 U.S.C. 154(b) by 1107 days.

(21) Appl. No.: 17/256,326

(22) PCT Filed: Jun. 28, 2019

(86) PCT No.: PCT/US2019/039883
§ 371 (c)(1),
(2) Date: Dec. 28, 2020

(87) PCT Pub. No.: WO2020/006449
PCT Pub. Date: Jan. 2, 2020

(65) Prior Publication Data
US 2021/0269552 A1    Sep. 2, 2021

Related U.S. Application Data

(60) Provisional application No. 62/802,865, filed on Feb. 8, 2019, provisional application No. 62/691,887, filed on Jun. 29, 2018.

(51) Int. Cl.
*C07K 16/30* (2006.01)
*G01N 33/574* (2006.01)

(52) U.S. Cl.
CPC ... *C07K 16/3092* (2013.01); *G01N 33/57488* (2013.01); *C07K 2317/31* (2013.01); *C07K 2317/34* (2013.01); *C07K 2317/35* (2013.01); *C07K 2317/565* (2013.01); *C07K 2317/622* (2013.01); *C07K 2317/92* (2013.01)

(58) Field of Classification Search
CPC ............ C07K 16/3092; C07K 2317/34; C07K 2317/565; C07K 2317/31
See application file for complete search history.

(56) References Cited

U.S. PATENT DOCUMENTS

| | | | |
|---|---|---|---|
| 8,440,798 B2 | 5/2013 | Clausen et al. |
| 8,722,856 B2 | 5/2014 | Nishimura et al. |
| 8,883,977 B2 | 11/2014 | Nishimura et al. |
| 8,912,311 B2 | 12/2014 | Clausen et al. |
| 9,359,436 B2 | 6/2016 | Clausen et al. |
| 9,588,121 B2 | 3/2017 | Wandall et al. |
| 2002/0132771 A1 | 9/2002 | Madiyalakan |
| 2002/0146750 A1 | 10/2002 | Hoogenboom et al. |
| 2003/0186850 A1 | 10/2003 | Clausen et al. |
| 2007/0044171 A1 | 2/2007 | Kovalic et al. |
| 2009/0162359 A1 | 6/2009 | Klein et al. |
| 2010/0034825 A1 | 2/2010 | Clausen et al. |
| 2010/0278818 A1 | 11/2010 | Hubert-Haddad et al. |
| 2010/0322935 A1 | 12/2010 | Croasdale et al. |
| 2011/0172392 A1 | 7/2011 | Kajihara et al. |
| 2012/0040375 A1 | 2/2012 | Nishimura et al. |
| 2012/0128676 A1 | 5/2012 | Goletz et al. |
| 2012/0276104 A1 | 11/2012 | Woisetschlager |
| 2013/0045490 A1 | 2/2013 | Yonezawa |
| 2013/0045543 A1 | 2/2013 | Nishimura et al. |
| 2013/0337505 A1 | 12/2013 | Mekada et al. |
| 2015/0005474 A1 | 1/2015 | Goletz et al. |
| 2015/0166670 A1 | 6/2015 | Castoldi et al. |
| 2016/0145343 A1 | 5/2016 | Schoen et al. |
| 2016/0176980 A1 | 6/2016 | Chang et al. |
| 2017/0129962 A1 | 5/2017 | Regula et al. |
| 2017/0145116 A1 | 5/2017 | Regula et al. |
| 2020/0131275 A1 | 4/2020 | Goletz et al. |

FOREIGN PATENT DOCUMENTS

| | | |
|---|---|---|
| CN | 106661110 A | 5/2017 |
| EP | 2351777 B1 | 10/2015 |
| WO | WO1989008711 | 9/1989 |
| WO | WO2008040362 | 4/2008 |
| WO | WO2008119353 | 10/2008 |
| WO | WO2011012309 | 2/2011 |
| WO | WO2014051433 | 4/2014 |
| WO | WO2015120180 | 8/2015 |

OTHER PUBLICATIONS

Qu, Jin, et al. "Molecular basis of antibody binding to mucin glycopeptides in lung cancer." International journal of oncology 48.2 (2016): 587-594.

Almagro & Fransson, Frontiers in Bioscience 2008; 13:1619-33 (Year: 2008).

Beatson et al., 2015, "The Breast Cancer-Associated Glycoforms of MUC1, MUC1-Tn and sialyl-Tn, Are Expressed in COSMC Wild-Type Cells and Bind the C-Type Lectin MGL," PLoS ONE, 10(5): e0125994.

Bennett et al., 1998, "Cloning of a Human UDP-N-Acetyl-a-Galactosamine: Polypeptide N-Acetylgalactosaminyltransferase That Complements Other GalNAc-Transferases in Complete O-Glycosylation of the MUC1 Tandem Repeat," The Journal of Biological Chemistry, 273(46):30472-30481.

Brokx et al., 2003, "Nuclear Magnetic Resonance-Based Dissection of Glycosyltransferase Specificity for the Mucin MUC1 Tandem Repeat," Biochemistry, 42(47):13817-13825.

CROSSMAB (Trademark Electronic Search System, downloaded Mar. 23, 2021) (Year: 2021).

(Continued)

*Primary Examiner* — Gyan Chandra
(74) *Attorney, Agent, or Firm* — Biospark Intellectual Property Law

(57) ABSTRACT

The present disclosure relates to anti-glyco-MUC1 antibodies and antigen binding fragments thereof that specifically bind to a cancer-specific glycosylation variant of MUC1 and related fusion proteins and antibody-drug conjugates, as well as nucleic acids encoding such biomolecules. The present disclosure further relates to use of the antibodies, antigen-binding fragments, fusion proteins, antibody-drug conjugates and nucleic acids for cancer therapy.

22 Claims, 15 Drawing Sheets

Figure 1A:
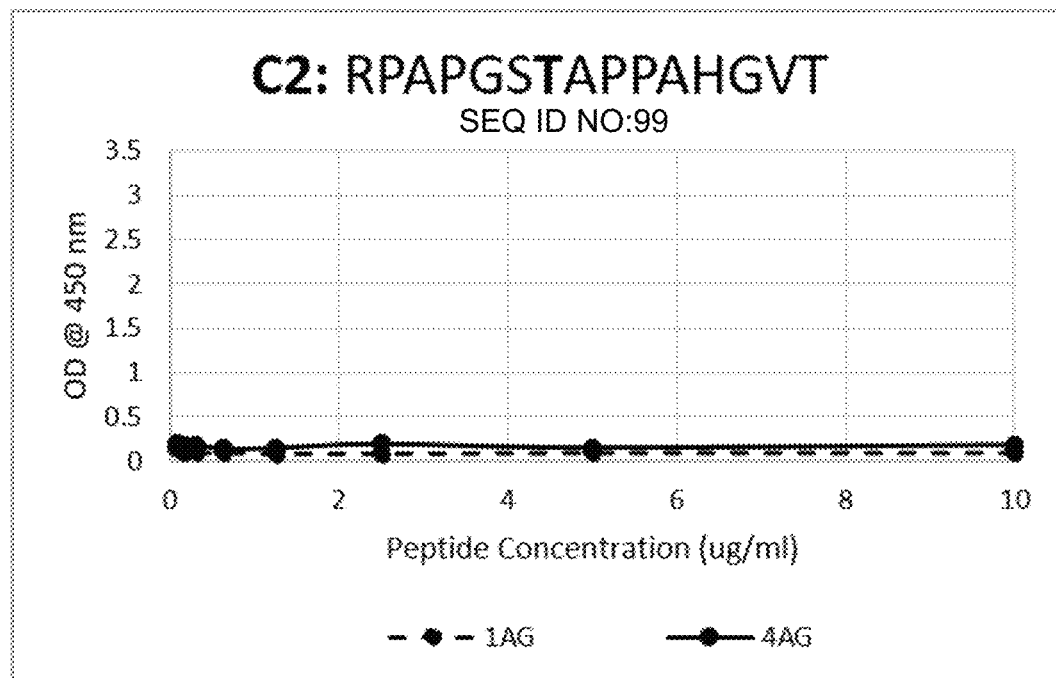

Specification includes a Sequence Listing.

(56) References Cited

OTHER PUBLICATIONS

Dalziel et al., 2001, "The Relative Activities of the C2GnT1 and ST3Gal-I Glycosyltransferases Determine O-Glycan Structure and Expression of an Tumor-associated Epitope on MUC1," The Journal of Biological Chemistry, 276(14):11007-11015.

de Bono et al., 2004, "Phase I trial of a murine antibody to MUC1 in patients with metastatic cancer: evidence for the activation of humoral and cellular antitumor immunity," Annals of Oncology, 15:1825-1833.

Dualogics, "The OrthoMab platform—How it works," downloaded from https://www.dualogics.com/technology/ on Oct. 9, 2017.

Extended European Search Report issued Apr. 19, 2021 in connection with 17929557.1.

Extended European Search Report issued Feb. 28, 2022 in connection with application No. 19826976.3.

Fontenot et al. 1993 "Synthesis of large multideterminant peptide immunogens using a poly-proline beta-turn helix motif" Database Biosis, Biosciences Information Service, XP55796187, Database accession No. PREV199497079884.

Fritz et al., 2004, "The beginnings of mucin biosynthesis: The crystal structure of UDP-GalNAc:polypeptide α-N-acetylgalactosaminyltransferase-T1," PNAS, 101(43):15307-15312.

International Search Report and Written Opinion for PCT/US2017/0058036, mailed Mar. 29, 2018.

International Search Report and Written Opinion for PCT/US2019/039883, mailed Oct. 22, 2019.

Irimura et al., 1999, "Diverse Glycosylation of MUC1 and MUC2: Potential Significance in Tumor Immunity," J. Biochem., 126:975985.

Kagan et al., 2004, "Comparison of antigen constructs and carrier molecules for augmenting the immunogenicity of the monosaccharide epithelial cancer antigen Tn," Cancer Immunol Immunother, 54:424-430, DOI 10.1007/s00262-004-0584-y.

Katayose et al., 1996, "MUC1-specific Targeting Immunotherapy with Bispecific Antibodies: Inhibition of Xenografted Human Bile Duct Carcinoma Growth," Cancer Research, 56:4205-4212.

Kirnarsky et al., 2002, "Structural analysis of peptide substrates for O-glycosylation," pp. 713-714.

Kjeldsen et al., 1988, "Human-Human Hybridomas and Human Monoclonal Antibodies Obtained by Fusion of Lymph Node Lymphocytes from Breast Cancer Patients," Cancer Research, 48:3208-3214.

Kjeldsen et al., 1988, "Preparation and Characterization of Monoclonal Antibodies Directed to the Tumor-associated O-linked Sialosyl-2→6 α-N-Acetylgalactosaminyl (Sialosyl-Tn) Epitope," Cancer Research, 48:2214-2220.

Klein et al., 2016, "The use of CrossMAb technology for the generation of bi- and multispecific antibodies," mAbs, 8(6):1010-1020, DOI: 10.1080/19420862.2016.1197457.

Labrijn et al., 2013, "Efficient generation of stable bispecific IgG1 by controlled Fab-arm exchange," PNAS, 110(13):5145-5150.

Liu et al., 2017, "Fc Engineering for Developing Therapeutic Bispecific Antibodies and Novel Scaffolds," Frontiers in Immunology, 8(38):1-15, doi: 10.3389/fimmu.2017.00038.

Marcos et al., 2004, "Role of the Human ST6GAlNAc-I and ST6GalNAc-II in the Synthesis of the Cancer-Associated Sialyl-Tn Antigen," Cancer Research, 64:7050-7057.

Matsushita et al., 2014, "A straightforward protocol for the preparation of high performance microarray displaying synthetic MUC1 glycopeptides," Biochimica et Biophysica Acta, 1840:1105-1116.

Mensdorff-Pouilly et al., 2000, "Reactivity Of Natural And Induced Human Antibodies To MUC1 Mucin With MUC1 Peptides And N-Acetylgalactosamine (GalNAc) Peptides," Int. J. Cancer, 86:702-712.

Nishimori et al., 1994, "Influence of Acceptor Substrate Primary Amino Acid Sequence on the Activity of Human UDP-N-acetylgalactosamine:Polypeptide N-Acetylgalactosaminyltransferase," The Journal of Biological Chemistry, 269(23):16123-16130.

Posey et al., 2016, "Engineered CAR T Cells Targeting the Cancer-Associated Tn-Glycoform of the Membrane Mucin MUC1 Control Adenocarcinoma," Immunity, 44:1444-1454.

Reiersen et al. (Nucleic Acids Res. 2005 33(1): e10) (Year: 2005).

Škrlec et al., 2015, "Non-immunoglobulin scaffolds: a focus on their targets," Trends in Biotechnology, 33(7):408-418.

Song et al., 2012, "MUC1 glycopeptide epitopes predicted by computational glycomics," International Journal of Oncology, 41:1977-1984.

Sørensen et al., 2006, "Chemoenzymatically synthesized multimeric Tn/STn MUC1 glycopeptides elicit cancer-specific anti-MUC1 antibody responses and override tolerance," Glycobiology, 16(2):96-107.

Takeuchi et al., 2002, "The epitope recognized by the unique anti-MUC1 monoclonal antibody MY.1E12 involves sialylα2-3galactosylβ1-3N-acetylgalactosaminide linked to a distinct threonine residue in the MUC1 tandem repeat," Journal of Immunological Methods, 270:199-209.

Tarp et al., 2007, "Identification of a novel cancer-specific immunodominant glycopeptide epitope in the MUC1 tandem repeat," Glycobiology 17(2):197-209.

Taylor-Papadimitriou et al., 1999, "Review—MUC1 and cancer," Biochimica et Biophysica Acta, 1455:301-313.

Thie et al., 2011, "Rise and Fall of an Anti-MUC1 Specific Antibody," PLos ONE, 6(1):e15921.

Wandall et al., 2007, "The lectin domains of polypeptide GalNAc-transferases exhibit carbohydrate-binding specificity for GalNAc: lectin binding to GalNAc-glycopeptide substrates is required for high density GalNAc-O-glycosylation," Glycobiology 17(4):374-387.

Yang et al., 2017, "Bispecific Antibodies as a Development Platform for New Concepts and Treatment Strategies," Int. J. Mol. Sci., 18(48):1-21; doi: 10.3390/ijms18010048.

Zhou et al., 2018, "Epitopes of MUC1 Tandem Repeats in Cancer as Revealed by Antibody Crystallography: Toward Glycopeptide Signature-Guided Therapy" Molecules, 23, 1326.

Zhukovsky et al., 2016, "Bispecific antibodies and CARs: generalized immunotherapeutics harnessing T cell redirection," Current Opinion in Immunology, 40:24-35.

SEQUENCE LISTING

```
<160> NUMBER OF SEQ ID NOS: 118

<210> SEQ ID NO 1
<211> LENGTH: 118
<212> TYPE: PRT
<213> ORGANISM: Artificial Sequence
<220> FEATURE:
<223> OTHER INFORMATION: Synthetic peptide

<400> SEQUENCE: 1

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Asp
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Lys Asn Tyr Thr Pro Ser Leu
        50                  55                  60

Lys Asp Lys Phe Ile Ile Ser Arg Asp Asn Ala Lys Asn Thr Leu Phe
65                  70                  75                  80

Leu Gln Met Ser Ser Val Arg Ser Glu Asp Thr Ala Leu Tyr Tyr Cys
                85                  90                  95

Ala Thr Ser His Tyr Tyr Gly Leu Phe Gly Tyr Trp Gly Gln Gly Thr
            100                 105                 110

Leu Val Thr Val Ser Ala
        115

<210> SEQ ID NO 2
<211> LENGTH: 111
<212> TYPE: PRT
<213> ORGANISM: Artificial Sequence
<220> FEATURE:
<223> OTHER INFORMATION: Synthetic peptide

<400> SEQUENCE: 2

Asp Ile Val Leu Thr Gln Ser Pro Ala Ser Leu Thr Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Arg Thr Phe Gly Gly Gly Thr Lys Leu Glu Ile Lys
            100                 105                 110

<210> SEQ ID NO 3
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Gly Phe Asp Phe Ser Arg Asp Trp
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Ile Asn Pro Asp Ser Ser Thr Lys
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Ala Thr Ser His Tyr Tyr Gly Leu Phe Gly Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Lys Ser Val Ser Thr Ser Gly Tyr Ser Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide

<400> SEQUENCE: 7

Leu Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Gln His Ser Arg Glu Leu Pro Arg Thr
1               5

<210> SEQ ID NO 9
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 9

Arg Asp Trp Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Glu Ile Asn Pro Asp Ser Ser Thr Lys Asn Tyr Thr Pro Ser Leu Lys
1               5                   10                  15

Asp

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Ser His Tyr Tyr Gly Leu Phe Gly Tyr
1               5

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Arg Ala Ser Lys Ser Val Ser Thr Ser Gly Tyr Ser Tyr Met His
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Leu Ala Ser Tyr Leu Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Gln His Ser Arg Glu Leu Pro Arg Thr
1               5

<210> SEQ ID NO 15
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Gly Phe Asp Phe Ser Arg Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Asn Pro Asp Ser Ser Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Ser His Tyr Tyr Gly Leu Phe Gly Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Ser Lys Ser Val Ser Thr Ser Gly Tyr Ser Tyr
1               5                   10

<210> SEQ ID NO 19
<211> LENGTH: 3
<212> TYPE: PRT
<213> ORGANISM: Artificial Sequence
<220> FEATURE:
<223> OTHER INFORMATION: Synthetic peptide

<400> SEQUENCE: 19

Leu Ala Ser
1

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Ser Arg Glu Leu Pro Arg Thr
1               5

<210> SEQ ID NO 21
<211> LENGTH: 708
```

<210> SEQ ID NO 21
<211> LENGTH: 708
<212> TYPE: DNA
<213> ORGANISM: Artificial Sequence
<220> FEATURE:
<223> OTHER INFORMATION: Synthetic nucleotide sequence

<400> SEQUENCE: 21

```
gaggtgaagc ttctcgagtc tggaggtggc ctggtgcagc ctggaggatc cctgaaattg     60
tcctgtgcag cctcaggatt cgatttagt agagactgga tgagttgggt ccggcaggct    120
ccagggaaag gctagaatg gattggagag attaatccag atagcagtac gaaaaactac    180
acgccatctc taaaggataa attcatcatt ccagagaca cgccaaaaa tacgctgttc     240
ctgcaaatga gcagcgtgag atctgaggac acagcccttt attactgtgc aacctctcat     300
tactacggcc tgtttggtta ctggggccaa gggactctgg tcactgtctc tgcagaggtg    360
aagcttctcg agtctggagg tggcctggtg cagcctggag gatccctgaa attgtcctgt    420
gcagcctcag gattcgattt tagtagagac tggatgagtt gggtccggca ggctccaggg    480
aaagggctag aatggattgg agagattaat ccagatagca gtacgaaaaa ctacacgcca    540
tctctaaagg ataaattcat catttccaga gacaacgcca aaaatacgct gttcctgcaa    600
atgagcagcg tgagatctga ggacacagcc ctttattact gtgcaacctc tcattactac    660
ggcctgtttg gttactgggg ccaagggact ctggtcactg tctctgca                 708
```

<210> SEQ ID NO 22
<211> LENGTH: 333
<212> TYPE: DNA
<213> ORGANISM: Artificial Sequence
<220> FEATURE:
<223> OTHER INFORMATION: Synthetic nucleotide sequence

<400> SEQUENCE: 22

```
gacattgtgc tgacacagtc tcctgcttcc ttaactgtat ctctgggca gagggccacc     60
atctcatgca gggccagcaa aagtgtcagt acatctggct atagttatat gcactggtac    120
caacagaaac caggacagcc acccaaactc ctcatctatc ttgcttccta cctagaatct    180
ggggtccctg ccaggttcag tggcagtggg tctgggacag acttcaccct caacatccat    240
cctgtggagg aggaggatgc tgcaacctat tactgtcagc acagtaggga gcttcctcgg    300
acgttcggtg aggcaccaa gctggaaatc aaa                                 333
```

<210> SEQ ID NO 23
<211> LENGTH: 118
<212> TYPE: PRT
<213> ORGANISM: Artificial Sequence
<220> FEATURE:
<223> OTHER INFORMATION: Synthetic peptide

<400> SEQUENCE: 23

```
Glu Val Lys Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
            20                  25                  30

Trp Met Ser Trp Val Arg Gln Ala Pro Gly Lys Gly Pro Glu Trp Ile
        35                  40                  45

Gly Glu Ile Asn Pro Glu Ser Asn Thr Met Asn Tyr Ser Pro Ser Leu
    50                  55                  60

Lys Glu Lys Phe Ile Ile Ser Arg Asp Thr Ala Lys Asn Met Leu Tyr
65                  70                  75                  80

Leu Gln Met Ser Lys Val Arg Ser Glu Asp Thr Ala Leu Tyr Tyr Cys
```

```
                    85                  90                  95

Ala Thr Ser His His Tyr Gly Leu Phe Asp Tyr Trp Gly Gln Gly Thr
            100                 105                 110

Leu Val Thr Val Ser Ala
        115

<210> SEQ ID NO 24
<211> LENGTH: 111
<212> TYPE: PRT
<213> ORGANISM: Artificial Sequence
<220> FEATURE:
<223> OTHER INFORMATION: Synthetic peptide

<400> SEQUENCE: 24

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Asn Tyr Ile His Trp Tyr Gln Gln Lys Pro Gly Gln Pro Pro
        35                  40                  45

Lys Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Phe Cys Gln His Ser Arg
                85                  90                  95

Glu Leu Pro Arg Thr Phe Gly Gly Gly Thr Lys Leu Glu Phe Lys
            100                 105                 110

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Gly Phe Asp Phe Ser Arg Tyr Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Ile Asn Pro Glu Ser Asn Thr Met
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Ala Thr Ser His His Tyr Gly Leu Phe Asp Tyr
1               5                   10
```

```
<210> SEQ ID NO 28
<211> LENGTH: 10
<212> TYPE: PRT
<213> ORGANISM: Artificial Sequence
<220> FEATURE:
<223> OTHER INFORMATION: Synthetic peptide

<400> SEQUENCE: 28

Lys Ser Val Ser Thr Ser Gly Tyr Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Synthetic peptide

<400> SEQUENCE: 29

Leu Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Gln His Ser Arg Glu Leu Pro Arg Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Arg Tyr Trp Met Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic peptide

<400> SEQUENCE: 32

Glu Ile Asn Pro Glu Ser Asn Thr Met Asn Tyr Ser Pro Ser Leu Lys
1               5                   10                  15

Glu

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Ser His His Tyr Gly Leu Phe Asp Tyr
1               5
```

```
<210> SEQ ID NO 34
<211> LENGTH: 15
<212> TYPE: PRT
<213> ORGANISM: Artificial Sequence
<220> FEATURE:
<223> OTHER INFORMATION: Synthetic peptide

<400> SEQUENCE: 34

Arg Ala Ser Lys Ser Val Ser Thr Ser Gly Tyr Asn Tyr Ile His
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Leu Ala Ser Tyr Leu Glu Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Gln His Ser Arg Glu Leu Pro Arg Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Gly Phe Asp Phe Ser Arg Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Asn Pro Glu Ser Asn Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Ser His His Tyr Gly Leu Phe Asp Tyr
1               5
```

```
<210> SEQ ID NO 40
<211> LENGTH: 11
<212> TYPE: PRT
<213> ORGANISM: Artificial Sequence
<220> FEATURE:
<223> OTHER INFORMATION: Synthetic peptide

<400> SEQUENCE: 40

Ser Lys Ser Val Ser Thr Ser Gly Tyr Asn Tyr
1               5                   10

<210> SEQ ID NO 41
<211> LENGTH: 3
<212> TYPE: PRT
<213> ORGANISM: Artificial Sequence
<220> FEATURE:
<223> OTHER INFORMATION: Synthetic peptide

<400> SEQUENCE: 41

Leu Ala Ser
1

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Ser Arg Glu Leu Pro Arg Thr
1               5

<210> SEQ ID NO 43
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 43
gaggtgaagc ttctcgagtc tggaggtggc ctggtgcagc ctggaggatc cctgaaactc      60
tcctgtgtag cctcaggatt cgattttagt agatactgga tgagttgggt ccggcaggct     120
ccagggaaag ggccagaatg gattggagaa attaatccag aaagcaatac gatgaactat     180
tcgccatctc taaaggaaaa attcatcatc tccagagaca ccgccaaaaa tatgttgtac     240
ctgcaaatga gcaaagtgag atctgaggac acagcccttt attactgtgc aacctctcat     300
cactacggcc tattcgatta ctggggccaa gggactctgg tcactgtctc tgca            354

<210> SEQ ID NO 44
<211> LENGTH: 333
<212> TYPE: DNA
<213> ORGANISM: Artificial Sequence
<220> FEATURE:
<223> OTHER INFORMATION: Synthetic nucleotide sequence

<400> SEQUENCE: 44
gacattgtgc tgacacagtc tcctgcttcc ttagctgtgt ctctggggca gagggccacc      60
atctcatgca gggccagcaa aagtgtcagt acttctggct ataattatat acactggtac     120
caacagaaac caggacagcc acccaaactc ctcatctatc ttgcatccta cctagaatct     180
ggggtccctg ccaggttcag tggcagtggg tctgggacag acttcaccct caacatccac     240
cctgtggagg aggaggatgc tgcaacctat ttctgtcagc acagtaggga gcttcctcgg     300
```
acgttcggtg gaggcaccaa gctggaattc aaa      333

<210> SEQ ID NO 45
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: D or Y

<400> SEQUENCE: 45

Gly Phe Asp Phe Ser Arg Xaa Trp
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D or E
<220> FEATURE:
<221> NAME/KEY: MOD_RES
<222> LOCATION: (6)..(6)
<223> OTHER INFORMATION: S or N
<220> FEATURE:
<221> NAME/KEY: MOD_RES
<222> LOCATION: (8)..(8)
<223> OTHER INFORMATION: K or M

<400> SEQUENCE: 46

Ile Asn Pro Xaa Ser Xaa Thr Xaa
1               5

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Y or H
<220> FEATURE:
<221> NAME/KEY: MOD_RES
<222> LOCATION: (10)..(10)
<223> OTHER INFORMATION: G or D

<400> SEQUENCE: 47

Ala Thr Ser His Xaa Tyr Gly Leu Phe Xaa Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: S or N

<400> SEQUENCE: 48

```
Lys Ser Val Ser Thr Ser Gly Tyr Xaa Tyr
1               5                   10
```

<210> SEQ ID NO 49
<211> LENGTH: 3
<212> TYPE: PRT
<213> ORGANISM: Artificial Sequence
<220> FEATURE:
<223> OTHER INFORMATION: Synthetic peptide

<400> SEQUENCE: 49

```
Leu Ala Ser
1
```

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

```
Gln His Ser Arg Glu Leu Pro Arg Thr
1               5
```

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D or Y

<400> SEQUENCE: 51

```
Arg Xaa Trp Met Ser
1               5
```

<210> SEQ ID NO 52
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: D or E
<220> FEATURE:
<221> NAME/KEY: MOD_RES
<222> LOCATION: (7)..(7)
<223> OTHER INFORMATION: S or N
<220> FEATURE:
<221> NAME/KEY: MOD_RES
<222> LOCATION: (9)..(9)
<223> OTHER INFORMATION: K or M
<220> FEATURE:
<221> NAME/KEY: MOD_RES
<222> LOCATION: (12)..(12)
<223> OTHER INFORMATION: T or S
<220> FEATURE:
<221> NAME/KEY: MOD_RES
<222> LOCATION: (17)..(17)
<223> OTHER INFORMATION: D or E

<400> SEQUENCE: 52

```
Glu Ile Asn Pro Xaa Ser Xaa Thr Xaa Asn Tyr Xaa Pro Ser Leu Lys
1               5                   10                  15
```

Xaa

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Y or H
<220> FEATURE:
<221> NAME/KEY: MOD_RES
<222> LOCATION: (8)..(8)
<223> OTHER INFORMATION: G or D

<400> SEQUENCE: 53

Ser His Xaa Tyr Gly Leu Phe Xaa Tyr
1               5

<210> SEQ ID NO 54
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: S or N
<220> FEATURE:
<221> NAME/KEY: MOD_RES
<222> LOCATION: (14)..(14)
<223> OTHER INFORMATION: M or I

<400> SEQUENCE: 54

Arg Ala Ser Lys Ser Val Ser Thr Ser Gly Tyr Xaa Tyr Xaa His
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Leu Ala Ser Tyr Leu Glu Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Gln His Ser Arg Glu Leu Pro Arg Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide
<220> FEATURE:

```
<221> NAME/KEY: MOD_RES
<222> LOCATION: (7)..(7)
<223> OTHER INFORMATION: D or Y

<400> SEQUENCE: 57

Gly Phe Asp Phe Ser Arg Xaa
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D or E
<220> FEATURE:
<221> NAME/KEY: MOD_RES
<222> LOCATION: (5)..(5)
<223> OTHER INFORMATION: S or N

<400> SEQUENCE: 58

Asn Pro Xaa Ser Xaa Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Y or H
<220> FEATURE:
<221> NAME/KEY: MOD_RES
<222> LOCATION: (8)..(8)
<223> OTHER INFORMATION: G or D

<400> SEQUENCE: 59

Ser His Xaa Tyr Gly Leu Phe Xaa Tyr
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: S or N

<400> SEQUENCE: 60

Ser Lys Ser Val Ser Thr Ser Gly Tyr Xaa Tyr
1               5                   10

<210> SEQ ID NO 61
<211> LENGTH: 3
<212> TYPE: PRT
<213> ORGANISM: Artificial Sequence
<220> FEATURE:
<223> OTHER INFORMATION: Synthetic peptide

<400> SEQUENCE: 61

Leu Ala Ser
```

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ser Arg Glu Leu Pro Arg Thr
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic peptide

<400> SEQUENCE: 63

Gly Phe Asp Phe Ser Arg Asp Trp Met Ser
1               5                   10

<210> SEQ ID NO 64
<211> LENGTH: 17
<212> TYPE: PRT
<213> ORGANISM: Artificial Sequence
<220> FEATURE:
<223> OTHER INFORMATION: Synthetic peptide

<400> SEQUENCE: 64

Glu Ile Asn Pro Asp Ser Ser Thr Lys Asn Tyr Thr Pro Ser Leu Lys
1               5                   10                  15

Asp

<210> SEQ ID NO 65
<211> LENGTH: 11
<212> TYPE: PRT
<213> ORGANISM: Artificial Sequence
<220> FEATURE:
<223> OTHER INFORMATION: Synthetic peptide

<400> SEQUENCE: 65

Ala Thr Ser His Tyr Tyr Gly Leu Phe Gly Tyr
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Synthetic peptide

<400> SEQUENCE: 66

Arg Ala Ser Lys Ser Val Ser Thr Ser Gly Tyr Ser Tyr Met His
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

```
Leu Ala Ser Tyr Leu Glu Ser
1               5
```

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

```
Gln His Ser Arg Glu Leu Pro Arg Thr
1               5
```

<210> SEQ ID NO 69
<211> LENGTH: 10
<212> TYPE: PRT
<213> ORGANISM: Artificial Sequence
<220> FEATURE:
<223> OTHER INFORMATION: Synthetic peptide

<400> SEQUENCE: 69

```
Gly Phe Asp Phe Ser Arg Tyr Trp Met Ser
1               5                   10
```

<210> SEQ ID NO 70
<211> LENGTH: 17
<212> TYPE: PRT
<213> ORGANISM: Artificial Sequence
<220> FEATURE:
<223> OTHER INFORMATION: Synthetic peptide

<400> SEQUENCE: 70

```
Glu Ile Asn Pro Glu Ser Asn Thr Met Asn Tyr Ser Pro Ser Leu Lys
1               5                   10                  15

Glu
```

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide

<400> SEQUENCE: 71

```
Ala Thr Ser His His Tyr Gly Leu Phe Asp Tyr
1               5                   10
```

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide

<400> SEQUENCE: 72

```
Arg Ala Ser Lys Ser Val Ser Thr Ser Gly Tyr Asn Tyr Ile His
1               5                   10                  15
```

<210> SEQ ID NO 73
<211> LENGTH: 7
<212> TYPE: PRT
<213> ORGANISM: Artificial Sequence
<220> FEATURE:
<223> OTHER INFORMATION: Synthetic peptide

<400> SEQUENCE: 73

```
Leu Ala Ser Tyr Leu Glu Ser
1               5
```

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

```
Gln His Ser Arg Glu Leu Pro Arg Thr
1               5
```

<210> SEQ ID NO 75
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: D or Y

<400> SEQUENCE: 75

```
Gly Phe Asp Phe Ser Arg Xaa Trp Met Ser
1               5                   10
```

<210> SEQ ID NO 76
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: D or E
<220> FEATURE:
<221> NAME/KEY: MOD_RES
<222> LOCATION: (7)..(7)
<223> OTHER INFORMATION: S or N
<220> FEATURE:
<221> NAME/KEY: MOD_RES
<222> LOCATION: (9)..(9)
<223> OTHER INFORMATION: K or M
<220> FEATURE:
<221> NAME/KEY: MOD_RES
<222> LOCATION: (12)..(12)
<223> OTHER INFORMATION: T or S
<220> FEATURE:
<221> NAME/KEY: MOD_RES
<222> LOCATION: (17)..(17)
<223> OTHER INFORMATION: D or E

<400> SEQUENCE: 76

```
Glu Ile Asn Pro Xaa Ser Xaa Thr Xaa Asn Tyr Xaa Pro Ser Leu Lys
1               5                   10                  15

Xaa
```

<210> SEQ ID NO 77
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)

```
<223> OTHER INFORMATION: Y or H
<220> FEATURE:
<221> NAME/KEY: MOD_RES
<222> LOCATION: (10)..(10)
<223> OTHER INFORMATION: G or D

<400> SEQUENCE: 77

Ala Thr Ser His Xaa Tyr Gly Leu Phe Xaa Tyr
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: S or N
<220> FEATURE:
<221> NAME/KEY: MOD_RES
<222> LOCATION: (14)..(14)
<223> OTHER INFORMATION: M or I

<400> SEQUENCE: 78

Arg Ala Ser Lys Ser Val Ser Thr Ser Gly Tyr Xaa Tyr Xaa His
1               5                   10                  15

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Leu Ala Ser Tyr Leu Glu Ser
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Gln His Ser Arg Glu Leu Pro Arg Thr
1               5

<210> SEQ ID NO 81
<211> LENGTH: 2
<212> TYPE: PRT
<213> ORGANISM: Artificial Sequence
<220> FEATURE:
<223> OTHER INFORMATION: Synthetic peptide

<400> SEQUENCE: 81

Arg Asp
1

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 82

Asn Pro Asp Ser Ser Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

<400> SEQUENCE: 83

Ser His Tyr Tyr Gly Leu Phe Gly Tyr
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide

<400> SEQUENCE: 84

Lys Ser Val Ser Thr Ser Gly Tyr Ser Tyr
1               5                   10

<210> SEQ ID NO 85
<211> LENGTH: 3
<212> TYPE: PRT
<213> ORGANISM: Artificial Sequence
<220> FEATURE:
<223> OTHER INFORMATION: Synthetic peptide

<400> SEQUENCE: 85

Leu Ala Ser
1

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

Ser Arg Glu Leu Pro Arg Thr
1               5

<210> SEQ ID NO 87
<211> LENGTH: 2
<212> TYPE: PRT
<213> ORGANISM: Artificial Sequence
<220> FEATURE:
<223> OTHER INFORMATION: Synthetic peptide

<400> SEQUENCE: 87

Arg Tyr
1

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide

<400> SEQUENCE: 88
```

```
Asn Pro Glu Ser Asn Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

<400> SEQUENCE: 89

Ser His His Tyr Gly Leu Phe Asp Tyr
1               5

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide

<400> SEQUENCE: 90

Lys Ser Val Ser Thr Ser Gly Tyr Asn Tyr
1               5                   10

<210> SEQ ID NO 91
<211> LENGTH: 3
<212> TYPE: PRT
<213> ORGANISM: Artificial Sequence
<220> FEATURE:
<223> OTHER INFORMATION: Synthetic peptide

<400> SEQUENCE: 91

Leu Ala Ser
1

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Ser Arg Glu Leu Pro Arg Thr
1               5

<210> SEQ ID NO 93
<211> LENGTH: 2
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D or Y

<400> SEQUENCE: 93

Arg Xaa
1

<210> SEQ ID NO 94
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (3)..(3)
<223> OTHER INFORMATION: D or E
<220> FEATURE:
<221> NAME/KEY: MOD_RES
<222> LOCATION: (5)..(5)
<223> OTHER INFORMATION: S or N

<400> SEQUENCE: 94

Asn Pro Xaa Ser Xaa Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Y or H
<220> FEATURE:
<221> NAME/KEY: MOD_RES
<222> LOCATION: (8)..(8)
<223> OTHER INFORMATION: G or D

<400> SEQUENCE: 95

Ser His Xaa Tyr Gly Leu Phe Xaa Tyr
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: S or N

<400> SEQUENCE: 96

Lys Ser Val Ser Thr Ser Gly Tyr Xaa Tyr
1               5                   10

<210> SEQ ID NO 97
<211> LENGTH: 3
<212> TYPE: PRT
<213> ORGANISM: Artificial Sequence
<220> FEATURE:
<223> OTHER INFORMATION: Synthetic peptide

<400> SEQUENCE: 97

Leu Ala Ser
1

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

Ser Arg Glu Leu Pro Arg Thr
1               5
```

```
<210> SEQ ID NO 99
<211> LENGTH: 15
<212> TYPE: PRT
<213> ORGANISM: Artificial Sequence
<220> FEATURE:
<223> OTHER INFORMATION: Synthetic peptide

<400> SEQUENCE: 99

Arg Pro Ala Pro Gly Ser Thr Ala Pro Pro Ala His Gly Val Thr
1               5                   10                  15

<210> SEQ ID NO 100
<211> LENGTH: 4
<212> TYPE: PRT
<213> ORGANISM: Artificial Sequence
<220> FEATURE:
<223> OTHER INFORMATION: Synthetic peptide

<400> SEQUENCE: 100

Gly Phe Leu Gly
1

<210> SEQ ID NO 101
<211> LENGTH: 4
<212> TYPE: PRT
<213> ORGANISM: Artificial Sequence
<220> FEATURE:
<223> OTHER INFORMATION: Synthetic peptide

<400> SEQUENCE: 101

Ala Leu Ala Leu
1

<210> SEQ ID NO 102
<211> LENGTH: 24
<212> TYPE: PRT
<213> ORGANISM: Artificial Sequence
<220> FEATURE:
<223> OTHER INFORMATION: Synthetic peptide

<400> SEQUENCE: 102

Tyr Leu His Leu Gly Ala Leu Gly Arg Asp Leu Trp Gly Pro Ser Pro
1               5                   10                  15

Val Thr Gly Tyr His Pro Leu Leu
            20

<210> SEQ ID NO 103
<211> LENGTH: 27
<212> TYPE: PRT
<213> ORGANISM: Artificial Sequence
<220> FEATURE:
<223> OTHER INFORMATION: Synthetic peptide

<400> SEQUENCE: 103

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 104
<211> LENGTH: 44
<212> TYPE: PRT
<213> ORGANISM: Artificial Sequence
<220> FEATURE:
<223> OTHER INFORMATION: Synthetic peptide
```

```
<400> SEQUENCE: 104

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys
        35                  40

<210> SEQ ID NO 105
<211> LENGTH: 28
<212> TYPE: PRT
<213> ORGANISM: Artificial Sequence
<220> FEATURE:
<223> OTHER INFORMATION: Synthetic peptide

<400> SEQUENCE: 105

Thr Ala Pro Pro Ala His Gly Val Thr Ser Ala Pro Asp Thr Arg Pro
1               5                   10                  15

Ala Pro Gly Ser Thr Ala Pro Pro Ala His Gly Val
            20                  25

<210> SEQ ID NO 106
<211> LENGTH: 28
<212> TYPE: PRT
<213> ORGANISM: Artificial Sequence
<220> FEATURE:
<223> OTHER INFORMATION: Synthetic peptide

<400> SEQUENCE: 106

Thr Ala Pro Pro Ala His Gly Val Thr Ser Ala Pro Ala Thr Arg Pro
1               5                   10                  15

Ala Pro Gly Ser Thr Ala Pro Pro Ala His Gly Val
            20                  25

<210> SEQ ID NO 107
<211> LENGTH: 28
<212> TYPE: PRT
<213> ORGANISM: Artificial Sequence
<220> FEATURE:
<223> OTHER INFORMATION: Synthetic peptide

<400> SEQUENCE: 107

Thr Ala Pro Pro Ala His Gly Val Thr Ser Ala Pro Asp Ala Arg Pro
1               5                   10                  15

Ala Pro Gly Ser Thr Ala Pro Pro Ala His Gly Val
            20                  25

<210> SEQ ID NO 108
<211> LENGTH: 28
<212> TYPE: PRT
<213> ORGANISM: Artificial Sequence
<220> FEATURE:
<223> OTHER INFORMATION: Synthetic peptide

<400> SEQUENCE: 108

Thr Ala Pro Pro Ala His Gly Val Thr Ser Ala Pro Asp Thr Ala Pro
1               5                   10                  15

Ala Pro Gly Ser Thr Ala Pro Pro Ala His Gly Val
            20                  25

<210> SEQ ID NO 109
<211> LENGTH: 28
<212> TYPE: PRT
```

```
<213> ORGANISM: Artificial Sequence
<220> FEATURE:
<223> OTHER INFORMATION: Synthetic peptide

<400> SEQUENCE: 109

Thr Ala Pro Pro Ala His Gly Val Thr Ser Ala Pro Asp Thr Arg Ala
1               5                   10                  15

Ala Pro Gly Ser Thr Ala Pro Pro Ala His Gly Val
            20                  25

<210> SEQ ID NO 110
<211> LENGTH: 28
<212> TYPE: PRT
<213> ORGANISM: Artificial Sequence
<220> FEATURE:
<223> OTHER INFORMATION: Synthetic peptide

<400> SEQUENCE: 110

Thr Ala Pro Pro Ala His Gly Val Thr Ser Ala Pro Asp Thr Arg Pro
1               5                   10                  15

Gly Pro Gly Ser Thr Ala Pro Pro Ala His Gly Val
            20                  25

<210> SEQ ID NO 111
<211> LENGTH: 28
<212> TYPE: PRT
<213> ORGANISM: Artificial Sequence
<220> FEATURE:
<223> OTHER INFORMATION: Synthetic peptide

<400> SEQUENCE: 111

Thr Ala Pro Pro Ala His Gly Val Thr Ser Ala Pro Asp Thr Arg Pro
1               5                   10                  15

Ala Ala Gly Ser Thr Ala Pro Pro Ala His Gly Val
            20                  25

<210> SEQ ID NO 112
<211> LENGTH: 28
<212> TYPE: PRT
<213> ORGANISM: Artificial Sequence
<220> FEATURE:
<223> OTHER INFORMATION: Synthetic peptide

<400> SEQUENCE: 112

Thr Ala Pro Pro Ala His Gly Val Thr Ser Ala Pro Asp Thr Arg Pro
1               5                   10                  15

Ala Pro Ala Ser Thr Ala Pro Pro Ala His Gly Val
            20                  25

<210> SEQ ID NO 113
<211> LENGTH: 28
<212> TYPE: PRT
<213> ORGANISM: Artificial Sequence
<220> FEATURE:
<223> OTHER INFORMATION: Synthetic peptide

<400> SEQUENCE: 113

Thr Ala Pro Pro Ala His Gly Val Thr Ser Ala Pro Asp Thr Arg Pro
1               5                   10                  15

Ala Pro Gly Ala Thr Ala Pro Pro Ala His Gly Val
            20                  25

<210> SEQ ID NO 114
<211> LENGTH: 28
```

```
<212> TYPE: PRT
<213> ORGANISM: Artificial Sequence
<220> FEATURE:
<223> OTHER INFORMATION: Synthetic peptide

<400> SEQUENCE: 114

Thr Ala Pro Pro Ala His Gly Val Thr Ser Ala Pro Asp Thr Arg Pro
1               5                   10                  15

Ala Pro Gly Ser Ala Ala Pro Pro Ala His Gly Val
            20                  25

<210> SEQ ID NO 115
<211> LENGTH: 28
<212> TYPE: PRT
<213> ORGANISM: Artificial Sequence
<220> FEATURE:
<223> OTHER INFORMATION: Synthetic peptide

<400> SEQUENCE: 115

Thr Ala Pro Pro Ala His Gly Val Thr Ser Ala Pro Asp Thr Arg Pro
1               5                   10                  15

Ala Pro Gly Ser Thr Gly Pro Pro Ala His Gly Val
            20                  25

<210> SEQ ID NO 116
<211> LENGTH: 28
<212> TYPE: PRT
<213> ORGANISM: Artificial Sequence
<220> FEATURE:
<223> OTHER INFORMATION: Synthetic peptide

<400> SEQUENCE: 116

Thr Ala Pro Pro Ala His Gly Val Thr Ser Ala Pro Asp Thr Arg Pro
1               5                   10                  15

Ala Pro Gly Ser Thr Ala Ala Pro Ala His Gly Val
            20                  25

<210> SEQ ID NO 117
<211> LENGTH: 28
<212> TYPE: PRT
<213> ORGANISM: Artificial Sequence
<220> FEATURE:
<223> OTHER INFORMATION: Synthetic peptide

<400> SEQUENCE: 117

Thr Ala Pro Pro Ala His Gly Val Thr Ser Ala Pro Asp Thr Arg Pro
1               5                   10                  15

Ala Pro Gly Ser Thr Ala Pro Ala Ala His Gly Val
            20                  25

<210> SEQ ID NO 118
<211> LENGTH: 20
<212> TYPE: PRT
<213> ORGANISM: Artificial Sequence
<220> FEATURE:
<223> OTHER INFORMATION: Synthetic peptide

<400> SEQUENCE: 118

Pro Pro Glu Arg Gly Ala Pro Pro Ser Thr Phe Lys Gly Thr Pro Thr
1               5                   10                  15

Ala Glu Asn Pro
            20
```

ANTI-GLYCO-MUC1 ANTIBODIES AND THEIR USES

1. CROSS-REFERENCE TO RELATED APPLICATIONS

This application claims the priority benefit of U.S. provisional application No. 62/691,887, filed Jun. 29, 2018, and 62/802,865, filed Feb. 8, 2019, the contents of each of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Jun. 26, 2019, is named GOT-002WO_SL and is 33,365 bytes in size.

3. BACKGROUND

The human mucin MUC1 is a polymorphic transmembrane glycoprotein expressed on the apical surfaces of simple and glandular epithelia (Taylor-Papadimitriou et al., 1999, Biochim. Biophys. Acta, 1455:301-313). MUC1 is highly overexpressed and aberrantly O-glycosylated in adenocarcinomas. The extracellular domain of the mucin contains variable number of tandem repeats (TRs) (25-125) of 20 amino acid residues with five potential sites for O-glycosylation. O-Glycans are incompletely processed in cancer cells resulting in the expression of the pancarcinoma carbohydrate antigens Tn (GalNAcα1-O-Ser/Thr) (Springer, 1984, Science 224:1198-1206). Simple mucin-type O-glycans, Tn, are widely expressed in adenocarcinomas (including breast and ovarian cancers) and show limited distribution in normal adult tissues (Springer, 1984, Science 224: 1198-1206). The expression of these O-glycans in cancer correlates with poor prognosis and natural antibodies to these carbohydrate haptens increases in cancer patients (Miles, et al., 1995, Br. J. Cancer. 71:1074-1076; Soares et al., 1996, Pathol. Res. Pract. 192:1181-1186; Werther et al., 1996, Int. J. Cancer. 69:193-199). There is a need in the art for therapeutic modalities that utilize glyco-MUC1 epitopes that are overexpressed in cancer cells.

4. SUMMARY

The disclosure captures the tumor specificity of glycopeptide variants by providing therapeutic and diagnostic agents based on antibodies and antigen binding fragments that are selective for cancer-specific epitopes of glyco-MUC1.

The present disclosure provides anti-glyco-MUC1 antibodies and antigen binding fragments thereof that bind to a cancer-specific glycosylation variant of MUC1. The present disclosure further provides fusion proteins and antibody-drug conjugates comprising anti-glyco-MUC1 antibodies and antigen binding fragments, and nucleic acids encoding the anti-glyco-MUC1 antibodies, antigen binding fragments and fusion proteins.

The present disclosure further provides methods of using the anti-glyco-MUC1 antibodies, antigen-binding fragments, fusion proteins, antibody-drug conjugates and nucleic acids for cancer therapy.

In certain aspects, the disclosure provides bispecific and other multispecific anti-glyco-MUC1 antibodies and antigen binding fragments that bind to a cancer-specific glycosylation variant of MUC1 and to a second epitope. The second epitope can either be on MUC1 itself, on another protein co-expressed on cancer cells with MUC1, or on another protein presented on a different cell, such as an activated T cell. Further, also disclosed are nucleic acids encoding such antibodies, including nucleic acids comprising codon-optimized coding regions and nucleic acids comprising coding regions that are not codon-optimized for expression in a particular host cell.

The anti-glyco-MUC1 antibodies and binding fragments can be in the form of fusion proteins containing a fusion partner. The fusion partner can be useful to provide a second function, such as a signaling function of the signaling domain of a T cell signaling protein, a peptide modulator of T cell activation or an enzymatic component of a labeling system. Exemplary T cell signaling proteins include 4-1BB, CO3C, and fusion peptides, e.g., CD28-CD3-zeta and 4-1 BB-CD3-zeta. 4-1BB, or CD137, is a co-stimulatory receptor of T cells; CD3-zeta is a signal-transduction component of the T-cell antigen receptor. The moiety providing a second function can be a modulator of T cell activation, such as IL-15, IL-15Ra, or an IL-15/IL-15Ra fusion, or it can encode a label or an enzymatic component of a labeling system useful in monitoring the extent and/or location of binding in vivo or in vitro. Constructs encoding these prophylactically and therapeutically active biomolecules placed in the context of T cells, such as autologous T cells, provide a powerful platform for recruiting adoptively transferred T cells to prevent or treat a variety of cancers in some embodiments of the disclosure.

In certain aspects, an anti-glyco-MUC1 antibody or antigen-binding fragment of the disclosure comprises heavy and/or light chain variable sequences (or encoded by the nucleotide sequences) set forth in Table 1A and Table 1B. For clarity, when the term "anti-glyco-MUC1 antibody" is used in this document, it is intended to include monospecific and multi-specific (including bispecific) anti-glyco-MUC1 antibodies, antigen-binding fragments of the monospecific and multi-specific antibodies, and fusion proteins and conjugates containing the antibodies and their antigen-binding fragments, unless the context dictates otherwise. Likewise, when the term when the term "anti-glyco-MUC1 antibody or antigen-binding fragment" is used, it is also intended to include monospecific and multi-specific (including bispecific) anti-glyco-MUC1 antibodies and their antigen-binding fragments, together with fusion proteins and conjugates containing such antibodies and antigen-binding fragments, unless the context dictates otherwise.

In other aspects, an anti-glyco-MUC1 antibody or antigen-binding fragment of the disclosure comprises heavy and/or light chain CDR sequences (or encoded by the nucleotide sequences) set forth in Tables 1-3. The CDR sequences set forth in Table 1A and Table 1B include CDR sequences defined according to the IMGT (Lefranc et al., 2003, Dev Comparat Immunol 27:55-77), Kabat (Kabat et al., 1991, Sequences of Proteins of Immunological Interest, 5th Ed. Public Health Service, National Institutes of Health, Bethesda, Md.), and Chothia (Al-Lazikani et al., 1997, J. Mol. Biol 273:927-948) schemes for defining CDR boundaries. The CDR sequences set forth in Table 1C, Table 1D, and Table 1E are consensus sequences derived from the CDR sequences set forth in Table 1A and Table 1B according to the IMGT, Kabat, and Chothia definitions, respectively. The CDR sequences set forth in Table 2A and Table 2B are the combined regions of overlap for the CDR sequences set forth in Table 1A and Table 1B, respectively, with the IMGT, Kabat and Chothia sequences shown in underlined bold text. The CDR sequences set forth in Table 2C are the combined regions of overlap for the consensus CDR sequences set forth in Table 1C, Table 1D, and Table 1E. The CDR sequences set forth in Table 3A and Table 3B are the common regions of overlap for the CDR sequences shown in Table 1A and Table 1B, respectively. The CDR sequences set forth in Table 3C are the common regions of overlap for the CDR sequences set forth in Table 1C, Table 1D, and Table 1E. The framework sequences for such anti-glyco-MUC1 antibody and antigen-binding fragment can be the native murine framework sequences of the VH and VL sequences set forth in Table 1A or Table 1B or can be non-native (e.g., humanized or human) framework sequences.

TABLE 1A

1AG Sequences

| Description | Sequence | SEQ ID NO: |
|---|---|---|
| VH amino acid sequence (predicted mature) | EVKLLESGGGLVQPGGSLKLSCAASGFDFSRDWMSWV RQAPGKGLEWIGEINPDSSTKNYTPSLKDKFIISRDNAKN TLFLQMSSVRSEDTALYYCATSHYYGLFGYWGQGTLVT VSA | 1 |
| VL amino acid sequence (predicted mature) | DIVLTQSPASLTVSLGQRATISCRASKSVSTSGYSYMHW YQQKPGQPPKLLIYLASYLESGVPARFSGSGSGTDFTLN IHPVEEEDAATYYCQHSRELPRTFGGGTKLEIK | 2 |
| CDR-H1 amino acid sequence (IMGT definition) | GFDFSRDW | 3 |
| CDR-H2 amino acid sequence (IMGT definition) | INPDSSTK | 4 |
| CDR-H3 amino acid sequence (IMGT definition) | ATSHYYGLFGY | 5 |
| CDR-L1 amino acid sequence (IMGT definition) | KSVSTSGYSY | 6 |
| CDR-L2 amino acid sequence (IMGT definition) | LAS | 7 |
| CDR-L3 amino acid sequence (IMGT definition) | QHSRELPRT | 8 |
| CDR-H1 amino acid sequence (Kabat definition) | RDWMS | 9 |
| CDR-H2 amino acid sequence (Kabat definition) | EINPDSSTKNYTPSLKD | 10 |
| CDR-H3 amino acid sequence (Kabat definition) | SHYYGLFGY | 11 |
| CDR-L1 amino acid sequence (Kabat definition) | RASKSVSTSGYSYMH | 12 |
| CDR-L2 amino acid sequence (Kabat definition) | LASYLES | 13 |

TABLE 1A-continued

1AG Sequences

| Description | Sequence | SEQ ID NO: |
|---|---|---|
| CDR-L3 amino acid sequence (Kabat definition) | QHSRELPRT | 14 |
| CDR-H1 amino acid sequence (Chothia definition) | GFDFSRD | 15 |
| CDR-H2 amino acid sequence (Chothia definition) | NPDSST | 16 |
| CDR-H3 amino acid sequence (Chothia definition) | SHYYGLFGY | 17 |
| CDR-L1 amino acid sequence (Chothia definition) | SKSVSTSGYSY | 18 |
| CDR-L2 amino acid sequence (Chothia definition) | LAS | 19 |
| CDR-L3 amino acid sequence (Chothia definition) | SRELPRT | 20 |
| VH nucleotide sequence (excl. signal sequence) | GAGGTGAAGCTTCTCGAGTCTGGAGGTGGCCTGGTG CAGCCTGGAGGATCCCTGAAATTGTCCTGTGCAGCCT CAGGATTCGATTTTAGTAGAGACTGGATGAGTTGGGT CCGGCAGGCTCCAGGGAAAGGGCTAGAATGGATTGG AGAGATTAATCCAGATAGCAGTACGAAAAACTACACG CCATCTCTAAAGGATAAATTCATCATTTCCAGAGACAA CGCCAAAAATACGCTGTTCCTGCAAATGAGCAGCGTG AGATCTGAGGACACAGCCCTTTATTACTGTGCAACCT CTCATTACTACGGCCTGTTTGGTTACTGGGGCCAAGG GACTCTGGTCACTGTCTCTGCAGAGGTGAAGCTTCTC GAGTCTGGAGGTGGCCTGGTGCAGCCTGGAGGATCC CTGAAATTGTCCTGTGCAGCCTCAGGATTCGATTTTAG TAGAGACTGGATGAGTTGGGTCCGGCAGGCTCCAGG GAAAGGGCTAGAATGGATTGGAGAGATTAATCCAGAT AGCAGTACGAAAAACTACACGCCATCTCTAAAGGATA AATTCATCATTTCCAGAGACAACGCCAAAAATACGCTG TTCCTGCAAATGAGCAGCGTGAGATCTGAGGACACAG CCCTTTATTACTGTGCAACCTCTCATTACTACGGCCTG TTTGGTTACTGGGGCCAAGGGACTCTGGTCACTGTCT CTGCA | 21 |
| VL nucleotide sequence (excl. signal sequence) | GACATTGTGCTGACACAGTCTCCTGCTTCCTTAACTGT ATCTCTGGGGCAGAGGGCCACCATCTCATGCAGGGC CAGCAAAAGTGTCAGTACATCTGGCTATAGTTATATGC ACTGGTACCAACAGAAACCAGGACAGCCACCCAAACT CCTCATCTATCTTGCTTCCTACCTAGAATCTGGGGTCC CTGCCAGGTTCAGTGGCAGTGGGTCTGGGACAGACT TCACCCTCAACATCCATCCTGTGGAGGAGGAGGATGC TGCAACCTATTACTGTCAGCACAGTAGGGAGCTTCCT CGGACGTTCGGTGGAGGCACCAAGCTGGAAATCAAA | 22 |

TABLE 1B

| Description | Sequence | SEQ ID NO: |
|---|---|---|
| VH amino acid sequence (predicted mature) | EVKLLESGGGLVQPGGSLKLSCVASGFDFSRYWMSWV RQAPGKGPEWIGEINPESNTMNYSPSLKEKFIISRDTAK NMLYLQMSKVRSEDTALYYCATSHHYGLFDYWGQGTL VTVSA | 23 |
| VL amino acid sequence (predicted mature) | DIVLTQSPASLAVSLGQRATISCRASKSVSTSGYNYIHWY QQKPGQPPKLLIYLASYLESGVPARFSGSGSGTDFTLNI HPVEEEDAATYFCQHSRELPRTFGGGTKLEFK | 24 |
| CDR-H1 amino acid sequence (IMGT definition) | GFDFSRYW | 25 |
| CDR-H2 amino acid sequence (IMGT definition) | INPESNTM | 26 |
| CDR-H3 amino acid sequence (IMGT definition) | ATSHHYGLFDY | 27 |
| CDR-L1 amino acid sequence (IMGT definition) | KSVSTSGYNY | 28 |
| CDR-L2 amino acid sequence (IMGT definition) | LAS | 29 |
| CDR-L3 amino acid sequence (IMGT definition) | QHSRELPRT | 30 |
| CDR-H1 amino acid sequence (Kabat definition) | RYWMS | 31 |
| CDR-H2 amino acid sequence (Kabat definition) | EINPESNTMNYSPSLKE | 32 |
| CDR-H3 amino acid sequence (Kabat definition) | SHHYGLFDY | 33 |
| CDR-L1 amino acid sequence (Kabat definition) | RASKSVSTSGYNYIH | 34 |
| CDR-L2 amino acid sequence (Kabat definition) | LASYLES | 35 |
| CDR-L3 amino acid sequence (Kabat definition) | QHSRELPRT | 36 |
| CDR-H1 amino acid sequence (Chothia definition) | GFDFSRY | 37 |

TABLE 1B-continued

4AG Sequences

| Description | Sequence | SEQ ID NO: |
|---|---|---|
| CDR-H2 amino acid sequence (Chothia definition) | NPESNT | 38 |
| CDR-H3 amino acid sequence (Chothia definition) | SHHYGLFDY | 39 |
| CDR-L1 amino acid sequence (Chothia definition) | SKSVSTSGYNY | 40 |
| CDR-L2 amino acid sequence (Chothia definition) | LAS | 41 |
| CDR-L3 amino acid sequence (Chothia definition) | SRELPRT | 42 |
| VH nucleotide sequence (excl. signal sequence) | GAGGTGAAGCTTCTCGAGTCTGGAGGTGGCCTGGTG CAGCCTGGAGGATCCCTGAAACTCTCCTGTGTAGCCT CAGGATTCGATTTTAGTAGATACTGGATGAGTTGGGT CCGGCAGGCTCCAGGGAAAGGGCCAGAATGGATTGG AGAAATTAATCCAGAAAGCAATACGATGAACTATTCGC CATCTCTAAAGGAAAAATTCATCATCTCCAGAGACACC GCCAAAAATATGTTGTACCTGCAAATGAGCAAAGTGA GATCTGAGGACACAGCCCTTTATTACTGTGCAACCTC TCATCACTACGGCCTATTCGATTACTGGGGCCAAGGG ACTCTGGTCACTGTCTCTGCA | 43 |
| VL nucleotide sequence (excl. signal sequence) | GACATTGTGCTGACACAGTCTCCTGCTTCCTTAGCTG TGTCTCTGGGGCAGAGGGCCACCATCTCATGCAGGG CCAGCAAAAGTGTCAGTACTTCTGGCTATAATTATATA CACTGGTACCAACAGAAACCAGGACAGCCACCCAAAC TCCTCATCTATCTTGCATCCTACCTAGAATCTGGGGTC CCTGCCAGGTTCAGTGGCAGTGGGTCTGGGACAGAC TTCACCCTCAACATCCACCCTGTGGAGGAGGAGGATG CTGCAACCTATTTCTGTCAGCACAGTAGGGAGCTTCC TCGGACGTTCGGTGGAGGCACCAAGCTGGAATTCAAA | 44 |

TABLE 1C

CDR Consensus sequences - IMGT definition

| Description | Sequence | SEQ ID NO: |
|---|---|---|
| CDR-H1 amino acid sequence (IMGT definition) | GFDFSRX1W<br>$X_1$ = D or Y | 45 |
| CDR-H2 amino acid sequence (IMGT definition) | INPX1SX2TX3<br>$X_1$ = D or E<br>$X_2$ = S or N<br>$X_3$ = K or M | 46 |
| CDR-H3 amino acid sequence (IMGT definition) | ATSHX1YGLFX2Y<br>$X_1$ = Y or H<br>$X_2$ = G or D | 47 |
| CDR-L1 amino acid sequence (IMGT definition) | KSVSTSGYX1Y<br>$X_1$ = S or N | 48 |
| CDR-L2 amino acid sequence (IMGT definition) | LAS | 49 |
| CDR-L3 amino acid sequence (IMGT definition) | QHSRELPRT | 50 |

TABLE 1D

CDR Consensus sequences - Kabat definition

| Description | Sequence | SEQ ID NO: |
|---|---|---|
| CDR-H1 amino acid sequence (Kabat definition) | RX$_1$WMS<br>X$_1$ = D or Y | 51 |
| CDR-H2 amino acid sequence (Kabat definition) | EINPX$_1$SX$_2$TX$_3$NYX$_4$PSLKX$_5$<br>X$_1$ = D or E<br>X$_2$ = S or N<br>X$_3$ = K or M<br>X$_4$ = T or S<br>X$_5$ = D or E | 52 |
| CDR-H3 amino acid sequence (Kabat definition) | SHX1YGLFX2Y<br>X$_1$ = Y or H<br>X$_2$ = G or D | 53 |
| CDR-L1 amino acid sequence (Kabat definition) | RASKSVSTSGYX$_1$YX$_2$H<br>X$_1$ = S or N<br>X$_2$ = M or I | 54 |
| CDR-L2 amino acid sequence (Kabat definition) | LASYLES | 55 |
| CDR-L3 amino acid sequence (Kabat definition) | QHSRELPRT | 56 |

TABLE 1E

CDR Consensus sequences - Chothia definition

| Description | Sequence | SEQ ID NO: |
|---|---|---|
| CDR-H1 amino acid sequence (Chothia definition) | GFDFSRX$_1$<br>X$_1$ = D or Y | 57 |
| CDR-H2 amino acid sequence (Chothia definition) | NPX$_1$SX$_2$T<br>X$_1$ = D or E<br>X$_2$ = S or N | 58 |
| CDR-H3 amino acid sequence (Chothia definition) | SHX1YGLFX2Y<br>X$_1$ = Y or H<br>X$_2$ = G or D | 59 |
| CDR-L1 amino acid sequence (Chothia definition) | SKSVSTSGYX$_1$Y<br>X$_1$ = S or N | 60 |
| CDR-L2 amino acid sequence (Chothia definition) | LAS | 61 |
| CDR-L3 amino acid sequence (Chothia definition) | SRELPRT | 62 |

TABLE 2A

1AG IMGT, Kabat, and Chothia CDR combined overlap sequences

| Description | Sequence | SEQ ID NO: |
|---|---|---|
| CDR-H1 amino acid sequence (combined overlap) | GFDFSRDWMS (IMGT)<br>GFDFSRDWMS (Kabat)<br>GFDFSRDWMS (Chothia) | 63 |
| CDR-H2 amino acid sequence (combined overlap) | EINPDSSTKNYTPSLKD (IMGT)<br>EINPDSSTKNYTPSLKD (Kabat)<br>EINPDSSTKNYTPSLKD (Chothia) | 64 |
| CDR-H3 amino acid sequence (combined overlap) | ATSHYYGLFGY (IMGT)<br>ATSHYYGLFGY (Kabat)<br>ATSHYYGLFGY (Chothia) | 65 |
| CDR-L1 amino acid sequence (combined overlap) | RASKSVSTSGYSYMH (IMGT)<br>RASKSVSTSGYSYMH (Kabat)<br>RASKSVSTSGYSYMH (Chothia) | 66 |
| CDR-L2 amino acid sequence (combined overlap) | LASYLES (IMGT)<br>LASYLES (Kabat)<br>LASYLES (Chothia) | 67 |
| CDR-L3 amino acid sequence (combined overlap) | QHSRELPRT (IMGT)<br>QHSRELPRT (Kabat)<br>QHSRELPRT (Chothia) | 68 |

TABLE 2B

4AG IMGT, Kabat, and Chothia CDR combined overlap sequences

| Description | Sequence | SEQ ID NO: |
|---|---|---|
| CDR-H1 amino acid sequence (combined overlap) | GFDFSRYWMS (IMGT)<br>GFDFSRYWMS (Kabat)<br>GFDFSRYWMS (Chothia) | 69 |
| CDR-H2 amino acid sequence (combined overlap) | EINPESNTMNYSPSLKE (IMGT)<br>EINPESNTMNYSPSLKE (Kabat)<br>EINPESNTMNYSPSLKE (Chothia) | 70 |
| CDR-H3 amino acid sequence (combined overlap) | ATSHHYGLFDY (IMGT)<br>ATSHHYGLFDY (Kabat)<br>ATSHHYGLFDY (Chothia) | 71 |
| CDR-L1 amino acid sequence (combined overlap) | RASKSVSTSGYNYIH (IMGT)<br>RASKSVSTSGYNYIH (Kabat)<br>RASKSVSTSGYNYIH (Chothia) | 72 |
| CDR-L2 amino acid sequence (combined overlap) | LASYLES (IMGT)<br>LASYLES (Kabat)<br>LASYLES (Chothia) | 73 |
| CDR-L3 amino acid sequence (combined overlap) | QHSRELPRT (IMGT)<br>QHSRELPRT (Kabat)<br>QHSRELPRT (Chothia) | 74 |

TABLE 2C

Consensus CDR combined overlap sequences

| Description | Sequence | SEQ ID NO: |
|---|---|---|
| CDR-H1 amino acid sequence (combined overlap) | GFDFSRX$_1$WMS<br>X$_1$ = D or Y | 75 |
| CDR-H2 amino acid sequence (combined overlap) | EINPX$_1$SX$_2$TX$_3$NYX$_4$PSLKX$_5$<br>X$_1$ = D or E<br>X$_2$ = S or N<br>X$_3$ = K or M<br>X$_4$ = T or S<br>X$_5$ = D or E | 76 |

TABLE 2C-continued

Consensus CDR combined overlap sequences

| Description | Sequence | SEQ ID NO: |
|---|---|---|
| CDR-H3 amino acid sequence (combined overlap) | ATSHX$_1$YGLFX$_2$Y<br>X$_1$ = Y or H<br>X$_2$ = G or D | 77 |
| CDR-L1 amino acid sequence (combined overlap) | RASKSVSTSGYX$_1$YX$_2$H<br>X$_1$ = S or N<br>X$_2$ = M or I | 78 |
| CDR-L2 amino acid sequence (combined overlap) | LASYLES | 79 |
| CDR-L3 amino acid sequence (combined overlap) | QHSRELPRT | 80 |

TABLE 3A

1AG IMGT, Kabat, and Chothia CDR common sequences

| Description | Sequence | SEQ ID NO: |
|---|---|---|
| CDR-H1 amino acid sequence (common sequence) | RD | 81 |
| CDR-H2 amino acid sequence (common sequence) | NPDSST | 82 |
| CDR-H3 amino acid sequence (common sequence) | SHYYGLFGY | 83 |
| CDR-L1 amino acid sequence (common sequence) | KSVSTSGYSY | 84 |
| CDR-L2 amino acid sequence (common sequence) | LAS | 85 |
| CDR-L3 amino acid sequence (common sequence) | SRELPRT | 86 |

TABLE 3B

4AG IMGT, Kabat, and Chothia CDR common sequences

| Description | Sequence | SEQ ID NO: |
|---|---|---|
| CDR-H1 amino acid sequence (common sequence) | RY | 87 |
| CDR-H2 amino acid sequence (common sequence) | NPESNT | 88 |
| CDR-H3 amino acid sequence (common sequence) | SHHYGLFDY | 89 |
| CDR-L1 amino acid sequence (common sequence) | KSVSTSGYNY | 90 |
| CDR-L2 amino acid sequence (common sequence) | LAS | 91 |
| CDR-L3 amino acid sequence (common sequence) | SRELPRT | 92 |

TABLE 3C

Consensus CDR common sequences

| Description | Sequence | SEQ ID NO: |
|---|---|---|
| CDR-H1 amino acid sequence (common sequence) | RX$_1$<br>X$_1$ = D or Y | 93 |
| CDR-H2 amino acid sequence (common sequence) | NPX$_1$SX$_2$T<br>X$_1$ = D or E<br>X$_2$ = S or N | 94 |
| CDR-H3 amino acid sequence (common sequence) | SHX1YGLFX2Y<br>X$_1$ = Y or H<br>X$_2$ = G or D | 95 |
| CDR-L1 amino acid sequence (common sequence) | KSVSTSGYX$_1$Y<br>X$_1$ = S or N | 96 |
| CDR-L2 amino acid sequence (common sequence) | LAS | 97 |
| CDR-L3 amino acid sequence (common sequence) | SRELPRT | 98 |

In certain aspects, an anti-glyco-MUC1 antibody or antigen-binding fragment of the disclosure comprises CDRs comprising the amino acid sequences of any of the CDR combinations set forth in numbered embodiments 3 to 41. Thus, in certain embodiments, an anti-glyco-MUC1 antibody or antigen-binding fragment of the disclosure comprises a CDR-H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:97, and a CDR-L3 comprising the amino acid sequence of SEQ ID NO:98. In some embodiments, CDR-H1 comprises the amino acid sequence of SEQ ID NO: 3, 9, 15, 25, 31, 37, 45, 51, 57, 63, 69, 75, 81, 87, or 93. In some embodiments, CDR-H2 comprises the amino acid sequence of SEQ ID NO: 4, 10, 16, 26, 32, 38, 46, 52, 58, 64, 70, 76, 82, 88, or 94. In some embodiments, CDR-H3 comprises the amino acid sequence of SEQ ID NO: 5, 11, 17, 27, 33, 39, 47, 53, 59, 65, 71, 77, 83, 89, or 95. In some embodiments, CDR-L1 comprises the amino acid sequence of SEQ ID NO:6, 12, 18, 28, 34, 40, 48, 54, 60, 66, 72, 78, 84, 90, or 96. In some embodiments, CDR-L2 comprises the amino acid sequence of SEQ ID NO:7, 13, 19, 29, 35, 41, 49, 55, 61, 67, 73, 79, 85, 91 or 97. In some embodiments, CDR-L3 comprises the amino acid sequence of SEQ ID NO:8, 14, 20, 30, 36, 42, 50, 56, 62, 68, 74, 80, 86, or 92.

In other aspects, an anti-glyco-MUC1 antibody or antigen-binding fragment of the disclosure comprises heavy chain CDRs of SEQ ID NOS:3-5 and light chain CDRs of SEQ ID NOS:6-8. In other aspects, an anti-glyco-MUC1 antibody or antigen-binding fragment of the disclosure comprises heavy chain CDRs of SEQ ID NOS:9-11 and light chain CDRs of SEQ ID NOS:12-14. In other aspects, an anti-glyco-MUC1 antibody or antigen-binding fragment of the disclosure comprises heavy chain CDRs of SEQ ID NOS:15-17 and light chain CDRs of SEQ ID NOS:18-20. In other aspects, an anti-glyco-MUC1 antibody or antigen-binding fragment of the disclosure comprises heavy chain CDRs of SEQ ID NOS:25-27 and light chain CDRs of SEQ ID NOS:28-30. In other aspects, an anti-glyco-MUC1 antibody or antigen-binding fragment of the disclosure comprises heavy chain CDRs of SEQ ID NOS:31-33 and light chain CDRs of SEQ ID NOS:34-36. In other aspects, an anti-glyco-MUC1 antibody or antigen-binding fragment of the disclosure comprises heavy chain CDRs of SEQ ID NOS:37-39 and light chain CDRs of SEQ ID NOS:40-42. In other aspects, an anti-glyco-MUC1 antibody or antigen-binding fragment of the disclosure comprises heavy chain CDRs of SEQ ID NOS:45-47 and light chain CDRs of SEQ ID NOS:48-50. In other aspects, an anti-glyco-MUC1 antibody or antigen-binding fragment of the disclosure comprises heavy chain CDRs of SEQ ID NOS:51-53 and light chain CDRs of SEQ ID NOS:54-56. In other aspects, an anti-glyco-MUC1 antibody or antigen-binding fragment of the disclosure comprises heavy chain CDRs of SEQ ID NOS:57-59 and light chain CDRs of SEQ ID NOS:60-62. In other aspects, an anti-glyco-MUC1 antibody or antigen-binding fragment of the disclosure comprises heavy chain CDRs of SEQ ID NOS:63-65 and light chain CDRs of SEQ ID NOS:66-68. In other aspects, an anti-glyco-MUC1 antibody or antigen-binding fragment of the disclosure comprises heavy chain CDRs of SEQ ID NOS:69-71 and light chain CDRs of SEQ ID NOS:72-74. In other aspects, an anti-glyco-MUC1 antibody or antigen-binding fragment of the disclosure comprises heavy chain CDRs of SEQ ID NOS:75-77 and light chain CDRs of SEQ ID NOS:78-80. In other aspects, an anti-glyco-MUC1 antibody or antigen-binding fragment of the disclosure comprises heavy chain CDRs of SEQ ID NOS:81-83 and light chain CDRs of SEQ ID NOS:84-86. In other aspects, an anti-glyco-MUC1 antibody or antigen-binding fragment of the disclosure comprises heavy chain CDRs of SEQ ID NOS:87-89 and light chain CDRs of SEQ ID NOS:90-92.

The antibodies and antigen-binding fragments of the disclosure can be murine, chimeric, humanized or human.

In further aspects, an anti-glyco-MUC1 antibody or antigen binding fragment of the disclosure competes with an antibody or antigen binding fragment comprising heavy and light chain variable regions of SEQ ID NOS: 1 and 2, respectively. In yet other aspects, the disclosure provides an anti-MUC1 antibody or antigen binding fragment having heavy and light chain variable regions having at least 95%, 98%, 99%, or 99.5% sequence identity of SEQ ID NOS: 1 and 2, respectively.

In yet other aspects, an anti-glyco-MUC1 antibody or antigen binding fragment of the disclosure competes with an antibody or antigen binding fragment comprising heavy and light chain variable regions of SEQ ID NOS: 23 and 24, respectively. In yet other aspects, the disclosure provides an anti-MUC1 antibody or antigen binding fragment having heavy and light chain variable regions having at least 95%, 98%, 99%, or 99.5% sequence identity of SEQ ID NOS: 23 and 24, respectively.

In yet other aspects, an anti-glyco-MUC1 antibody or antigen-binding fragment of the disclosure is a single-chain variable fragment (scFv). An exemplary scFv comprises the heavy chain variable fragment N-terminal to the light chain variable fragment. In some embodiments, the scFv heavy chain variable fragment and light chain variable fragment are covalently bound to a linker sequence of 4-15 amino acids. The scFv can be in the form of a bi-specific T-cell engager or within a chimeric antigen receptor (CAR).

The anti-glyco-MUC1 antibodies and antigen-binding fragments can be in the form of a multimer of a single-chain variable fragment, a bispecific single-chain variable fragment and a multimer of a bispecific single-chain variable fragment. In some embodiments, the multimer of a single chain variable fragment is selected a divalent single-chain variable fragment, a tribody or a tetrabody. In some of these embodiments, the multimer of a bispecific single-chain variable fragment is a bispecific T-cell engager.

Other aspects of the disclosure are drawn to nucleic acids encoding the anti-glyco-MUC1 antibodies and antibody-binding fragments of the disclosure. In some embodiments, the portion of the nucleic acid nucleic acid encoding an anti-glyco-MUC1 antibody or antigen-binding fragment is codon-optimized for expression in a human cell. In certain aspects, the disclosure provides an anti-glyco-MUC1 antibody or antigen binding fragment having heavy and light chain variable regions encoded by a heavy chain nucleotide sequence having at least 95%, 98%, 99%, or 99.5% sequence identity to SEQ ID NO:21 or SEQ ID NO:43 and a light chain nucleotide sequence having at least 95%, 98%, 99%, or 99.5% sequence identity to SEQ ID NO:22 or SEQ ID NO:44. Vectors (e.g., a viral vector such as a lentiviral vector) and host cells comprising the nucleic acids are also within the scope of the disclosure. The heavy and light chains coding sequences can be present on a single vector or on separate vectors.

Yet another aspect of the disclosure is a pharmaceutical composition comprising an anti-glyco-MUC1 antibody, antigen-binding fragment, nucleic acid (or pair of nucleic acids), vector (or pair of vectors) or host cell according to the disclosure, and a physiologically suitable buffer, adjuvant or diluent.

Still another aspect of the disclosure is a method of making a chimeric antigen receptor comprising incubating a cell comprising a nucleic acid or a vector according to the disclosure, under conditions suitable for expression of the coding region and collecting the chimeric antigen receptor.

Another aspect of the disclosure is a method of detecting cancer comprising contacting a cell or tissue sample with an anti-glyco-MUC1 antibody or antigen-binding fragment of the disclosure and detecting whether the antibody is bound to the cell or tissue sample.

Yet another aspect of the disclosure is an anti-glyco-MUC1 antibody or antigen-binding fragment according to the disclosure of the disclosure for use in detecting cancer.

Yet another aspect of the disclosure is a method of treating cancer comprising administering a prophylactically or therapeutically effective amount of an anti-glyco-MUC1 antibody, antigen-binding fragment, nucleic acid, vector, host cell or pharmaceutical composition according to the disclosure to a subject in need thereof.

Yet another aspect of the disclosure is an anti-glyco-MUC1 antibody, antigen-binding fragment, nucleic acid, vector, host cell or pharmaceutical composition according to the disclosure for use in the treatment of cancer.

Yet another aspect of the disclosure is use of an anti-glyco-MUC1 antibody, antigen-binding fragment, nucleic acid, vector, host cell or pharmaceutical composition according to the disclosure for the manufacture of a medicament for the treatment of cancer.

5. BRIEF DESCRIPTION OF THE FIGURES

Figure 1B:
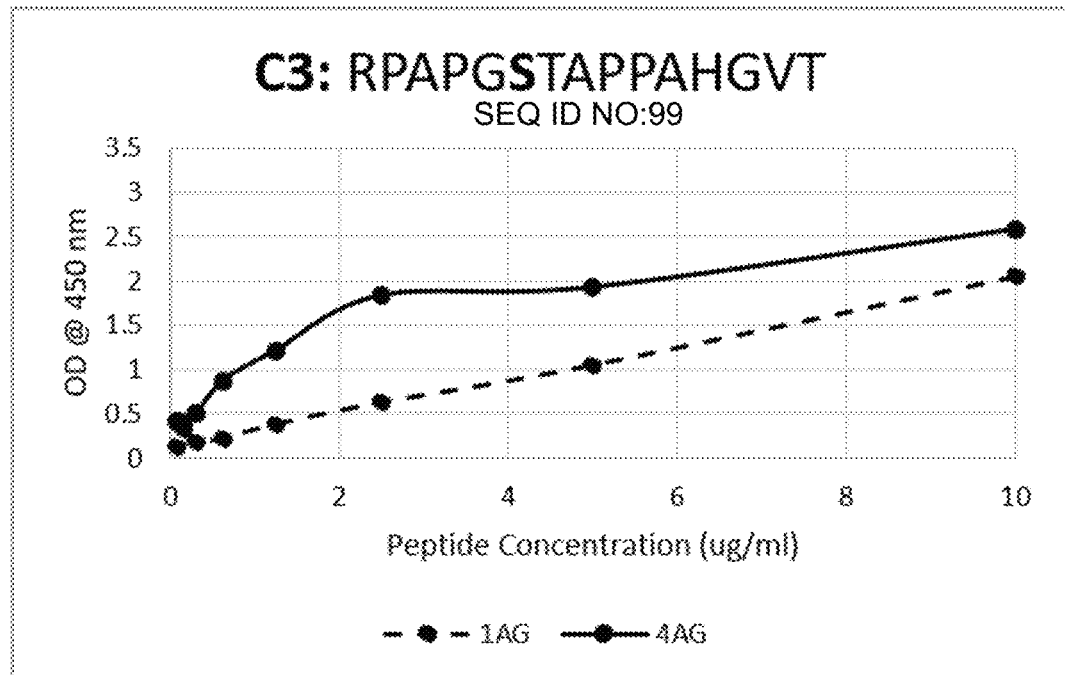
Figure 1C:
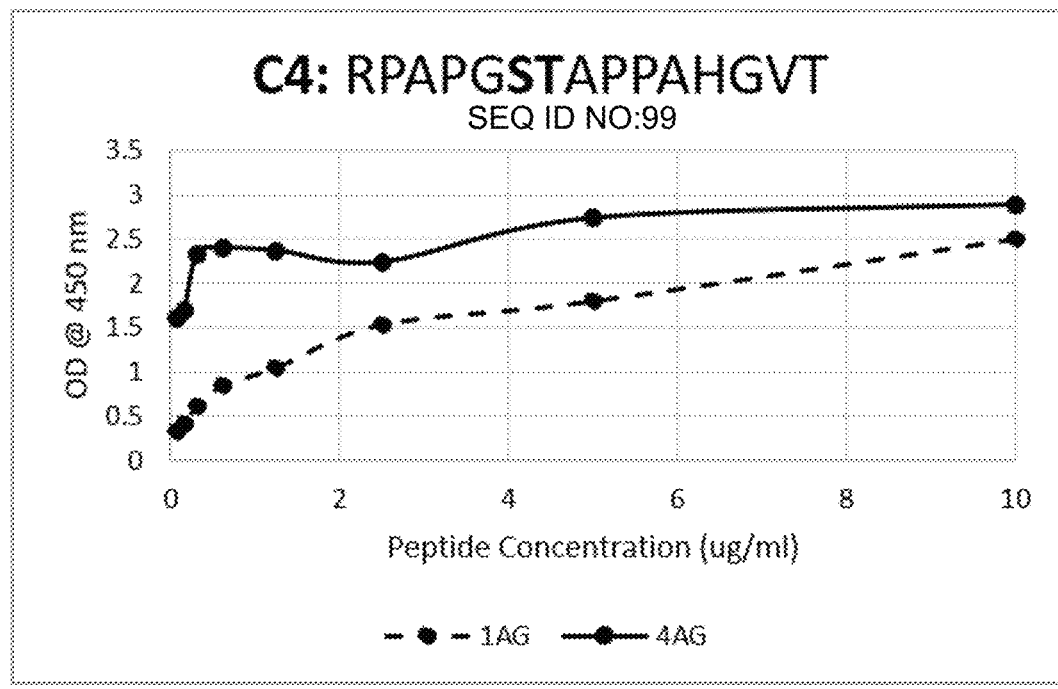
Figure 1D:
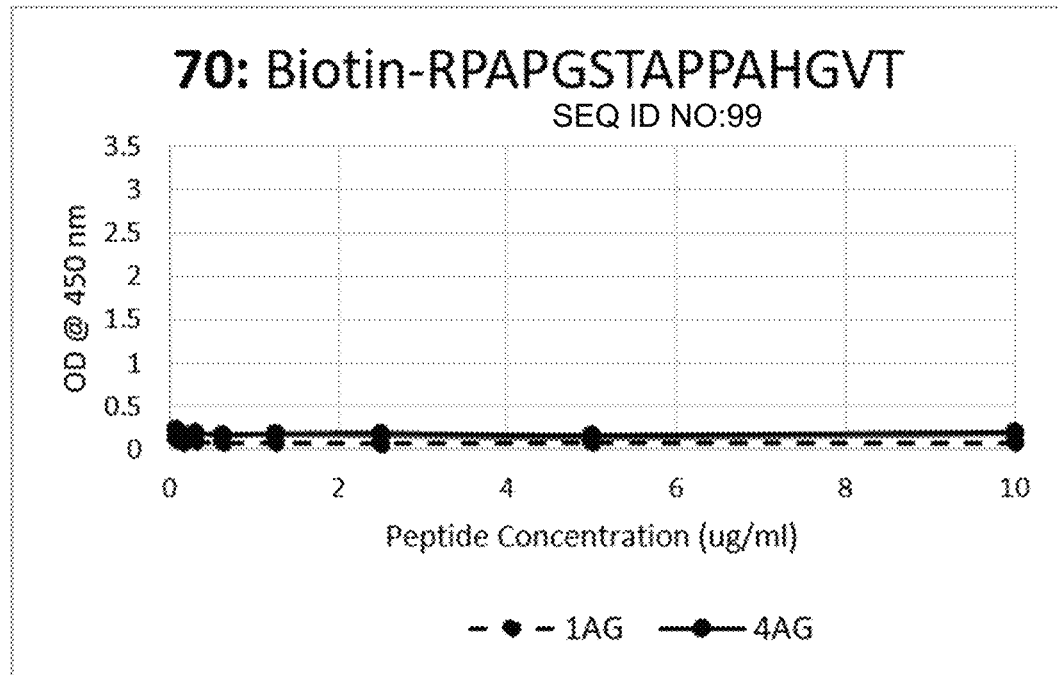
Figure 1E:
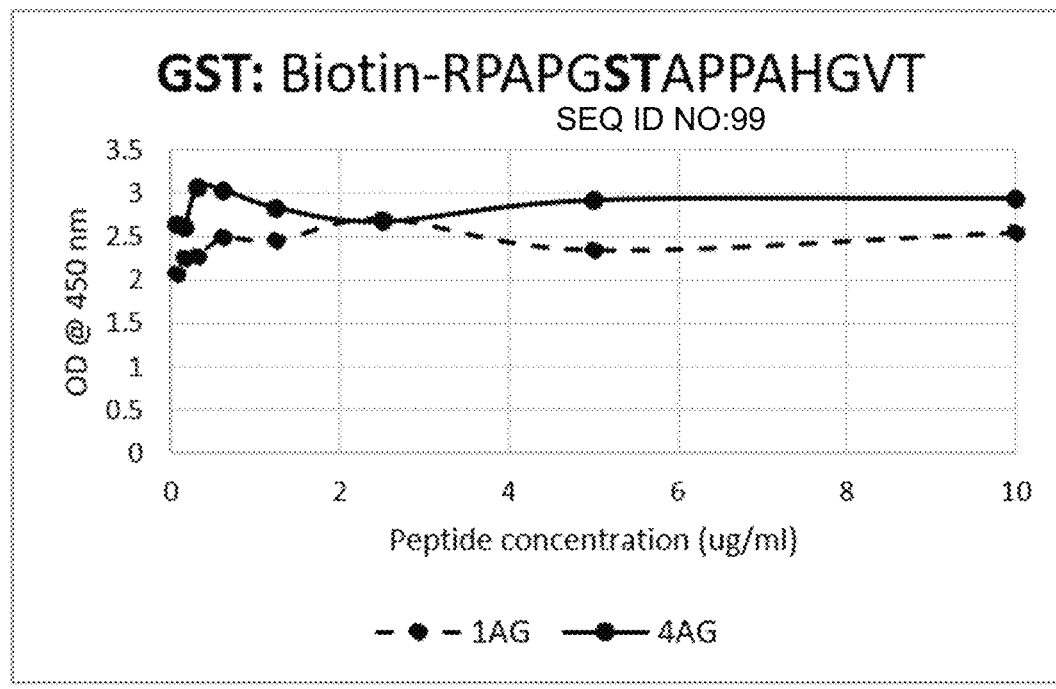
Figure 1F:
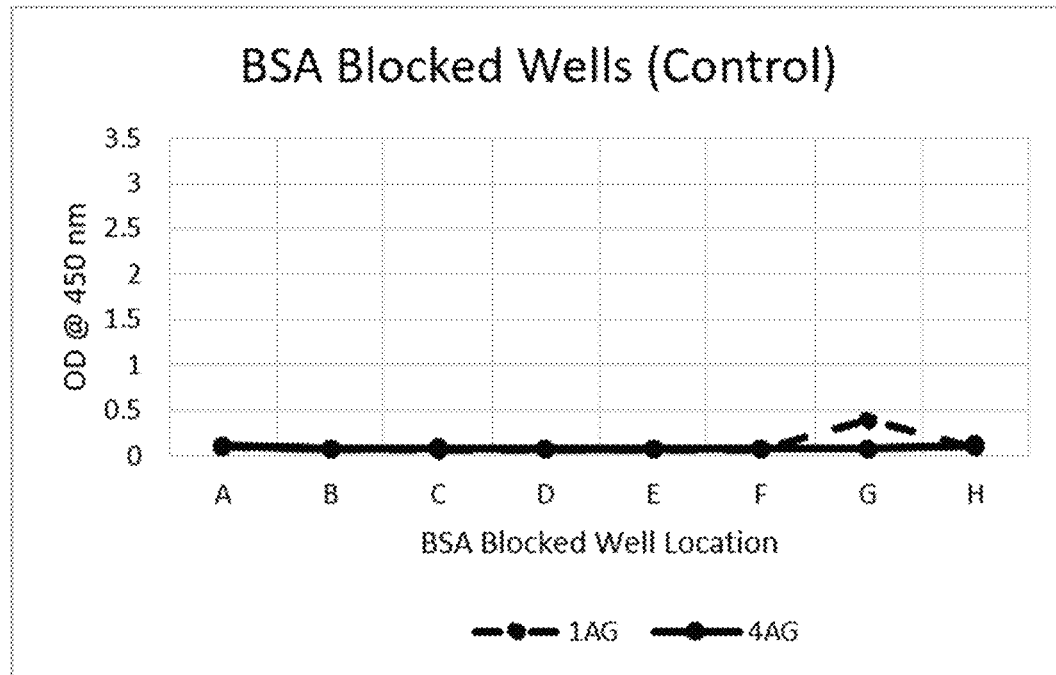

FIGS. 1A-EF: Results of ELISA assay showing specificity of binding of 1AG and 4AG to glycosylated and non-glycosylated MUC1 peptides. FIG. 1A: peptide C2; FIG. 1B: peptide C3; FIG. 1C: peptide C4; FIG. 1D: peptide 70; FIG. 1E: GST; FIG. 1F: BSA blocked wells (control).

Figure 2A:
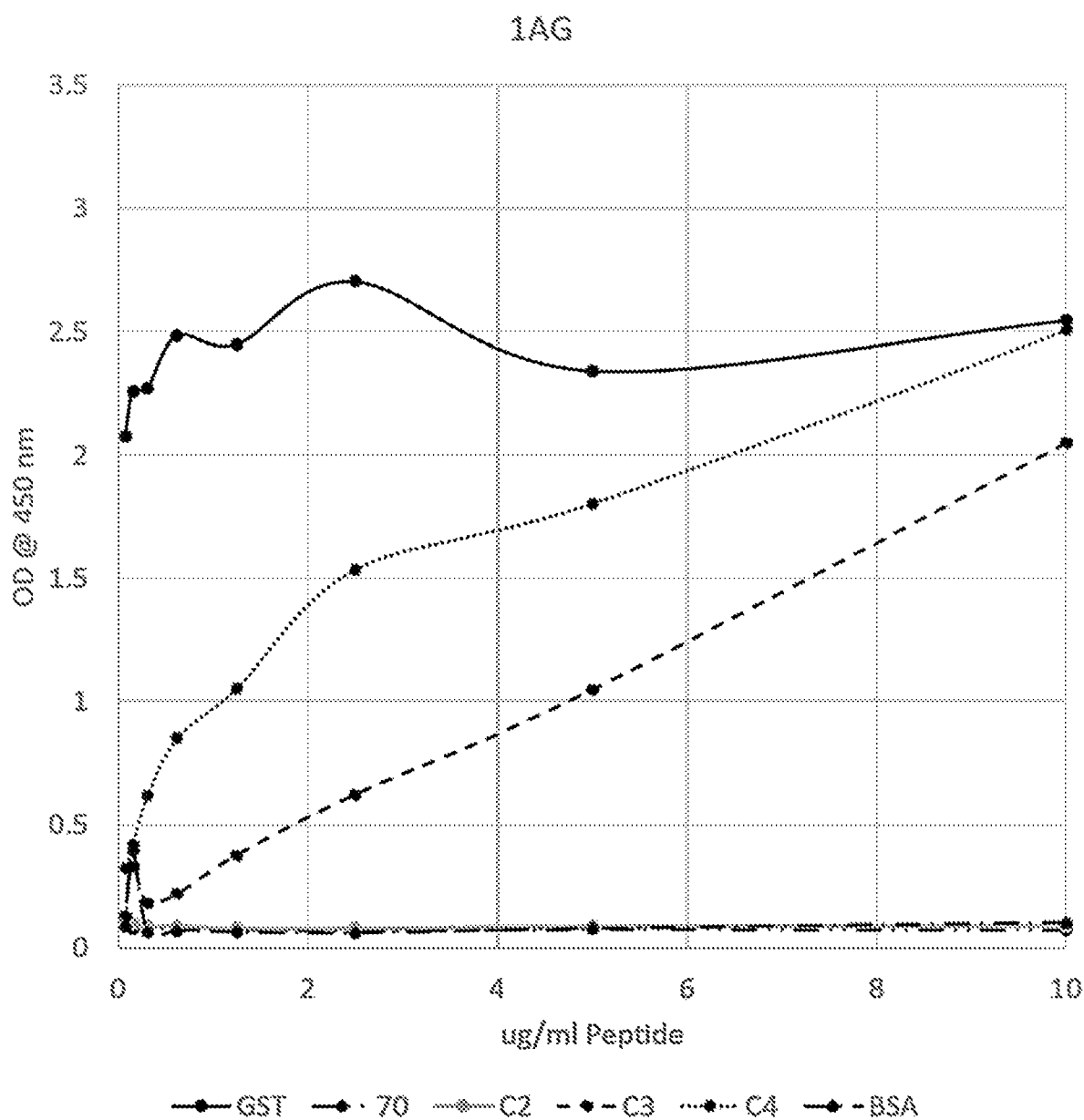
Figure 2B:
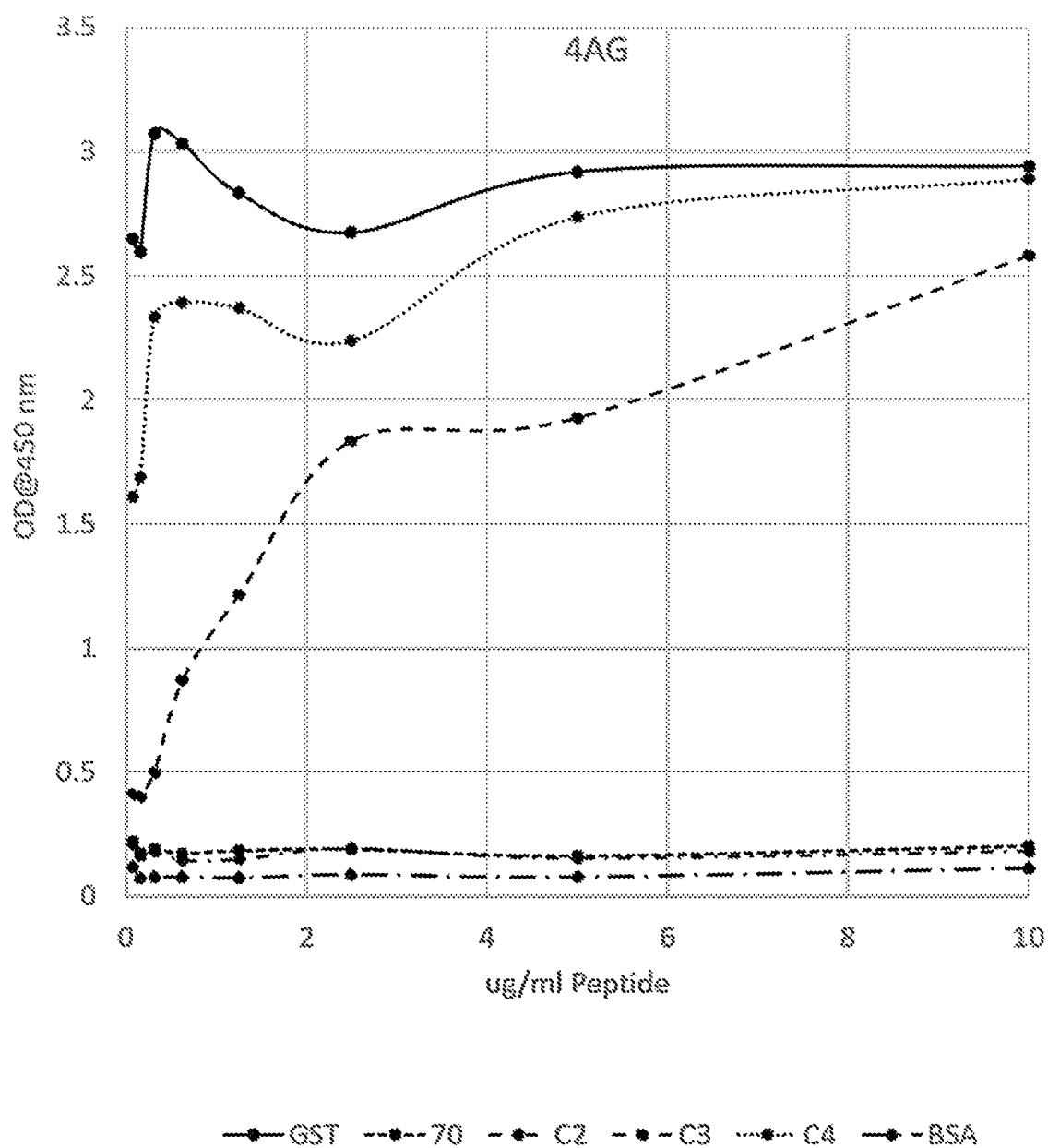

FIG. 2: Results of ELISA assay showing specificity of binding of 1AG (FIG. 2A) and 4AG (FIG. 2B) to different glycosylated and non-glycosylated MUC1 peptides.

Figure 3:
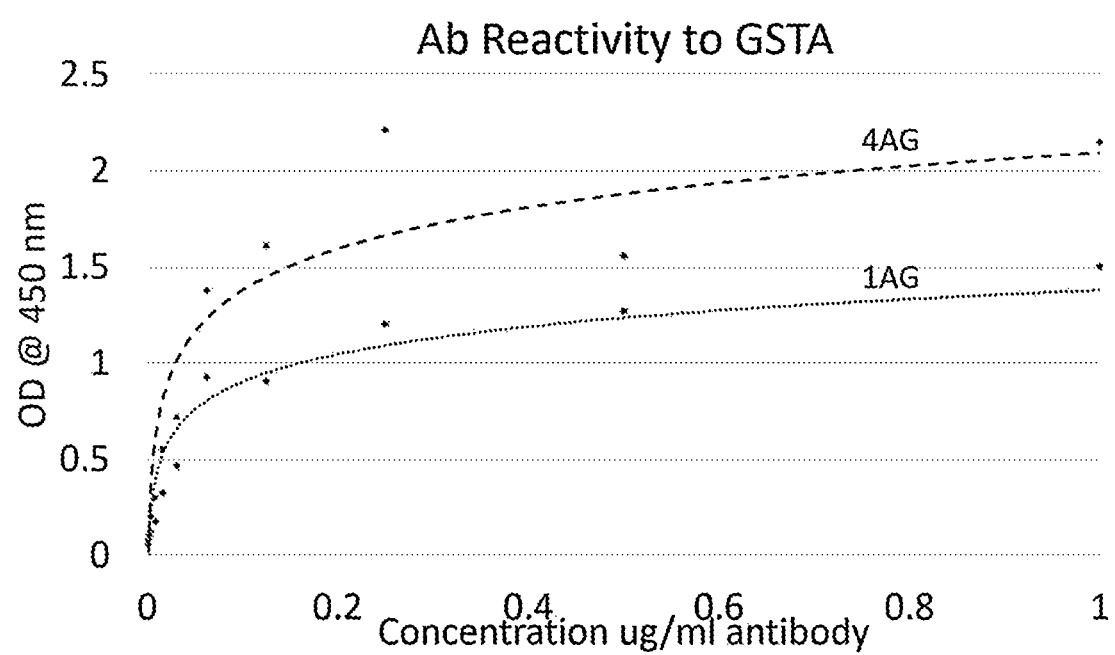

FIG. 3: Results of antibody titration assay with 1AG and 4AG against antigen GSTA.

Figure 4:
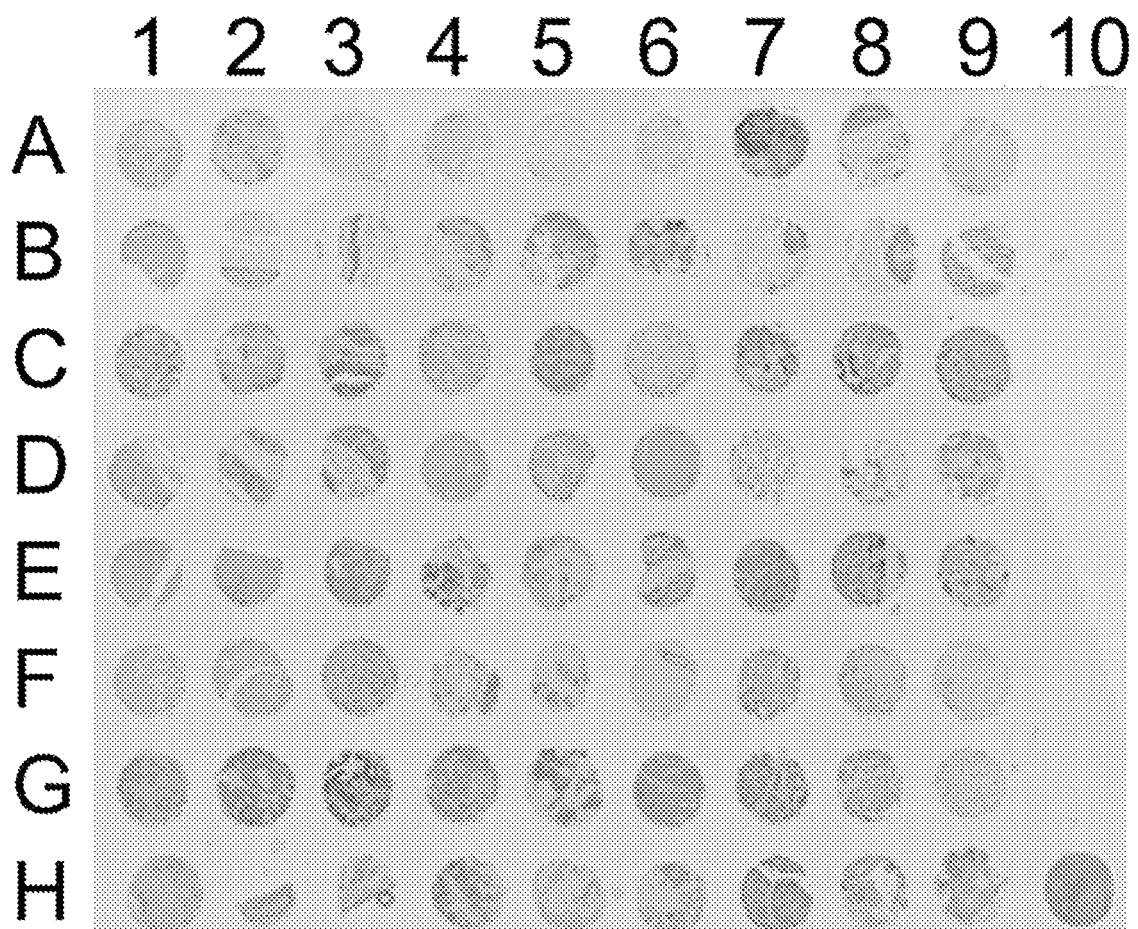

FIG. 4: Results of immunohistochemistry screening of antibody 1AG with tumor microarray BCN721a.

Figure 5:
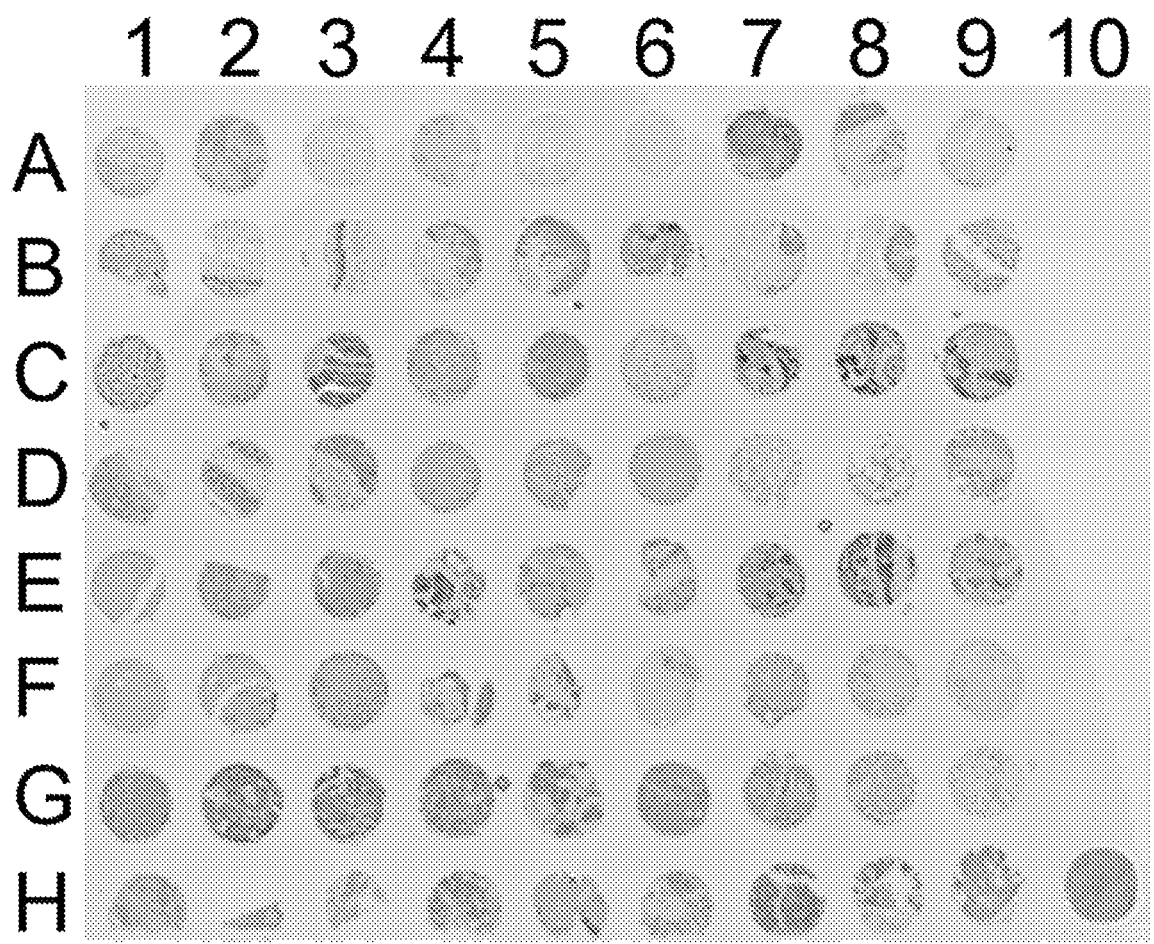

FIG. 5: Results of immunohistochemistry screening of antibody 4AG with tumor microarray BCN721a.

Figure 6:
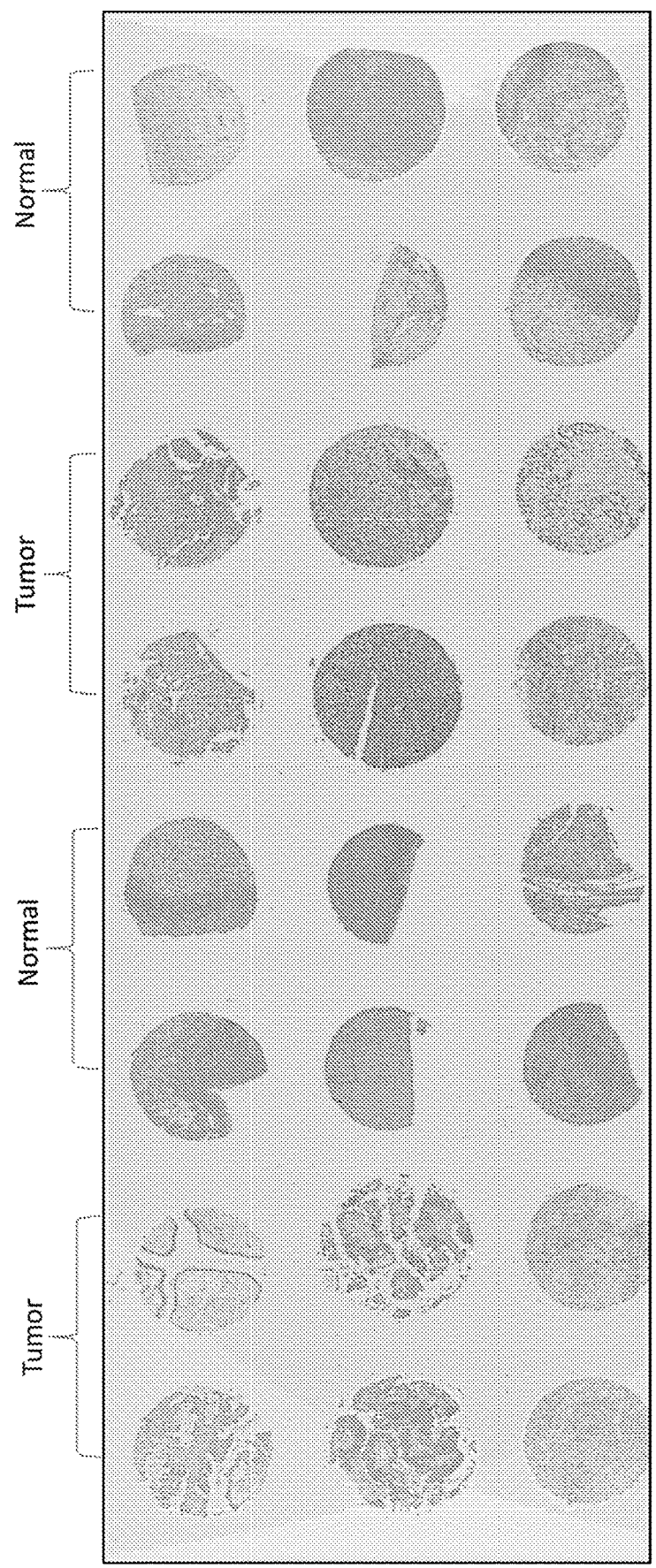

FIG. 6: Results of immunohistochemistry screening of antibody 1AG with tumor microarray OV241c.

Figure 7:
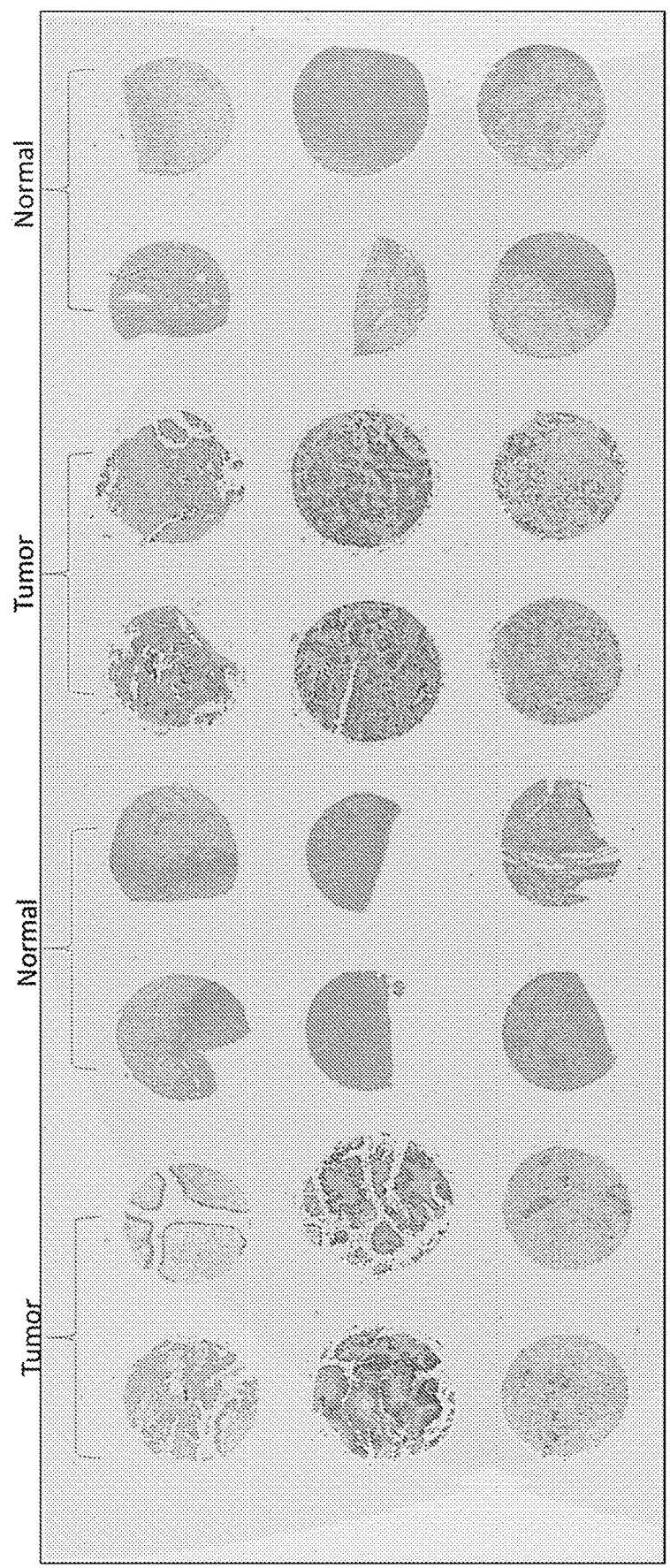

FIG. 7: Results of immunohistochemistry screening of antibody 4AG with tumor microarray OV241c.

Figure 8:
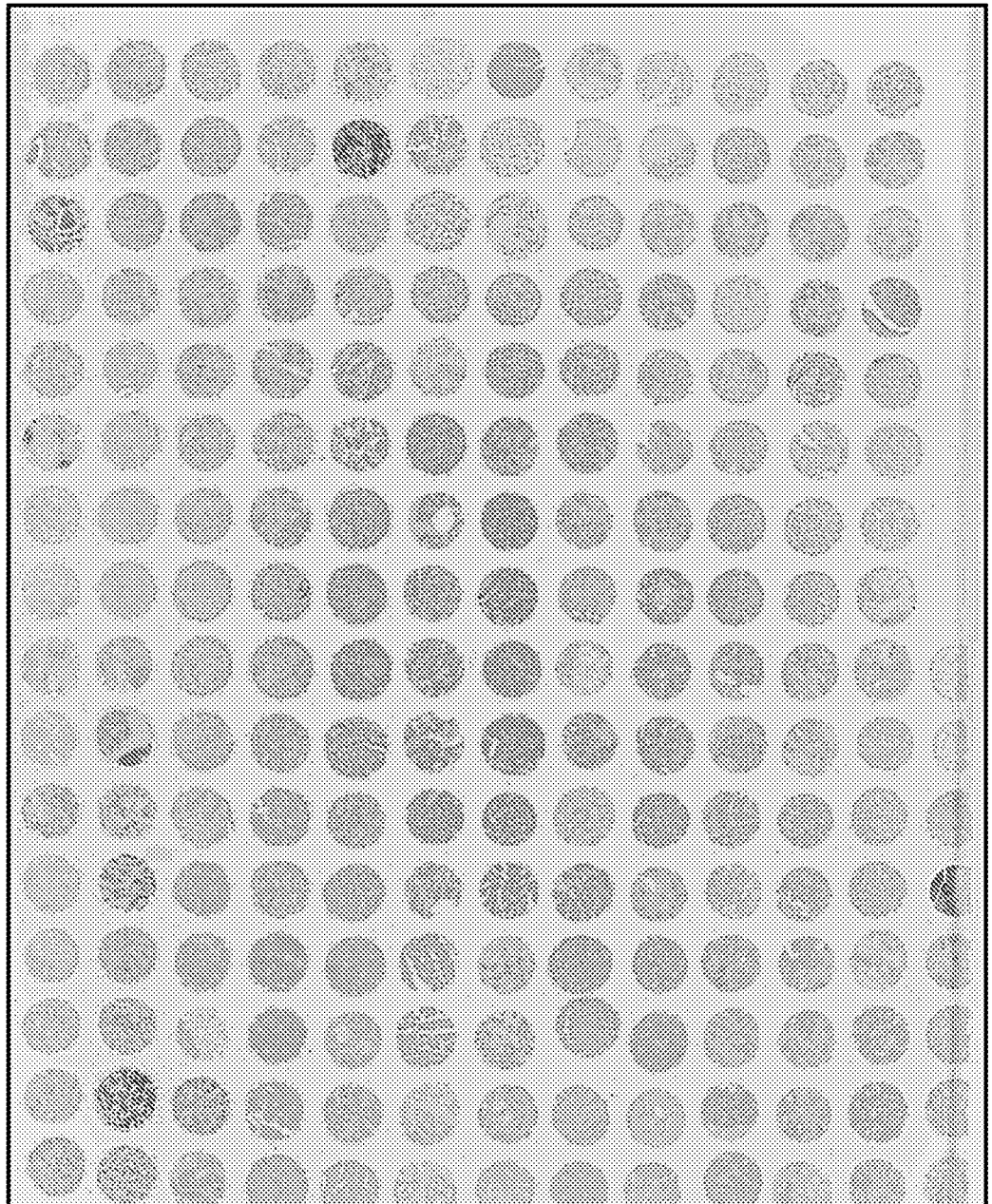

FIG. 8: Results of immunohistochemistry screening of antibody 1AG with tumor microarray BC000119.

Figure 9:
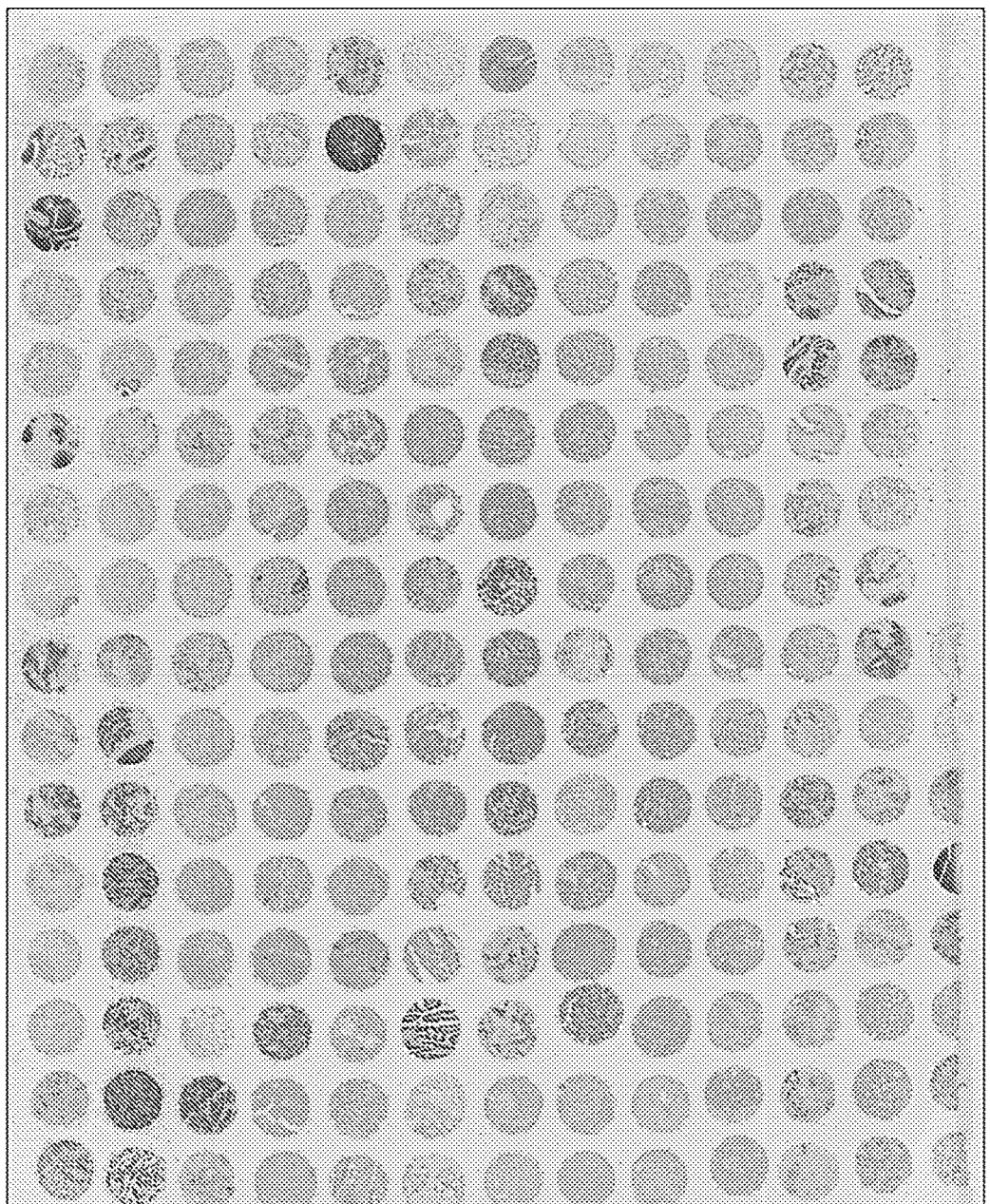

FIG. 9: Results of immunohistochemistry screening of antibody 4AG with tumor microarray BC000119.

Figure 10:
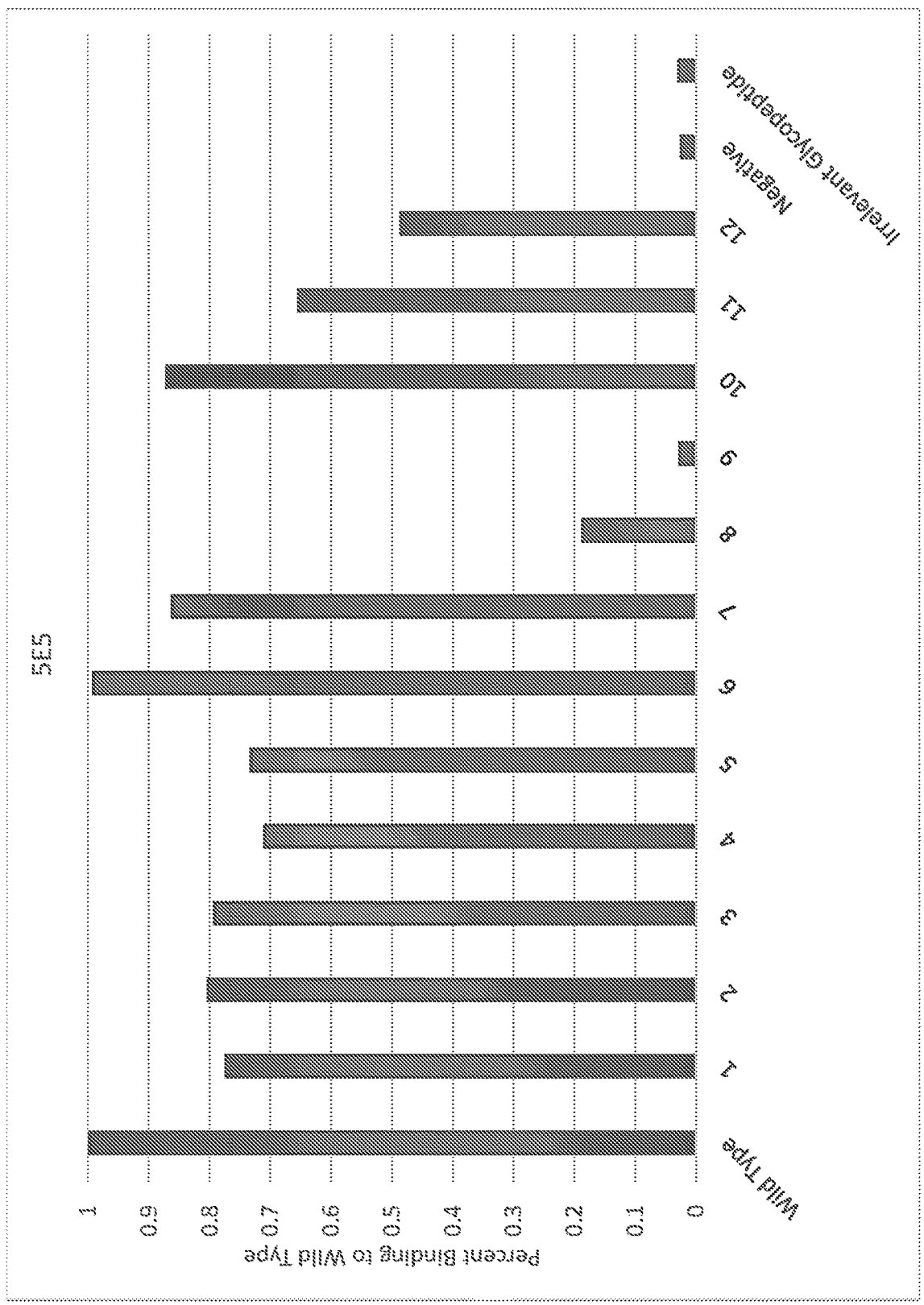

FIG. 10: Results of alanine scanning with antibody 5E5.

Figure 11:
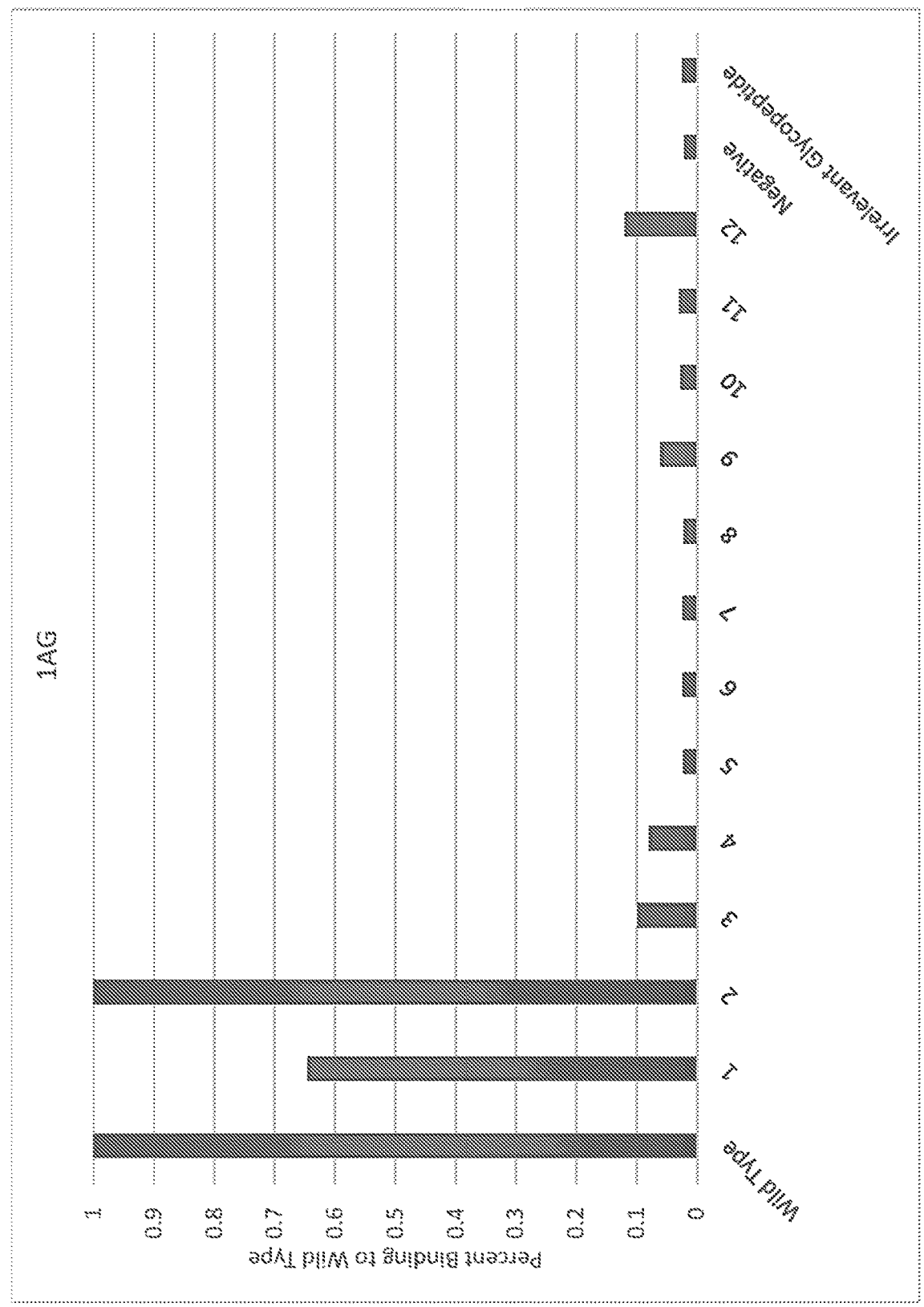

FIG. 11: Results of alanine scanning with antibody 1AG.

Figure 12:
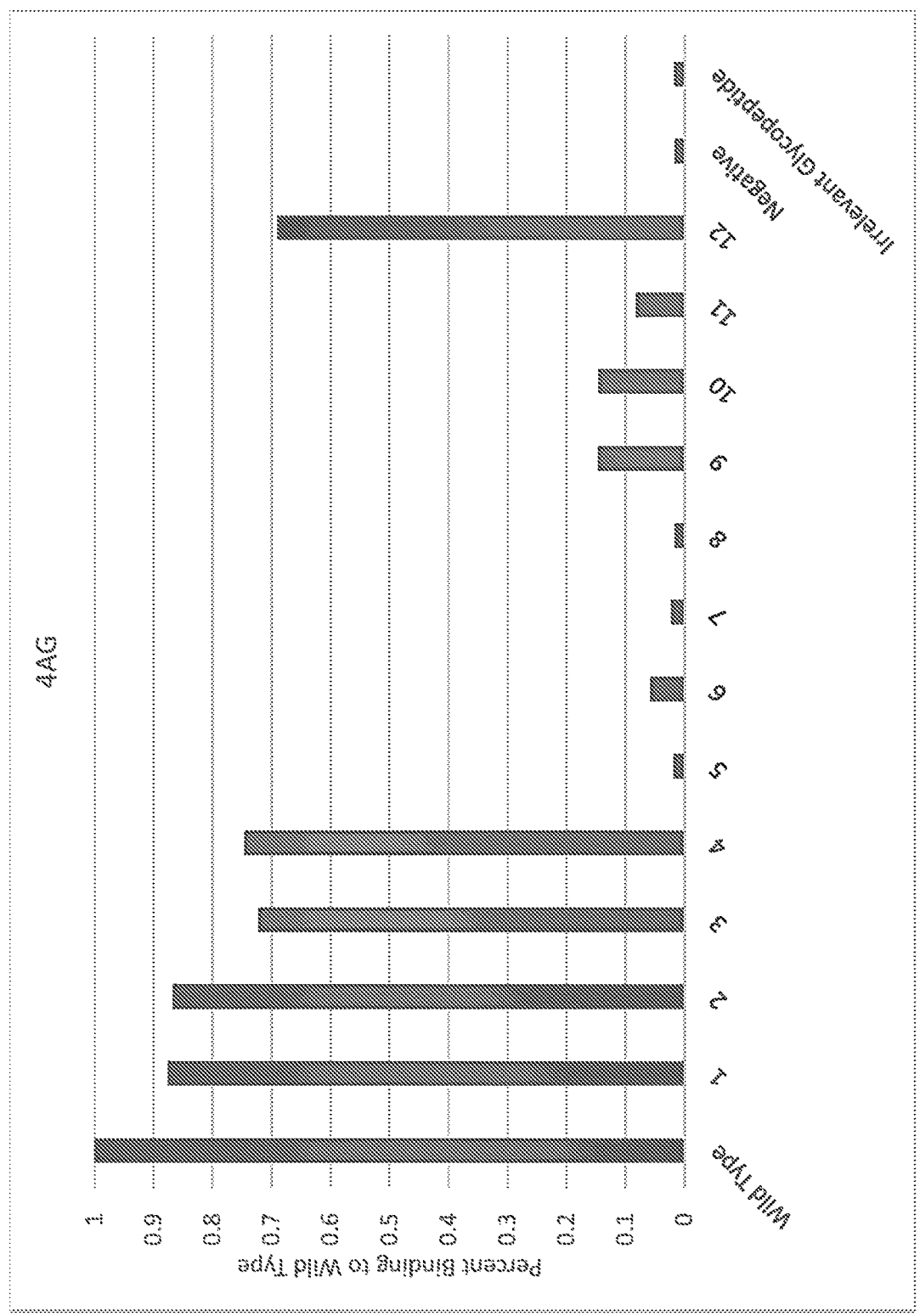

FIG. 12: Results of alanine scanning with antibody 4AG.

6. DETAILED DESCRIPTION

6.1 Antibodies

The disclosure provides novel antibodies that are directed to a glycoform of MUC1 present on tumor cells. These are exemplified by the antibodies 1AG and 4AG. 1AG and 4AG were identified in a screen for antibodies that bind to a glycosylated 15-mer present in MUC1, RPAPGSTAP-PAHGVT (SEQ ID NO:99), glycosylated with GalNAc on the serine and threonine residues shown in bold underlined text so as to mimic the glycosylation pattern of MUC1 present on tumor cells.

The anti-glyco-MUC1 antibodies of the disclosure, exemplified by antibodies 1AG and 4AG, are useful as tools in cancer diagnosis and therapy.

Thus, in certain aspects, the disclosure provides antibodies and antigen binding fragments that bind to a glycoform of MUC1 present on tumor cells (referred to herein as "glyco-MUC1"), and preferably to the 15-mer peptide RPAPGSTAPPAHGVT (SEQ ID NO:99) glycosylated with GalNAc on the serine and threonine residues shown in bold underlined text.

The anti-glyco-MUC1 antibodies of the disclosure may be polyclonal, monoclonal, genetically engineered, and/or otherwise modified in nature, including but not limited to chimeric antibodies, humanized antibodies, human antibodies, primatized antibodies, single chain antibodies, bispecific antibodies, dual-variable domain antibodies, etc. In various embodiments, the antibodies comprise all or a portion of a constant region of an antibody. In some embodiments, the constant region is an isotype selected from: IgA (e.g., $IgA_1$ or $IgA_2$), IgD, IgE, IgG (e.g., $IgG_1$, $IgG_2$, $IgG_3$ or $IgG_4$), and IgM. In specific embodiments, the anti-glyco-MUC1 antibodies of the disclosure comprise an $IgG_1$ constant region isotype.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-glyco-MUC1 antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

"Human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

Anti-glyco-MUC1 antibodies of the disclosure include both full-length (intact) antibody molecules, as well as antigen-binding fragments that are capable of binding glyco-MUC1. Examples of antigen-binding fragments include by way of example and not limitation, Fab, Fab', F (ab')$_2$, Fv fragments, single chain Fv fragments and single domain fragments.

A Fab fragment contains the constant domain of the light chain (CL) and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_1$ fragments lack the Fc fragment of intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antigen-binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

"Single domain antibodies" are composed of single $V_H$ or $V_L$ domains which exhibit sufficient affinity to glyco-MUC1. In a specific embodiment, the single domain antibody is a camelized antibody (See, e.g., Riechmann, 1999, Journal of Immunological Methods 231:25-38).

The anti-glyco-MUC1 antibodies of the disclosure may also be bispecific and other multiple specific antibodies. Bispecific antibodies are monoclonal, often human or humanized, antibodies that have binding specificities for two different epitopes on the same or different antigen. In the present disclosure, one of the binding specificities can be directed towards glyco-MUC1, the other can be for any other antigen, e.g., for a cell-surface protein, receptor, receptor subunit, tissue-specific antigen, virally derived protein, virally encoded envelope protein, bacterially derived protein, or bacterial surface protein, etc. In certain preferred embodiments, the bispecific and other multispecific anti-glyco-MUC1 antibodies and antigen binding fragments specifically bind to a second MUC1 epitope, an epitope on another protein co-expressed on cancer cells with MUC1, or an epitope on another protein presented on a different cell, such as an activated T cell. Bispecific antibodies of the disclosure include IgG format bispecific antibodies and single chain-based bispecific antibodies.

IgG format bispecific antibodies of the disclosure can be any of the various types of IgG format bispecific antibodies known in the art, such as quadroma bispecific antibodies, "knobs-in-holes" bispecific antibodies, CrossMab bispecific antibodies, charge paired bispecific antibodies, common light chain bispecific antibodies, one-arm single-chain Fab-immunoglobulin gamma bispecific antibodies, disulfide stabilized Fv bispecific antibodies, DuetMabs, controlled Fab-arm exchange bispecific antibodies, strand-exchange engineered domain body bispecific antibodies, two-arm leucine zipper heterodimeric monoclonal bispecific antibodies, κλ-body bispecific antibodies, dual variable domain bispecific antibodies, and cross-over dual variable domain bispecific antibodies. See, e.g., Köhler and Milstein, 1975, Nature 256:495-497; Milstein and Cuello, 1983, Nature 305:537-40; Ridgway et al., 1996, Protein Eng. 9:617-621; Schaefer et al., 2011, Proc Natl Acad Sci USA 108:11187-92; Gunasekaran et al., 2010, J Biol Chem 285:19637-46; Fischer et al., 2015 Nature Commun 6:6113; Schanzer et al., 2014, J Biol Chem 289:18693-706; Metz et al., 2012 Protein Eng Des Sel 25:571-80; Mazor et al., 2015 MAbs 7:377-89; Labrijn et al., 2013 Proc Natl Acad Sci USA 110:5145-50; Davis et al., 2010 Protein Eng Des Sel 23:195-202; Wranik et al., 2012, J Biol Chem 287:43331-9; Gu et al., 2015, PLoS One 10(5):e0124135; Steinmetz et al., 2016, MAbs 8(5): 867-78; Klein et al., 2016, mAbs, 8(6):1010-1020; Liu et al., 2017, Front. Immunol. 8:38; and Yang et al., 2017, Int. J. Mol. Sci. 18:48, which are incorporated herein by reference in their entireties.

In some embodiments, the bispecific antibodies of the disclosure are CrossMabs. The CrossMab technology is described in detail in WO 2009/080251, WO 2009/080252, WO 2009/080253, WO 2009/080254, WO 2013/026833, WO 2016/020309, and Schaefer et al., 2011, Proc Natl Acad Sci USA 108:11187-92, which are incorporated herein by reference in their entireties. Briefly, the CrossMab technology is based on a domain crossover between heavy and light chains within one Fab-arm of a bispecific IgG, which promotes correct chain association. A CrossMab bispecific antibody of the disclosure can be a "CrossMab$^{FAB}$" antibody, in which the heavy and light chains of the Fab portion of one arm of a bispecific IgG antibody are exchanged. In other embodiments, a CrossMab bispecific antibody of the disclosure can be a "CrossMab$^{VH-VL}$" antibody, in which the only the variable domains of the heavy and light chains of the Fab portion of one arm of a bispecific IgG antibody are exchanged. In yet other embodiments, a CrossMab bispecific antibody of the disclosure can be a "CrossMab$^{CH1-CL}$" antibody, in which only the constant domains of the heavy and light chains of the Fab portion of one arm of a bispecific IgG antibody are exchanged. CrossMab$^{CH1-CL}$ antibodies, in contrast to CrossMab$^{FAB}$ and CrossMab$^{VH-VL}$, do not have predicted side products and, therefore, in some embodiments CrossMab$^{CH1-CL}$ bispecific antibodies are preferred. See, Klein et al., 2016, mAbs, 8(6):1010-1020.

In some embodiments, the bispecific antibodies of the disclosure are controlled Fab-arm exchange bispecific antibodies. Methods for making Fab-arm exchange bispecific antibodies are described in PCT Publication No. WO2011/131746 and Labrijn et al., 2014 Nat Protoc. 9(10):2450-63, incorporated herein by reference in their entireties. Briefly, controlled Fab-arm exchange bispecific antibodies can be made by separately expressing two parental IgG1s containing single matching point mutations in the CH3 domain, mixing the parental IgG1s under redox conditions in vitro to enable recombination of half-molecules, and removing the reductant to allow reoxidation of interchain disulfide bonds, thereby forming the bispecific antibodies.

Bispecific antibodies of the disclosure can comprise an Fc domain composed of a first and a second subunit. In one embodiment, the Fc domain is an IgG Fc domain. In a particular embodiment, the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat EU index numbering), particularly the amino acid substitution S228P. Unless otherwise specified herein, numbering of amino acid residues in an Fc domain or constant region is according to the EU numbering system, also called the EU index, as described in Kabat et al., 1991, Sequences of Proteins of Immunological Interest, 5th Ed. Public Health Service, National Institutes of Health, Bethesda, MD. This amino acid substitution reduces in vivo Fab arm exchange of IgG$_4$ antibodies (see Stubenrauch et al., 2010, Drug Metabolism and Disposition 38:84-91). In a further particular embodiment, the Fc domain is a human Fc domain. In an even more particular embodiment, the Fc domain is a human IgG₁ Fc domain. An exemplary sequence of a human IgG₁ Fc region is given in SEQ ID NO:42.

In particular embodiments, the Fc domain comprises a modification promoting the association of the first and the second subunit of the Fc domain. The site of most extensive protein-protein interaction between the two subunits of a human IgG Fc domain is in the CH3 domain. Thus, in one embodiment said modification is in the CH3 domain of the Fc domain.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain. The knob-into-hole technology is described e.g. in U.S. Pat. Nos. 5,731,168; 7,695,936; Ridgway et al., 1996, Prot Eng 9:617-621, and Carter, J, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis.

In a specific such embodiment, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numbering according to Kabat EU index). In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second subunit of the Fc domain.

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

Typically, the same one or more amino acid substitution is present in each of the two subunits of the Fc domain. In one embodiment, the one or more amino acid substitution reduces the binding affinity of the Fc domain to an Fc receptor. In one embodiment, the one or more amino acid substitution reduces the binding affinity of the Fc domain to an Fc receptor by at least 2-fold, at least 5-fold, or at least 10-fold.

In one embodiment, the Fc domain comprises an amino acid substitution at a position selected from the group of E233, L234, L235, N297, P331 and P329 (numberings according to Kabat EU index). In a more specific embodiment, the Fc domain comprises an amino acid substitution at a position selected from the group of L234, L235 and P329 (numberings according to Kabat EU index). In some embodiments, the Fc domain comprises the amino acid substitutions L234A and L235A (numberings according to Kabat EU index). In one such embodiment, the Fc domain is an IgG₁ Fc domain, particularly a human IgG₁ Fc domain. In one embodiment, the Fc domain comprises an amino acid substitution at position P329. In a more specific embodiment, the amino acid substitution is P329A or P329G, particularly P329G (numberings according to Kabat EU index). In one embodiment, the Fc domain comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain comprises amino acid substitutions at positions P329, L234 and L235 (numberings according to Kabat EU index). In more particular embodiments, the Fc domain comprises the amino acid mutations L234A, L235A and P329G ("P329G LALA", "PGLALA" or "LALAPG"). Specifically, in particular embodiments, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index). In one such embodiment, the Fc domain is an IgG$_1$ Fc domain, particularly a human IgG$_1$ Fc domain.

Single chain-based bispecific antibodies of the disclosure can be any of the various types of single chain-based bispecific antibodies known in the art, such as bispecific T-cell engagers (BiTEs), diabodies, tandem diabodies (tandabs), dual-affinity retargeting molecules (DARTs), and bispecific killer cell engagers. See, e.g., Löffler et al., 2000, Blood 95:2098-103; Holliger et al., 1993, Proc Natl Acad Sci USA, 90:6444-8; Kipriyanov et al., 1999, Mol Biol 293:41-56; Johnson et al., 2010, Mol Biol 399:436-49; Wiernik et al., 2013, Clin Cancer Res 19:3844-55; Liu et al., 2017, Front. Immunol. 8:38; and Yang et al., 2017, Int. J. Mol. Sci. 18:48, which are incorporated herein by reference in their entireties.

In some embodiments, the bispecific antibodies of the disclosure are bispecific T-cell engagers (BiTEs). BiTEs are single polypeptide chain molecules that having two antigen-binding domains, one of which binds to a T-cell antigen and the second of which binds to an antigen present on the surface of a target (See, PCT Publication WO 05/061547; Baeuerle et al., 2008, Drugs of the Future 33: 137-147; Bargou, et al., 2008, Science 321:974-977, incorporated herein by reference in their entireties). Thus, the BiTEs of the disclosure have an antigen binding domain that binds to a T-cell antigen, and a second antigen binding domain that is directed towards glyco-MUC1.

In some embodiments, the bispecific antibodies of the disclosure are dual-affinity retargeting molecules (DARTs). DARTs comprise at least two polypeptide chains that associate (especially through a covalent interaction) to form at least two epitope binding sites, which may recognize the same or different epitopes. Each of the polypeptide chains of a DART comprise an immunoglobulin light chain variable region and an immunoglobulin heavy chain variable region, but these regions do not interact to form an epitope binding site. Rather, the immunoglobulin heavy chain variable region of one (e.g., the first) of the DART polypeptide chains interacts with the immunoglobulin light chain variable region of a different (e.g., the second) DART™ polypeptide chain to form an epitope binding site. Similarly, the immunoglobulin light chain variable region of one (e.g., the first) of the DART polypeptide chains interacts with the immunoglobulin heavy chain variable region of a different (e.g., the second) DART polypeptide chain to form an epitope binding site. DARTs may be monospecific, bispecific, trispecific, etc., thus being able to simultaneously bind one, two, three or more different epitopes (which may be of the same or of different antigens). DARTs may additionally be monovalent, bivalent, trivalent, tetravalent, pentavalent, hexavalent, etc., thus being able to simultaneously bind one, two, three, four, five, six or more molecules. These two attributes of DARTs (i.e., degree of specificity and valency may be combined, for example to produce bispecific antibodies (i.e., capable of binding two epitopes) that are tetravalent (i.e., capable of binding four sets of epitopes), etc. DART molecules are disclosed in PCT Publications WO 2006/113665, WO 2008/157379, and WO 2010/080538, which are incorporated herein by reference in their entireties.

In some embodiments of the bispecific antibodies of the disclosure, one of the binding specificities is directed towards glyco-MUC1, and the other is directed to an antigen expressed on immune effector cells. The term "immune effector cell" or "effector cell" as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte. Recruitment of effector cells to aberrant cells means that immune effector cells are brought in close vicinity to the aberrant target cells such that the effector cells can directly kill, or indirectly initiate the killing of the aberrant cells that they are recruited to. In order to avoid non specific interactions it is preferred that the bispecific antibodies of the disclosure specifically recognize antigens on immune effector cells that are at least over-expressed by these immune effector cells compared to other cells in the body. Target antigens present on immune effector cells may include CD3, CD8, CD16, CD25, CD28, CD64, CD89, NKG2D and NKp46. Preferably, the antigen on immune effector cells is CD3 expressed on T cells.

As used herein, "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. The most preferred antigen on an immune effector cell is the CD3 epsilon chain. This antigen has been shown to be very effective in recruiting T cells to aberrant cells. Hence, a bispecific antibody of the disclosure preferably specifically recognizes CD3 epsilon. The amino acid sequence of human CD3 epsilon is shown in UniProt (www.uniprot.org) accession no. P07766 (version 144), or NCBI (www.ncbi.nlm.nih.gov/) RefSeq NP_000724.1. The amino acid sequence of cynomolgus [*Macaca fascicularis*]CD3 epsilon is shown in NCBI GenBank no. BAB71849.1. For human therapeutic use, bispecific antibodies in which the CD3-binding domain specifically binds to human CD3 (e.g., the human CD3 epsilon chain) are used. For preclinical testing in non-human animals and cell lines, bispecific antibodies in which the CD3-binding domain specifically binds to the CD3 in the species utilized for the preclinical testing (e.g., cynomolgus CD3 for primate testing) can be used.

As used herein, a binding domain that "specifically binds to" or "specifically recognizes" a target antigen from a particular species does not preclude the binding to or recognition of the antigen from other species, and thus encompasses antibodies in which one or more of the binding domains have inter-species cross-reactivity. For example, a CD3-binding domain that "specifically binds to" or "specifically recognizes" human CD3 may also bind to or recognize cyomolgus CD3, and vice versa.

In some embodiments, a bispecific antibody of the disclosure can compete with monoclonal antibody H2C (described in PCT publication no. WO2008/119567) for binding an epitope of CD3. In other embodiments, a bispecific antibody of the disclosure can compete with monoclonal antibody V9 (described in Rodrigues et al., 1992, Int J Cancer Suppl 7:45-50 and U.S. Pat. No. 6,054,297) for binding an epitope of CD3. In yet other embodiments, a bispecific antibody of the disclosure can compete with monoclonal antibody FN18 (described in Nooij et al., 1986, Eur J Immunol 19:981-984) for binding an epitope of CD3. In yet other embodiments, a bispecific antibody of the disclosure can compete with monoclonal antibody SP34 (described in Pessano et al., 1985, EMBO J 4:337-340) for binding an epitope of CD3.

The anti-glyco-MUC1 antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

The anti-glyco-MUC1 antibodies or binding fragments may be antibodies or fragments whose sequences have been modified to alter at least one constant region-mediated biological effector function. For example, in some embodiments, an anti-glyco-MUC1 antibody may be modified to reduce at least one constant region-mediated biological effector function relative to the unmodified antibody, e.g., reduced binding to the Fc receptor (FcγR). FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

The anti-glyco-MUC1 antibody or binding fragments described herein include antibodies and/or binding fragments that have been modified to acquire or improve at least one constant region-mediated biological effector function relative to an unmodified antibody, e.g., to enhance FcγR interactions (See, e.g., US 2006/0134709). For example, an anti-glyco-MUC1 antibody of the disclosure can have a constant region that binds FcγRIIA, FcγRIIB and/or FcγRIIIA with greater affinity than the corresponding wild type constant region.

Thus, antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (shown in FIG. 4 of U.S. Pat. No. 5,834,597) in which residue 236 is deleted and residues 234, 235 and 237 (using EU numbering) are substituted with alanines. Another exemplary ADCC lowering variant comprises amino acid mutations L234A, L235A and P329G ("P329G LALA"). The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

In some embodiments, the anti-glyco-MUC1 antibodies of the disclosure have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1, 6-fucosyltransferase, an enzyme necessary for fucosylation of polypeptides.

In some embodiments, the anti-glyco-MUC1 antibodies or binding fragments include bisected oligosaccharides, e.g., in which a biantennary oligosaccharide attached to an Fc domain is bisected by GlcNAc. Such variants may have reduced fucosylation and/or improved ADCC function as described above. Examples of such antibody variants are described, e.g., in Umana et al., 1999, Nat Biotechnol 17:176-180; Ferrara et al., 2006, Biotechn Bioeng 93: 851-861; WO 99/54342; WO 2004/065540; and WO 2003/011878.

In yet another aspect, the anti-glyco-MUC1 antibodies or binding fragments include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-glyco-MUC1 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which is incorporated herein by reference. Such mutations increase binding to FcRn, which protects the antibody from degradation and increases its half-life.

In yet other aspects, an anti-glyco-MUC1 antibody of antigen-binding fragment of the disclosure has one or more amino acids inserted into one or more of its hypervariable regions, for example as described in Jung and Pluckthun, 1997, Protein Engineering 10:9, 959-966; Yazaki et al., 2004, Protein Eng. Des Sel. 17(5):481-9. Epub 2004-8-17; and U.S. Pat. App. No. 2007/0280931.

In yet other aspects, particularly useful for diagnostic applications, an anti-glyco-MUC1 antibody of antigen-binding fragment of the disclosure is attached to a detectable moiety. Detectable moieties include a radioactive moiety, a colorimetric molecule, a fluorescent moiety, a chemiluminescent moiety, an antigen, an enzyme, a detectable bead (such as a magnetic or electrodense (e.g., gold) bead), or a molecule that binds to another molecule (e.g., biotin or streptavidin)).

Radioisotopes or radionuclides may include $^3$H, $^{14}$C $^{15}$N, $^{35}$S, $^{90}$Y, $^{99}$Tc, $^{111}$In, $^{125}$I, $^{131}$I.

Fluorescent labels may include rhodamine, lanthanide phosphors, fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine.

Enzymatic labels may include horseradish peroxidase, p galactosidase, luciferase, alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase.

Chemiluminescent labels or chemiluminescers, such as isoluminol, luminol and the dioxetanes.

Other detectable moieties include molecules such as biotin, digoxygenin or 5-bromodeoxyuridine.

In certain aspects, an anti-glyco-MUC1 antibody or antigen binding fragment of the disclosure competes with 1AG or an antibody or antigen binding fragment comprising heavy and light chain variable regions of 1AG (SEQ ID NOS:1 and 2, respectively).

In other aspects, an anti-glyco-MUC1 antibody or antigen binding fragment of the disclosure competes with 4AG or an antibody or antigen binding fragment comprising heavy and light chain variable regions of 4AG (SEQ ID NOS:23 and 24, respectively).

The competition can be assayed on cells that express the glyco-MUC1 epitope bound by 1AG or 4AG or on a glycosylated MUC1 peptide containing the epitope bound by 1AG or 4AG, e.g., the 15-mer peptide RPAPG$\underline{S}$TAPPAHGVT (SEQ ID NO:99) glycosylated with GalNAc on the serine and threonine residues shown in bold and underlined text. Cells that do not express the epitope or unglycosylated peptides can be used as controls.

Cells on which a competition assay can be carried out include but are not limited to the breast cancer cell lines MCF7 or T47D and recombinant cells that are engineered to express the glyco-MUC1 epitope. In one non-limiting example, CHO ldlD cells, which lack the UDP-Gal/GalNAc epimerase and are deficient in GalNAc O-glycosylation and galactosylation in the absence of exogenous addition of GalNAc and Gal, respectively, are engineered to express MUC1 and grown in the absence or presence of GalNAc, the latter yielding cells expressing the Tn glycoform of MUC1 to which 1AG and 4AG bind. Cells expressing the unglycosylated form of MUC1 can be used as a negative control.

Assays for competition include, but are not limited to, a radioactive material labeled immunoassay (RIA), an enzyme-linked immunosorbent assay (ELISA), a sandwich ELISA, fluorescence activated cell sorting (FACS) assays and surface plasmon resonance (e.g., Biacore) assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing glyco-MUC1 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("conc$_{80\%}$") under the assay conditions (e.g., a specified density of cells) is first determined, and a competition assay carried out with 10×conc$_{80\%}$ of unlabeled test antibody and conc$_{80\%}$ of labeled reference antibody.

The inhibition can be expressed as an inhibition constant, or $K_i$, which is calculated according to the following formula:

$$K_i = IC_{50}/(1+[\text{reference } Ab \text{ concentration}]/K_d),$$

where IC$_{50}$ is the concentration of test antibody that yields a 50% reduction in binding of the reference antibody and $K_d$ is the dissociation constant of the reference antibody, a measure of its affinity for glyco-MUC1. Antibodies that compete with anti-glyco-MUC1 antibodies disclosed herein can have a $K_i$ from 10 pM to 10 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

In one example of a competition assay, the glycosylated MUC1 15-mer peptide is adhered onto a solid surface, e.g., a microwell plate, by contacting the plate with a solution of the peptide (e.g., at a concentration of 1 µg/mL in PBS over night at 4° C.). The plate is washed (e.g., 0.1% Tween 20 in PBS) and blocked (e.g., in Superblock, Thermo Scientific, Rockford, IL). A mixture of sub-saturating amount of biotinylated 1AG or 4AG (e.g., at a concentration of 80 ng/mL) and unlabeled 1AG or 4AG (the "reference" antibody) or competing anti-glyco-MUC1 antibody (the "test" antibody) antibody in serial dilution (e.g., at a concentration of 2.8 µg/mL, 8.3 µg/mL, or 25 µg/mL) in ELISA buffer (e.g., 1% BSA and 0.1% Tween 20 in PBS) is added to wells and plates are incubated for 1 hour with gentle shaking. The plate is washed, 1 µg/mL HRP-conjugated Streptavidin diluted in ELISA buffer is added to each well and the plates incubated for 1 hour. Plates are washed and bound antibodies were detected by addition of substrate (e.g., TMB, Biofx Laboratories Inc., Owings Mills, MD). The reaction is terminated by addition of stop buffer (e.g., Bio FX Stop Reagents, Biofx Laboratories Inc., Owings Mills, MD) and the absorbance is measured at 650 nm using microplate reader (e.g., VERSAmax, Molecular Devices, Sunnyvale, CA).

Variations on this competition assay can also be used to test competition between 1AG or 4AG and another anti-glyco-MUC1 antibody. For example, in certain aspects, the anti-glyco-MUC1 antibody is used as a reference antibody and 1AG or 4AG is used as a test antibody. Additionally, instead of glycosylated MUC1 15-mer peptide, membrane-bound glyco-MUC1 expressed on cell surface (for example on the surface of one of the cell types mentioned above) in culture can be used. Generally, about $10^4$ to $10^6$ transfectants, e.g., about $10^5$ transfectants, are used. Other formats for competition assays are known in the art and can be employed.

In various embodiments, an anti-glyco-MUC1 antibody of the disclosure reduces the binding of labeled 1AG or 4AG by at least 40%, by at least 50%, by at least 60%, by at least 70%, by at least 80%, by at least 90%, or by a percentage ranging between any of the foregoing values (e.g., an anti-glyco-MUC1 antibody of the disclosure reduces the binding of labeled 1AG or 4AG by 50% to 70%) when the anti-glyco-MUC1 antibody is used at a concentration of 0.08 µg/mL, 0.4 µg/mL, 2 µg/mL, 10 µg/mL, 50 µg/mL, 100 µg/mL or at a concentration ranging between any of the foregoing values (e.g., at a concentration ranging from 2 µg/mL to 10 µg/mL).

In other embodiments, 1AG or 4AG reduces the binding of a labeled anti-glyco-MUC1 antibody of the disclosure by at least 40%, by at least 50%, by at least 60%, by at least 70%, by at least 80%, by at least 90%, or by a percentage ranging between any of the foregoing values (e.g., 1AG or 4AG reduces the binding of a labeled an anti-glyco-MUC1 antibody of the disclosure by 50% to 70%) when 1AG or 4AG is used at a concentration of 0.4 µg/mL, 2 µg/mL, 10 µg/mL, 50 µg/mL, 250 µg/mL or at a concentration ranging between any of the foregoing values (e.g., at a concentration ranging from 2 µg/mL to 10 µg/mL).

In the foregoing assays, the 1AG or 4AG antibody can be replaced by any antibody or antigen-binding fragment comprising the CDRs or the heavy and light chain variable regions of 1AG or 4AG, such as a humanized or chimeric counterpart of 1AG or 4AG.

In certain aspects, an anti-glyco-MUC1 antibody or antigen-binding fragment of the disclosure has an epitope which is the same or similar to the epitope of 1AG or 4AG. The epitope of an anti-glyco-MUC1 antibody or antigen-binding fragment of the disclosure can be characterized by performing alanine scanning, for example as described in Example 9. Example 9 describes a library of 12 glycopeptides (SEQ ID NOs:106-117), each varying from the MUC1 peptide

```
                                            (SEQ ID NO: 105)
          TAPPAHGVTSAPDTRPAPGSTAPPAHGV
``` by an alanine point mutation at one of positions 13-24 (or, where the MUC1 peptide has an alanine, by a glycine point mutation). By measuring an antibody or antigen binding fragment's binding to each of the peptides by ELISA, the antibody or antigen binding fragment's epitope can be mapped.

In some embodiments, an anti-glyco-MUC1 antibody or antigen-binding fragment of the disclosure binds to the peptide

```
                                             (SEQ ID NO: 99)
                      RPAPGSTAPPAHGVT
``` with a greater affinity than to the peptide

```
                                            (SEQ ID NO: 113)
          TAPPAHGVTSAPDTRPAPGATAPPAHGV
``` as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide

```
                                             (SEQ ID NO: 99)
                      RPAPGSTAPPAHGVT
``` with a greater affinity than to both of the peptides

```
                                            (SEQ ID NO: 113)
          TAPPAHGVTSAPDTRPAPGATAPPAHGV
``` and

```
                                            (SEQ ID NO: 114)
          TAPPAHGVTSAPDTRPAPGSAAPPAHGV
``` as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide

```
                                             (SEQ ID NO: 99)
                      RPAPGSTAPPAHGVT
``` with a greater affinity than to each of the peptides

```
                                            (SEQ ID NO: 113)
          TAPPAHGVTSAPDTRPAPGATAPPAHGV,
```

```
                                            (SEQ ID NO: 114)
          TAPPAHGVTSAPDTRPAPGSAAPPAHGV,
``` and

```
                                            (SEQ ID NO: 115)
          TAPPAHGVTSAPDTRPAPGSTGPPAHGV
``` as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide

```
                                             (SEQ ID NO: 99)
                      RPAPGSTAPPAHGVT
``` with a greater affinity than to each of the peptides

```
                                            (SEQ ID NO: 113)
          TAPPAHGVTSAPDTRPAPGATAPPAHGV,
```

```
                                            (SEQ ID NO: 114)
          TAPPAHGVTSAPDTRPAPGSAAPPAHGV,
```

```
                                            (SEQ ID NO: 115)
          TAPPAHGVTSAPDTRPAPGSTGPPAHGV,
``` and

```
                                            (SEQ ID NO: 116)
          TAPPAHGVTSAPDTRPAPGSTAAPAHGV
``` as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide (SEQ ID NO: 99)
           RPAPGSTAPPAHGVT with a greater affinity than to each of the peptides (SEQ ID NO: 113)
   TAPPAHGVTSAPDTRPAPGATAPPAHGV, (SEQ ID NO: 114)
   TAPPAHGVTSAPDTRPAPGSAAPPAHGV, (SEQ ID NO: 115)
   TAPPAHGVTSAPDTRPAPGSTGPPAHGV, (SEQ ID NO: 116)
   TAPPAHGVTSAPDTRPAPGSTAAPAHGV, and (SEQ ID NO: 117)
   TAPPAHGVTSAPDTRPAPGSTAPAAHGV as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide (SEQ ID NO: 99)
           RPAPGSTAPPAHGVT with a greater affinity than to each of the peptides

SEQ ID NO: 112)
   TAPPAHGVTSAPDTRPAPASTAPPAHGV, (SEQ ID NO: 113)
   TAPPAHGVTSAPDTRPAPGATAPPAHGV and (SEQ ID NO: 114)
   TAPPAHGVTSAPDTRPAPGSAAPPAHGV as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide (SEQ ID NO: 99)
           RPAPGSTAPPAHGVT with a greater affinity than to each of the peptides (SEQ ID NO: 111)
   TAPPAHGVTSAPDTRPAAGSTAPPAHGV,

SEQ ID NO: 112)
   TAPPAHGVTSAPDTRPAPASTAPPAHGV, (SEQ ID NO: 113)
   TAPPAHGVTSAPDTRPAPGATAPPAHGV and (SEQ ID NO: 114)
   TAPPAHGVTSAPDTRPAPGSAAPPAHGV, as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide (SEQ ID NO: 99)
           RPAPGSTAPPAHGVT with a greater affinity than to each of the peptides (SEQ ID NO: 110)
   TAPPAHGVTSAPDTRPGPGSTAPPAHGV, (SEQ ID NO: 111)
   TAPPAHGVTSAPDTRPAAGSTAPPAHGV,

SEQ ID NO: 112)
   TAPPAHGVTSAPDTRPAPASTAPPAHGV, (SEQ ID NO: 113)
   TAPPAHGVTSAPDTRPAPGATAPPAHGV and (SEQ ID NO: 114)
   TAPPAHGVTSAPDTRPAPGSAAPPAHGV as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide (SEQ ID NO: 99)
           RPAPGSTAPPAHGVT with a greater affinity than to each of the peptides (SEQ ID NO: 110)
   TAPPAHGVTSAPDTRPGPGSTAPPAHGV,

TAPPAHGVTSAPDTRPAAGSTAPPAHGV,     (SEQ ID NO: 111)

TAPPAHGVTSAPDTRPAPASTAPPAHGV,    (SEQ ID NO: 112)

TAPPAHGVTSAPDTRPAPGATAPPAHGV     (SEQ ID NO: 113)

TAPPAHGVTSAPDTRPAPGSAAPPAHGV,    (SEQ ID NO: 114)

and

TAPPAHGVTSAPDTRPAPGSTGPPAHGV     (SEQ ID NO: 115)

as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide

RPAPGSTAPPAHGVT     (SEQ ID NO: 99)

with a greater affinity than to each of the peptides

TAPPAHGVTSAPDTRPGPGSTAPPAHGV,    (SEQ ID NO: 110)

TAPPAHGVTSAPDTRPAAGSTAPPAHGV,    (SEQ ID NO: 111)

TAPPAHGVTSAPDTRPAPASTAPPAHGV,    (SEQ ID NO: 112)

TAPPAHGVTSAPDTRPAPGATAPPAHGV,    (SEQ ID NO: 113)

TAPPAHGVTSAPDTRPAPGSAAPPAHGV,    (SEQ ID NO: 114)

and

TAPPAHGVTSAPDTRPAPGSTGPPAHGV,    (SEQ ID NO: 115)

and

TAPPAHGVTSAPDTRPAPGSTAAPAHGV     (SEQ ID NO: 116)

as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide

RPAPGSTAPPAHGVT     (SEQ ID NO: 99)

with a greater affinity than to each of the peptide

TAPPAHGVTSAPDTRAAPGSTAPPAHGV,    (SEQ ID NO: 109)

TAPPAHGVTSAPDTRPGPGSTAPPAHGV,    (SEQ ID NO: 110)

TAPPAHGVTSAPDTRPAAGSTAPPAHGV,    (SEQ ID NO: 111)

TAPPAHGVTSAPDTRPAPASTAPPAHGV,    (SEQ ID NO: 112)

TAPPAHGVTSAPDTRPAPGATAPPAHGV     (SEQ ID NO: 113)

and

TAPPAHGVTSAPDTRPAPGSAAPPAHGV     (SEQ ID NO: 114)

as measured by ELISA, wherein serine and threonine residues shown with bold and underlined text indicate residues glycosylated with GalNAc.

In some embodiments, an anti-glyco-MUC1 antibody or antigen-binding fragment of the disclosure binds to the peptide

RPAPGSTAPPAHGVT     (SEQ ID NO: 99)

with a greater affinity than to each of the peptides

TAPPAHGVTSAPDTAPAPGSTAPPAHGV,    (SEQ ID NO: 108)

TAPPAHGVTSAPDTRAAPGSTAPPAHGV,    (SEQ ID NO: 109)

TAPPAHGVTSAPDTRPGPGSTAPPAHGV,    (SEQ ID NO: 110)

TAPPAHGVTSAPDTRPAAGSTAPPAHGV,    (SEQ ID NO: 111)

TAPPAHGVTSAPDTRPAPASTAPPAHGV,    (SEQ ID NO: 112)

TAPPAHGVTSAPDTRPAPGATAPPAHGV (SEQ ID NO: 113)

and

TAPPAHGVTSAPDTRPAPGSAAPPAHGV (SEQ ID NO: 114)

as measured by ELISA, wherein serine and threonine residues shown with bold and underlined text indicate residues glycosylated with GalNAc.

In certain aspects, an anti-glyco-MUC1 antibody or antigen-binding fragment of the disclosure comprises heavy and/or light chain variable sequences (or encoded by the nucleotide sequences) set forth in Table 1A or Table 1B. In other aspects, an anti-glyco-MUC1 antibody or antigen-binding fragment of the disclosure comprises heavy and/or light chain CDR sequences (or encoded by the nucleotide sequences) set forth in Table 1A, Table 1B, Table 1C, Table 1D, Table 1E, Table 2A, Table 2B, Table 2C, Table 3A, or Table 3B. The framework sequences for such anti-glyco-MUC1 antibody and antigen-binding fragment can be the native murine framework sequences of the VH and VL sequences set forth in Table 1A or Table 1B or can be non-native (e.g., humanized or human) framework sequences.

In yet other aspects, the disclosure provides an anti-MUC1 antibody or antigen binding fragment having heavy and light chain variable regions having at least 95%, 98%, 99%, or 99.5% sequence identity of SEQ ID NOS: 1 and 2, respectively.

In yet other aspects, the disclosure provides an anti-MUC1 antibody or antigen binding fragment having heavy and light chain variable regions having at least 95%, 98%, 99%, or 99.5% sequence identity of SEQ ID NOS: 23 and 24, respectively.

In yet other aspects, an anti-glyco-MUC1 antibody or antigen-binding fragment of the disclosure is a single-chain variable fragment (scFv). An exemplary scFv comprises the heavy chain variable fragment N-terminal to the light chain variable fragment. In some embodiments, the scFv heavy chain variable fragment and light chain variable fragment are covalently bound to a linker sequence of 4-15 amino acids. The scFv can be in the form of a bi-specific T-cell engager or within a chimeric antigen receptor (CAR).

6.2 Antibody-Drug Conjugates

Another aspect of the disclosure concerns antibody drug conjugates (ADCs) including the anti-glyco-MUC1 antibodies and antigen-binding fragments of the disclosure. The ADCs generally comprise an anti-glyco-MUC1 antibody and/or binding fragment as described herein having one or more cytotoxic and/or cytostatic agents linked thereto by way of one or more linkers. In specific embodiments, the ADCs are compounds according to structural formula (I):

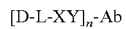

or salts thereof, where each "D" represents, independently of the others, a cytotoxic and/or cytostatic agent ("drug"); each "L" represents, independently of the others, a linker; "Ab" represents an anti-glyco-MUC1 antigen binding domain, such as an anti-glyco-MUC1 antibody or binding fragment described herein; each "XY" represents a linkage formed between a functional group $R^x$ on the linker and a "complementary" functional group $R^y$ on the antibody, and n represents the number of drugs linked to, or drug-to-antibody ratio (DAR), of the ADC.

Specific embodiments of the various antibodies (Ab) that can comprise the ADCs include the various embodiments of anti-glyco-MUC1 antibodies and/or binding fragments described above.

In some specific embodiments of the ADCs and/or salts of structural formula (I), each D is the same and/or each L is the same.

Specific embodiments of cytotoxic and/or cytostatic agents (D) and linkers (L) that can comprise the anti-glyco-MUC1 ADCs of the disclosure, as well as the number of cytotoxic and/or cytostatic agents linked to the ADCs, are described in more detail below.

6.2.1. Cytotoxic and/or Cytostatic Agents

The cytotoxic and/or cytostatic agents may be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, radionuclides, alkylating agents, topoisomerase I inhibitors, topoisomerase II inhibitors, DNA intercalating agents (e.g., groove binding agents such as minor groove binders), RNA/DNA antimetabolites, cell cycle modulators, kinase inhibitors, protein synthesis inhibitors, histone deacetylase inhibitors, mitochondria inhibitors, and antimitotic agents.

Specific non-limiting examples of agents within certain of these various classes are provided below.

Alkylatinq Agents: asaley ((L-Leucine, N—[N-acetyl-4-[bis-(2-chloroethyl)amino]-DL-phenylalanyl]-, ethylester; NSC 167780; CAS Registry No. 3577897)); AZQ ((1,4-cyclohexadiene-1,4-dicarbamic acid, 2,5-bis(1-aziridinyl)-3,6-dioxo-, diethyl ester; NSC 182986; CAS Registry No. 57998682)); BCNU ((N,N'-Bis(2-chloroethyl)-N-nitrosourea; NSC 409962; CAS Registry No. 154938)); busulfan (1,4-butanediol dimethanesulfonate; NSC 750; CAS Registry No. 55981); (carboxyphthalato)platinum (NSC 27164; CAS Registry No. 65296813); CBDCA ((cis-(1,1-cyclobutanedicarboxylato)diammineplatinum(II)); NSC 241240; CAS Registry No. 41575944)); CCNU ((N-(2-chloroethyl)-N'-cyclohexyl-N-nitrosourea; NSC 79037; CAS Registry No. 13010474)); CHIP (iproplatin; NSC 256927); chlorambucil (NSC 3088; CAS Registry No. 305033); chlorozotocin ((2-[[[(2-chloroethyl) nitrosoamino] carbonyl]amino]-2-deoxy-D-glucopyranose; NSC 178248; CAS Registry No. 54749905)); cis-platinum (cisplatin; NSC 119875; CAS Registry No. 15663271); clomesone (NSC 338947; CAS Registry No. 88343720); cyanomorpholino-doxorubicin (NCS 357704; CAS Registry No. 88254073); cyclodisone (NSC 348948; CAS Registry No. 99591738); dianhydrogalactitol (5,6-diepoxydulcitol; NSC 132313; CAS Registry No. 23261203); fluorodopan ((5-[(2-chloroethyl)-(2-fluoroethyl)amino]-6-methyl-uracil; NSC 73754; CAS Registry No. 834913); hepsulfam (NSC 329680; CAS Registry No. 96892578); hycanthone (NSC 142982; CAS Registry No. 23255938); melphalan (NSC 8806; CAS Registry No. 3223072); methyl CCNU ((1-(2-chloroethyl)-3-(trans-4-methylcyclohexane)-1-nitrosourea; NSC 95441; 13909096); mitomycin C (NSC 26980; CAS Registry No. 50077); mitozolamide (NSC 353451; CAS Registry No. 85622953); nitrogen mustard ((bis(2-chloroethyl)methylamine hydrochloride; NSC 762; CAS Registry No. 55867); PCNU ((1-(2-chloroethyl)-3-(2,6-dioxo-3-piperidyl)-1-nitrosourea; NSC 95466; CAS Registry No. 13909029)); piperazine alkylator ((1-(2-chloroethyl)-4-(3-chloropropyl)-piperazine dihydrochloride; NSC 344007)); piperazinedione (NSC 135758; CAS Registry No. 41109802); pipobroman ((N,N-bis(3-bromopropionyl) piperazine; NSC 25154; CAS Registry No. 54911)); porfiromycin (N-methylmitomycin C; NSC 56410; CAS Registry No. 801525); spirohydantoin mustard (NSC 172112; CAS Registry No. 56605164); teroxirone (triglycidylisocyanurate; NSC 296934; CAS Registry No. 2451629); tetraplatin (NSC 363812; CAS Registry No. 62816982); thio-tepa (N,N',N''-tri-1,2-ethanediylthio phosphoramide; NSC 6396; CAS Registry No. 52244); triethylenemelamine (NSC 9706; CAS Registry No. 51183); uracil nitrogen mustard (desmethyldopan; NSC 34462; CAS Registry No. 66751); Yoshi-864 ((bis(3-mesyloxy propyl)amine hydrochloride; NSC 102627; CAS Registry No. 3458228).

Topoisomerase I Inhibitors: camptothecin (NSC 94600; CAS Registry No. 7689-03-4); various camptothecin derivatives and analogs (for example, NSC 100880, NSC 603071, NSC 107124, NSC 643833, NSC 629971, NSC 295500, NSC 249910, NSC 606985, NSC 74028, NSC 176323, NSC 295501, NSC 606172, NSC 606173, NSC 610458, NSC 618939, NSC 610457, NSC 610459, NSC 606499, NSC 610456, NSC 364830, and NSC 606497); morpholinisoxorubicin (NSC 354646; CAS Registry No. 89196043); SN-38 (NSC 673596; CAS Registry No. 86639-52-3).

Topoisomerase II Inhibitors: doxorubicin (NSC 123127; CAS Registry No. 25316409); amonafide (benzisoquinolinedione; NSC 308847; CAS Registry No. 69408817); m-AMSA ((4'-(9-acridinylamino)-3'-methoxymethanesulfonanilide; NSC 249992; CAS Registry No. 51264143)); anthrapyrazole derivative ((NSC 355644); etoposide (VP-16; NSC 141540; CAS Registry No. 33419420); pyrazoloacridine ((pyrazolo[3,4,5-kl]acridine-2(6H)-propanamine, 9-methoxy-N, N-dimethyl-5-nitro-, monomethanesulfonate; NSC 366140; CAS Registry No. 99009219); bisantrene hydrochloride (NSC 337766; CAS Registry No. 71439684); daunorubicin (NSC 821151; CAS Registry No. 23541506); deoxydoxorubicin (NSC 267469; CAS Registry No. 63950061); mitoxantrone (NSC 301739; CAS Registry No. 70476823); menogaril (NSC 269148; CAS Registry No. 71628961); N,N-dibenzyl daunomycin (NSC 268242; CAS Registry No. 70878512); oxanthrazole (NSC 349174; CAS Registry No. 105118125); rubidazone (NSC 164011; CAS Registry No. 36508711); teniposide (VM-26; NSC 122819; CAS Registry No. 29767202).

DNA Intercalating Agents: anthramycin (CAS Registry No. 4803274); chicamycin A (CAS Registry No. 89675376); tomaymycin (CAS Registry No. 35050556); DC-81 (CAS Registry No. 81307246); sibiromycin (CAS Registry No. 12684332); pyrrolobenzodiazepine derivative (CAS Registry No. 945490095); SGD-1882 ((S)-2-(4-aminophenyl)-7-methoxy-8-(3-4(S)-7-methoxy-2-(4-methoxyphenyl)-5-oxo-5,11a-dihydro-1H-benzo[e]pyrrolo[1,2-a][1,4] diazepin-8-yl)oxy)propox-y)-1H-benzo[e]pyrrolo[1,2-a][1,4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5(11aH)-one); NSC 694501; CAS Registry No. 232931576).

RNA/DNA Antimetabolites: L-alanosine (NSC 153353; CAS Registry No. 59163416); 5-azacytidine (NSC 102816; CAS Registry No. 320672); 5-fluorouracil (NSC 19893; CAS Registry No. 51218); acivicin (NSC 163501; CAS Registry No. 42228922); aminopterin derivative N-[2-chloro-5-[[(2,4-diamino-5-methyl-6-quinazolinyl)methyl] amino]benzoyl]-L-aspartic acid (NSC 132483); aminopterin derivative N-[4-[[(2,4-diamino-5-ethyl-6-quinazolinyl) methyl]amino]benzoyl]L-aspartic acid (NSC 184692); aminopterin derivative N-[2-chloro-4-[[(2,4-diamino-6-pteridinyl)methyl]amino]benzoyl]L-aspartic acid monohydrate (NSC 134033); an antifo ((N$^\alpha$-(4-amino-4-deoxypteroyl)-N$^7$-hemiphthaloyl-L-ornithin-e; NSC 623017)); Baker's soluble antifol (NSC 139105; CAS Registry No. 41191042); dichlorallyl lawsone ((2-(3,3-dichloroallyl)-3-hydroxy-1,4-naphthoquinone; NSC 126771; CAS Registry No. 36417160); brequinar (NSC 368390; CAS Registry No. 96201886); ftorafur ((pro-drug; 5-fluoro-1-(tetrahydro-2-furyl)-uracil; NSC 148958; CAS Registry No. 37076689); 5,6-dihydro-5-azacytidine (NSC 264880; CAS Registry No. 62402317); methotrexate (NSC 740; CAS Registry No. 59052); methotrexate derivative (N-[[4-[[(2,4-diamino-6-pteridinyl)methyl]methylamino]-1-naphthalenyl]car-bonyl] L-glutamic acid; NSC 174121); PALA ((N-(phosphonoacetyl)-L-aspartate; NSC 224131; CAS Registry No. 603425565); pyrazofurin (NSC 143095; CAS Registry No. 30868305); trimetrexate (NSC 352122; CAS Registry No. 82952645).

DNA Antimetabolites: 3-HP (NSC 95678; CAS Registry No. 3814797); 2'-deoxy-5-fluorouridine (NSC 27640; CAS Registry No. 50919); 5-HP (NSC 107392; CAS Registry No. 19494894); α-TGDR (α-2'-deoxy-6-thioguanosine; NSC 71851 CAS Registry No. 2133815); aphidicolin glycinate (NSC 303812; CAS Registry No. 92802822); ara C (cytosine arabinoside; NSC 63878; CAS Registry No. 69749); 5-aza-2'-deoxycytidine (NSC 127716; CAS Registry No. 2353335); β-TGDR (β-2'-deoxy-6-thioguanosine; NSC 71261; CAS Registry No. 789617); cyclocytidine (NSC 145668; CAS Registry No. 10212256); guanazole (NSC 1895; CAS Registry No. 1455772); hydroxyurea (NSC 32065; CAS Registry No. 127071); inosine glycodialdehyde (NSC 118994; CAS Registry No. 23590990); macbecin II (NSC 330500; CAS Registry No. 73341738); pyrazoloimidazole (NSC 51143; CAS Registry No. 6714290); thioguanine (NSC 752; CAS Registry No. 154427); thiopurine (NSC 755; CAS Registry No. 50442).

Cell Cycle Modulators: silibinin (CAS Registry No. 22888-70-6); epigallocatechin gallate (EGCG; CAS Registry No. 989515); procyanidin derivatives (e.g., procyanidin A1 [CAS Registry No. 103883030], procyanidin B1 [CAS Registry No. 20315257], procyanidin B4 [CAS Registry No. 29106512], arecatannin B1 [CAS Registry No. 79763283]); isoflavones (e.g., genistein [4%5,7-trihydroxyisoflavone; CAS Registry No. 446720], daidzein [4',7-dihydroxyisoflavone, CAS Registry No. 486668]; indole-3-carbinol (CAS Registry No. 700061); quercetin (NSC 9219; CAS Registry No. 117395); estramustine (NSC 89201; CAS Registry No. 2998574); nocodazole (CAS Registry No. 31430189); podophyllotoxin (CAS Registry No. 518285); vinorelbine tartrate (NSC 608210; CAS Registry No. 125317397); cryptophycin (NSC 667642; CAS Registry No. 124689652).

Kinase Inhibitors: afatinib (CAS Registry No. 850140726); axitinib (CAS Registry No. 319460850); ARRY-438162 (binimetinib) (CAS Registry No. 606143899); bosutinib (CAS Registry No. 380843754); cabozantinib (CAS Registry No. 1140909483); ceritinib (CAS Registry No. 1032900256); crizotinib (CAS Registry No. 877399525); dabrafenib (CAS Registry No. 1195765457); dasatinib (NSC 732517; CAS Registry No. 302962498); erlotinib (NSC 718781; CAS Registry No. 183319699); everolimus (NSC 733504; CAS Registry No. 159351696); fostamatinib (NSC 745942; CAS Registry No. 901119355); gefitinib (NSC 715055; CAS Registry No. 184475352); ibrutinib (CAS Registry No. 936563961); imatinib (NSC 716051; CAS Registry No. 220127571); lapatinib (CAS Registry No. 388082788); lenvatinib (CAS Registry No. 857890392); mubritinib (CAS 366017096); nilotinib (CAS Registry No. 923288953); nintedanib (CAS Registry No. 656247175); palbociclib (CAS Registry No. 571190302); pazopanib (NSC 737754; CAS Registry No. 635702646); pegaptanib (CAS Registry No. 222716861); ponatinib (CAS Registry No. 1114544318); rapamycin (NSC 226080; CAS Registry No. 53123889); regorafenib (CAS Registry No. 755037037); AP 23573 (ridaforolimus) (CAS Registry No. 572924540); INCB018424 (ruxolitinib) (CAS Registry No. 1092939177); ARRY-142886 (selumetinib) (NSC 741078; CAS Registry No. 606143-52-6); sirolimus (NSC 226080; CAS Registry No. 53123889); sorafenib (NSC 724772; CAS Registry No. 475207591); sunitinib (NSC 736511; CAS Registry No. 341031547); tofacitinib (CAS Registry No. 477600752); temsirolimus (NSC 683864; CAS Registry No. 163635043); trametinib (CAS Registry No. 871700173); vandetanib (CAS Registry No. 443913733); vemurafenib (CAS Registry No. 918504651); SU6656 (CAS Registry No. 330161870); CEP-701 (lesaurtinib) (CAS Registry No. 111358884); XL019 (CAS Registry No. 945755566); PD-325901 (CAS Registry No. 391210109); PD-98059 (CAS Registry No. 167869218); ATP-competitive TORC1/TORC2 inhibitors including PI-103 (CAS Registry No. 371935749), PP242 (CAS Registry No. 1092351671), PP30 (CAS Registry No. 1092788094), Torin 1 (CAS Registry No. 1222998368), LY294002 (CAS Registry No. 154447366), XL-147 (CAS Registry No. 934526893), CAL-120 (CAS Registry No. 870281348), ETP-45658 (CAS Registry No. 1198357797), PX 866 (CAS Registry No. 502632668), GDC-0941 (CAS Registry No. 957054307), BGT226 (CAS Registry No. 1245537681), BEZ235 (CAS Registry No. 915019657), XL-765 (CAS Registry No. 934493762).

Protein Synthesis Inhibitors: acriflavine (CAS Registry No. 65589700); amikacin (NSC 177001; CAS Registry No. 39831555); arbekacin (CAS Registry No. 51025855); astromicin (CAS Registry No. 55779061); azithromycin (NSC 643732; CAS Registry No. 83905015); bekanamycin (CAS Registry No. 4696768); chlortetracycline (NSC 13252; CAS Registry No. 64722); clarithromycin (NSC 643733; CAS Registry No. 81103119); clindamycin (CAS Registry No. 18323449); clomocycline (CAS Registry No. 1181540); cycloheximide (CAS Registry No. 66819); dactinomycin (NSC 3053; CAS Registry No. 50760); dalfopristin (CAS Registry No. 112362502); demeclocycline (CAS Registry No. 127333); dibekacin (CAS Registry No. 34493986); dihydrostreptomycin (CAS Registry No. 128461); dirithromycin (CAS Registry No. 62013041); doxycycline (CAS Registry No. 17086281); emetine (NSC 33669; CAS Registry No. 483181); erythromycin (NSC 55929; CAS Registry No. 114078); flurithromycin (CAS Registry No. 83664208); framycetin (neomycin B; CAS Registry No. 119040); gentamycin (NSC 82261; CAS Registry No. 1403663); glycylcyclines, such as tigecycline (CAS Registry No. 220620097); hygromycin B (CAS Registry No. 31282049); isepamicin (CAS Registry No. 67814760); josamycin (NSC 122223; CAS Registry No. 16846245); kanamycin (CAS Registry No. 8063078); ketolides such as telithromycin (CAS Registry No. 191114484), cethromycin (CAS Registry No. 205110481), and solithromycin (CAS Registry No. 760981837); lincomycin (CAS Registry No. 154212); lymecycline (CAS Registry No. 992212); meclocycline (NSC 78502; CAS Registry No. 2013583); metacycline (rondomycin; NSC 356463; CAS Registry No. 914001); midecamycin (CAS Registry No. 35457808); minocycline (NSC 141993; CAS Registry No. 10118908); miocamycin (CAS Registry No. 55881077); neomycin (CAS Registry No. 119040); netilmicin (CAS Registry No. 56391561); oleandomycin (CAS Registry No. 3922905); oxazolidinones, such as eperezolid (CAS Registry No. 165800044), linezolid (CAS Registry No. 165800033), posizolid (CAS Registry No. 252260029), radezolid (CAS Registry No. 869884786), ranbezolid (CAS Registry No. 392659380), sutezolid (CAS Registry No. 168828588), tedizolid (CAS Registry No. 856867555); oxytetracycline (NSC 9169; CAS Registry No. 2058460); paromomycin (CAS Registry No. 7542372); penimepicycline (CAS Registry No. 4599604); peptidyl transferase inhibitors, e.g., chloramphenicol (NSC 3069; CAS Registry No. 56757) and derivatives such as azidamfenicol (CAS Registry No. 13838089), florfenicol (CAS Registry No. 73231342), and thiamphenicol (CAS Registry No. 15318453), and pleuromutilins such as retapamulin (CAS Registry No. 224452668), tiamulin (CAS Registry No. 55297955), valnemulin (CAS Registry No. 101312929); pirlimycin (CAS Registry No. 79548735); puromycin (NSC 3055; CAS Registry No. 53792); quinupristin (CAS Registry No. 120138503); ribostamycin (CAS Registry No. 53797356); rokitamycin (CAS Registry No. 74014510); rolitetracycline (CAS Registry No. 751973); roxithromycin (CAS Registry No. 80214831); sisomicin (CAS Registry No. 32385118); spectinomycin (CAS Registry No. 1695778); spiramycin (CAS Registry No. 8025818); streptogramins such as pristinamycin (CAS Registry No. 270076603), quinupristin/dalfopristin (CAS Registry No. 126602899), and virginiamycin (CAS Registry No. 11006761); streptomycin (CAS Registry No. 57921); tetracycline (NSC 108579; CAS Registry No. 60548); tobramycin (CAS Registry No. 32986564); troleandomycin (CAS Registry No. 2751099); tylosin (CAS Registry No. 1401690); verdamicin (CAS Registry No. 49863481).

Histone Deacetylase Inhibitors: abexinostat (CAS Registry No. 783355602); belinostat (NSC 726630; CAS Registry No. 414864009); chidamide (CAS Registry No. 743420022); entinostat (CAS Registry No. 209783802); givinostat (CAS Registry No. 732302997); mocetinostat (CAS Registry No. 726169739); panobinostat (CAS Registry No. 404950807); quisinostat (CAS Registry No. 875320299); resminostat (CAS Registry No. 864814880); romidepsin (CAS Registry No. 128517077); sulforaphane (CAS Registry No. 4478937); thioureidobutyronitrile (Kevetrin™; CAS Registry No. 6659890); valproic acid (NSC 93819; CAS Registry No. 99661); vorinostat (NSC 701852; CAS Registry No. 149647789); ACY-1215 (rocilinostat; CAS Registry No. 1316214524); CUDC-101 (CAS Registry No. 1012054599); CHR-2845 (tefinostat; CAS Registry No. 914382608); CHR-3996 (CAS Registry No. 1235859138); 4SC-202 (CAS Registry No. 910462430); CG200745 (CAS Registry No. 936221339); SB939 (pracinostat; CAS Registry No. 929016966).

Mitochondria Inhibitors: pancratistatin (NSC 349156; CAS Registry No. 96281311); rhodamine-123 (CAS Registry No. 63669709); edelfosine (NSC 324368; CAS Registry No. 70641519); d-alpha-tocopherol succinate (NSC 173849; CAS Registry No. 4345033); compound 11β (CAS Registry No. 865070377); aspirin (NSC 406186; CAS Registry No. 50782); ellipticine (CAS Registry No. 519233); berberine (CAS Registry No. 633658); cerulenin (CAS Registry No. 17397896); GX015-070 (Obatoclax®; 1H-Indole, 2-(2-((3,5-dimethyl-1H-pyrrol-2-yl)methylene)-3-methoxy-2H-pyrrol-5-yl)-; NSC 729280; CAS Registry No. 803712676); celastrol (tripterine; CAS Registry No. 34157830); metformin (NSC 91485; CAS Registry No.

1115704); Brilliant green (NSC 5011; CAS Registry No. 633034); ME-344 (CAS Registry No. 1374524556).

Antimitotic Agents: allocolchicine (NSC 406042); auristatins, such as MMAE (monomethyl auristatin E; CAS Registry No. 474645-27-7) and MMAF (monomethyl auristatin F; CAS Registry No. 745017-94-1; halichondrin B (NSC 609395); colchicine (NSC 757; CAS Registry No. 64868); cholchicine derivative (N-benzoyl-deacetyl benzamide; NSC 33410; CAS Registry No. 63989753); dolastatin 10 (NSC 376128; CAS Registry No 110417-88-4); maytansine (NSC 153858; CAS Registry No. 35846-53-8); rhozoxin (NSC 332598; CAS Registry No. 90996546); taxol (NSC 125973; CAS Registry No. 33069624); taxol derivative ((2'-N-[3-(dimethylamino)propyl]glutaramate taxol; NSC 608832); thiocolchicine (3-demethylthiocolchicine; NSC 361792); trityl cysteine (NSC 49842; CAS Registry No. 2799077); vinblastine sulfate (NSC 49842; CAS Registry No. 143679); vincristine sulfate (NSC 67574; CAS Registry No. 2068782).

Any of these agents that include or that may be modified to include a site of attachment to an antibody may be included in the ADCs disclosed herein.

In a specific embodiment, the cytotoxic and/or cytostatic agent is an antimitotic agent.

In another specific embodiment, the cytotoxic and/or cytostatic agent is an auristatin, for example, monomethyl auristatin E ("MMAE") or monomethyl auristatin F ("MMAF").

6.2.2. Linkers

In the anti-glyco-MUC1 ADCs of the disclosure, the cytotoxic and/or cytostatic agents are linked to the antibody by way of linkers. The linker linking a cytotoxic and/or cytostatic agent to the antibody of an ADC may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the antibody, or monovalent such that covalently they link a single agent to a single site on the antibody.

As will be appreciated by skilled artisans, the linkers link cytotoxic and/or cytostatic agents to the antibody by forming a covalent linkage to the cytotoxic and/or cytostatic agent at one location and a covalent linkage to antibody at another. The covalent linkages are formed by reaction between functional groups on the linker and functional groups on the agents and antibody. As used herein, the expression "linker" is intended to include (i) unconjugated forms of the linker that include a functional group capable of covalently linking the linker to a cytotoxic and/or cytostatic agent and a functional group capable of covalently linking the linker to an antibody; (ii) partially conjugated forms of the linker that includes a functional group capable of covalently linking the linker to an antibody and that is covalently linked to a cytotoxic and/or cytostatic agent, or vice versa; and (iii) fully conjugated forms of the linker that is covalently linked to both a cytotoxic and/or cytostatic agent and an antibody. In some specific embodiments of linkers and anti-glyco-MUC1 ADCs of the disclosure, as well as synthons used to conjugate linker-agents to antibodies, moieties comprising the functional groups on the linker and covalent linkages formed between the linker and antibody are specifically illustrated as $R_x$ and XY, respectively.

The linkers are preferably, but need not be, chemically stable to conditions outside the cell, and may be designed to cleave, immolate and/or otherwise specifically degrade inside the cell. Alternatively, linkers that are not designed to specifically cleave or degrade inside the cell may be used. Choice of stable versus unstable linker may depend upon the toxicity of the cytotoxic and/or cytostatic agent. For agents that are toxic to normal cells, stable linkers are preferred. Agents that are selective or targeted and have lower toxicity to normal cells may utilize, chemical stability of the linker to the extracellular milieu is less important. A wide variety of linkers useful for linking drugs to antibodies in the context of ADCs are known in the art. Any of these linkers, as well as other linkers, may be used to link the cytotoxic and/or cytostatic agents to the antibody of the anti-glyco-MUC1 ADCs of the disclosure.

Exemplary polyvalent linkers that may be used to link many cytotoxic and/or cytostatic agents to a single antibody molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the content of which are incorporated herein by reference in their entireties. For example, the Fleximer linker technology developed by Mersana et al. has the potential to enable high-DAR ADCs with good physicochemical properties. As shown below, the Mersana technology is based on incorporating drug molecules into a solubilizing poly-acetal backbone via a sequence of ester bonds. The methodology renders highly-loaded ADCs (DAR up to 20) while maintaining good physicochemical properties.

Additional examples of dendritic type linkers can be found in US 2006/116422; US 2005/271615; de Groot et al. (2003) Angew. Chem. Int. Ed. 42:4490-4494; Amir et al. (2003) Angew. Chem. Int. Ed. 42:4494-4499; Shamis et al. (2004) J. Am. Chem. Soc. 126:1726-1731; Sun et al. (2002) Bioorganic & Medicinal Chemistry Letters 12:2213-2215; Sun et al. (2003) Bioorganic & Medicinal Chemistry 11:1761-1768; King et al. (2002) Tetrahedron Letters 43:1987-1990, each of which is incorporated herein by reference.

Exemplary monovalent linkers that may be used are described, for example, in Nolting, 2013, Antibody-Drug Conjugates, Methods in Molecular Biology 1045:71-100; Kitson et al., 2013, CROs/CMOs—Chemica Oggi—Chemistry Today 31(4):30-38; Ducry et al., 2010, Bioconjugate Chem. 21:5-13; Zhao et al., 2011, J. Med. Chem. 54:3606-3623; U.S. Pat. Nos. 7,223,837; 8,568,728; 8,535,678; and WO2004010957, each of which is incorporated herein by reference.

By way of example and not limitation, some cleavable and noncleavable linkers that may be included in the anti-glyco-MUC1 ADCs of the disclosure are described below.

6.2.3. Cleavable Linkers

In certain embodiments, the linker selected is cleavable in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable. In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures:

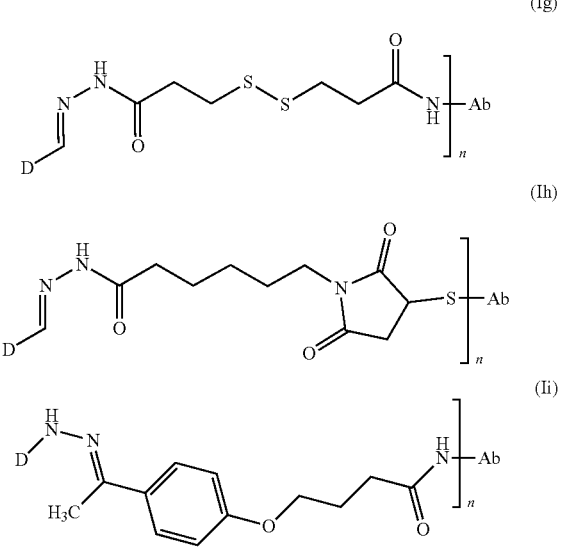

wherein D and Ab represent the cytotoxic and/or cytostatic agent (drug) and Ab, respectively, and n represents the number of drug-linkers linked to the antibody. In certain linkers such as linker (Ig), the linker comprises two cleavable groups—a disulfide and a hydrazone moiety. For such linkers, effective release of the unmodified free drug requires acidic pH or disulfide reduction and acidic pH. Linkers such as (Ih) and (Ii) have been shown to be effective with a single hydrazone cleavage site.

Additional linkers which remain intact during systemic circulation and undergo hydrolysis and release the drug when the ADC is internalized into acidic cellular compartments include carbonates. Such linkers can be useful in cases where the cytotoxic and/or cytostatic agent can be covalently attached through an oxygen.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonably stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hindrance adjacent to the disulfide bond.

ADCs including exemplary disulfide-containing linkers include the following structures:

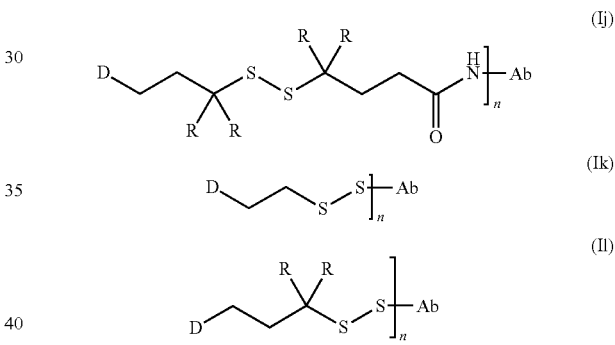

wherein D and Ab represent the drug and antibody, respectively, n represents the number of drug-linkers linked to the antibody and R is independently selected at each occurrence from hydrogen or alkyl, for example. In certain embodiments, increasing steric hindrance adjacent to the disulfide bond increases the stability of the linker. Structures such as (Ij) and (Il) show increased in vivo stability when one or more R groups is selected from a lower alkyl such as methyl.

Another type of cleavable linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor cells.

In exemplary embodiments, the cleavable peptide is selected from tetrapeptides such as Gly-Phe-Leu-Gly (SEQ ID NO:100), Ala-Leu-Ala-Leu (SEQ ID NO:101) or dipeptides such as Val-Cit, Val-Ala, Met-(D)Lys, Asn-(D)Lys, Val-(D)Asp, Phe-Lys, Ile-Val, Asp-Val, His-Val, NorVal-(D) Asp, Ala-(D)Asp 5, Met-Lys, Asn-Lys, lie-Pro, Me3Lys-Pro, PhenylGly-(D)Lys, Met-(D)Lys, Asn-(D)Lys, Pro-(D)Lys, Met-(D)Lys, Asn-(D)Lys, AM Met-(D)Lys, Asn-(D)Lys, AW Met-(D)Lys, and Asn-(D)Lys. In certain embodiments, dipeptides are preferred over longer polypeptides due to hydrophobicity of the longer peptides.

A variety of dipeptide-based cleavable linkers useful for linking drugs such as doxorubicin, mitomycin, camptothecin, pyrrolobenzodiazepine, tallysomycin and auristatin/auristatin family members to antibodies have been described (see, Dubowchik et al., 1998, J. Org. Chem. 67:1866-1872; Dubowchik et al., 1998, Bioorg. Med. Chem. Lett. 8(21): 3341-3346; Walker et al., 2002, Bioorg. Med. Chem. Lett. 12:217-219; Walker et al., 2004, Bioorg. Med. Chem. Lett. 14:4323-4327; Sutherland et al., 2013, Blood 122: 1455-1463; and Francisco et al., 2003, Blood 102:1458-1465, of each of which is incorporated herein by reference). All of these dipeptide linkers, or modified versions of these dipeptide linkers, may be used in the anti-glyco-MUC1 ADCs of the disclosure. Other dipeptide linkers that may be used include those found in ADCs such as Seattle Genetics' Brentuximab Vendotin SGN-35 (Adcetris™), Seattle Genetics SGN-75 (anti-CD-70, Val-Cit-monomethyl auristatin F(MMAF), Seattle Genetics SGN-CD33A (anti-CD-33, Val-Ala-(SGD-1882)), Celldex Therapeutics glembatumumab (CDX-011) (anti-NMB, Val-Cit-monomethyl auristatin E (MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-amidobenzyl ether and release of the drug:

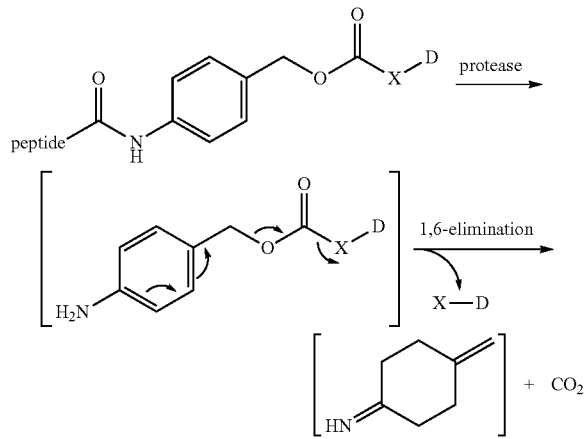

wherein X-D represents the unmodified drug.

Heterocyclic variants of this self-immolative group have also been described. See for example, U.S. Pat. No. 7,989,434, incorporated herein by reference.

In some embodiments, the enzymatically cleavable linker is a β-glucuronic acid-based linker. Facile release of the drug may be realized through cleavage of the β-glucuronide glycosidic bond by the lysosomal enzyme β-glucuronidase. This enzyme is present abundantly within lysosomes and is overexpressed in some tumor types, while the enzyme activity outside cells is low. β-Glucuronic acid-based linkers may be used to circumvent the tendency of an ADC to undergo aggregation due to the hydrophilic nature of β-glucuronides. In some embodiments, β-glucuronic acid-based linkers are preferred as linkers for ADCs linked to hydrophobic drugs. The following scheme depicts the release of the drug from and ADC containing a β-glucuronic acid-based linker:

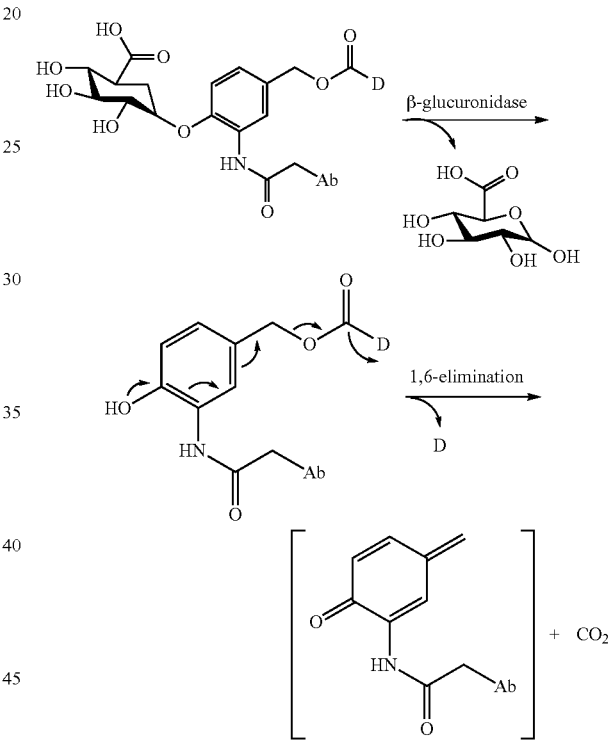

A variety of cleavable β-glucuronic acid-based linkers useful for linking drugs such as auristatins, camptothecin and doxorubicin analogues, CBI minor-groove binders, and psymberin to antibodies have been described (see, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013; Jeffrey et al., 2006, Bioconjug. Chem. 17:831-840; Jeffrey et al., 2007, Bioorg. Med. Chem. Lett. 17:2278-2280; and Jiang et al., 2005, J. Am. Chem. Soc. 127:11254-11255, each of which is incorporated herein by reference). All of these β-glucuronic acid-based linkers may be used in the anti-glyco-MUC1 ADCs of the disclosure.

Additionally, cytotoxic and/or cytostatic agents containing a phenol group can be covalently bonded to a linker through the phenolic oxygen. One such linker, described in WO 2007/089149, relies on a methodology in which a diamino-ethane "SpaceLink" is used in conjunction with traditional "PABO"-based self-immolative groups to deliver phenols. The cleavage of the linker is depicted schematically below, where D represents a cytotoxic and/or cytostatic agent having a phenolic hydroxyl group.

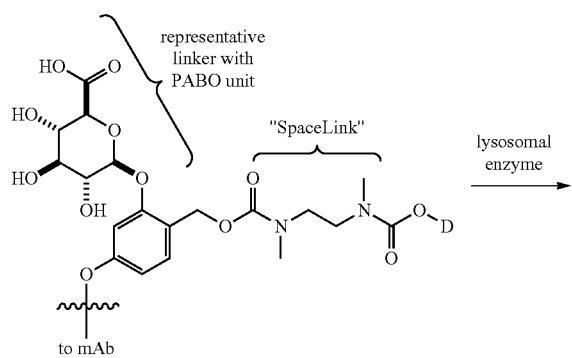

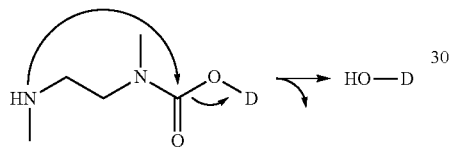

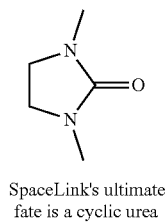

SpaceLink's ultimate fate is a cyclic urea

Cleavable linkers may include noncleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazone or a dipeptide.

Other degradable linkages that may be included in linkers include ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the linker comprises an enzymatically cleavable peptide moiety, for example, a linker comprising structural formula (IVa) or (IVb):

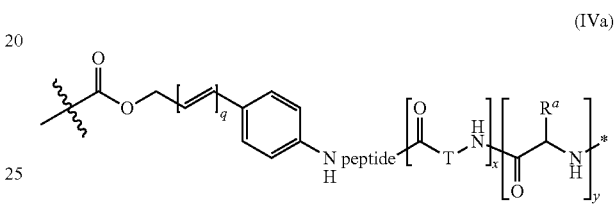

(IVa)

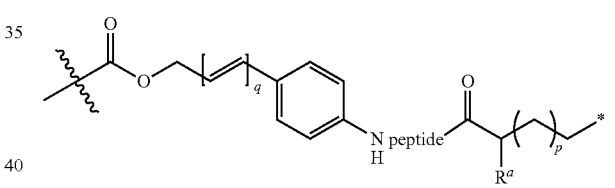

(IVb)

or a salt thereof, wherein: peptide represents a peptide (illustrated C→N and not showing the carboxy and amino "termini") cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; p is an integer ranging from 0 to 5; q is 0 or 1; x is 0 or 1; ∮ represents the point of attachment of the linker to a cytotoxic and/or cytostatic agent; and * represents the point of attachment to the remainder of the linker.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the dipeptide is selected from: Cit-Val; and Ala-Val.

Specific exemplary embodiments of linkers according to structural formula (IVa) that may be included in the anti-glyco-MUC1 ADCs of the disclosure include the linkers illustrated below (as illustrated, the linkers include a group suitable for covalently linking the linker to an antibody):

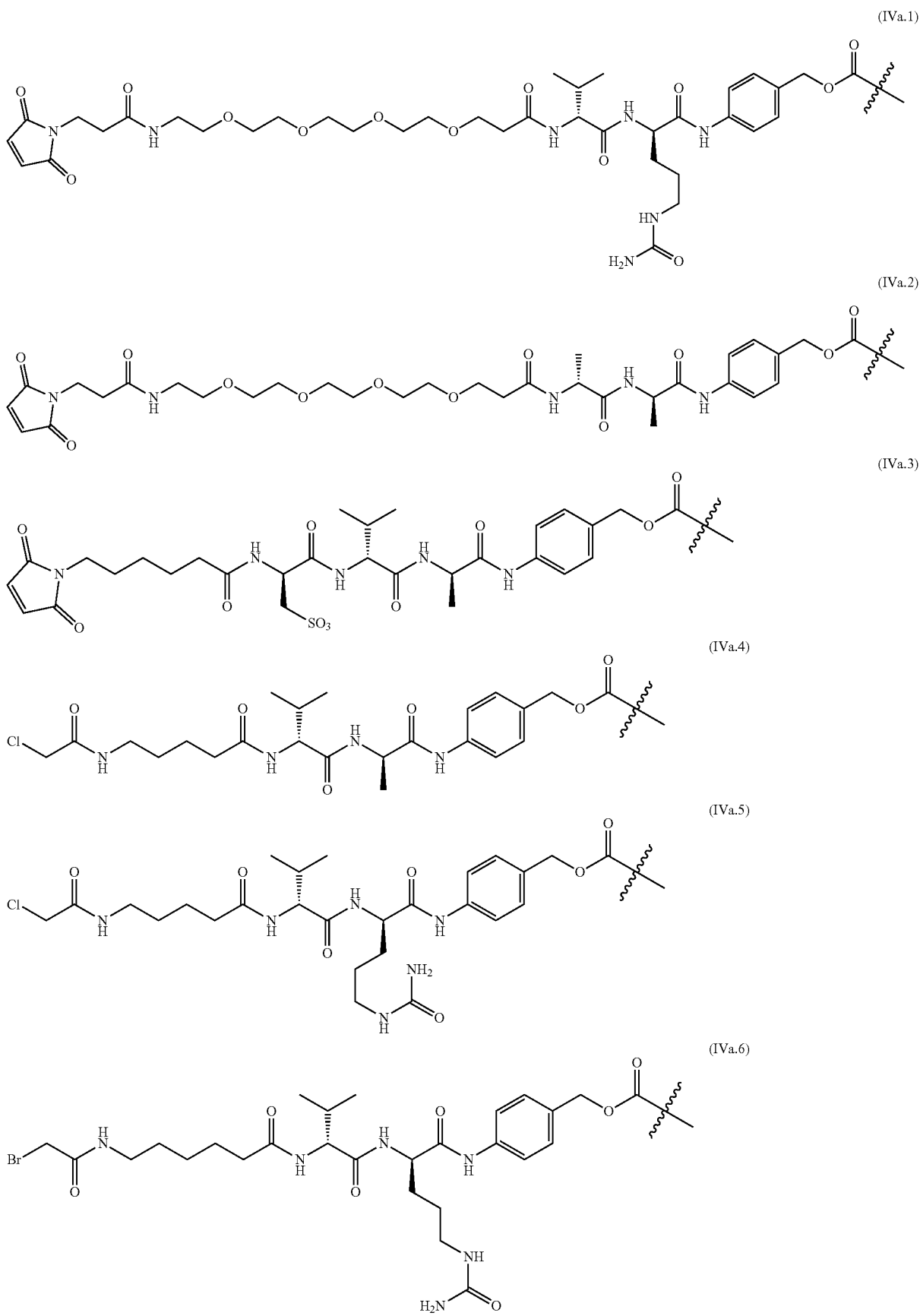

(IVa.7)
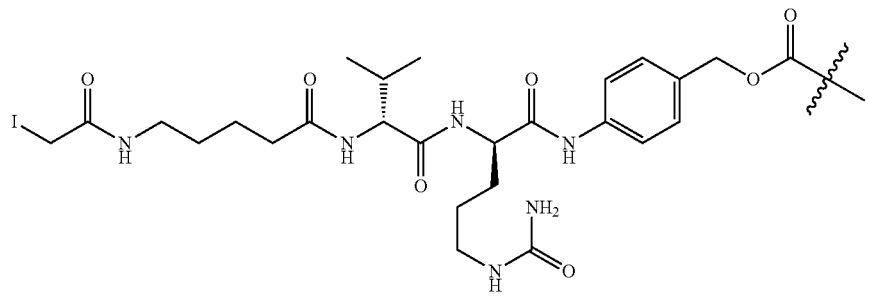
Specific exemplary embodiments of linkers according to structural formula (IVb) that may be included in the anti-glyco-MUC1 ADCs of the disclosure include the linkers illustrated below (as illustrated, the linkers include a group suitable for covalently linking the linker to an antibody):
(IVb.1)
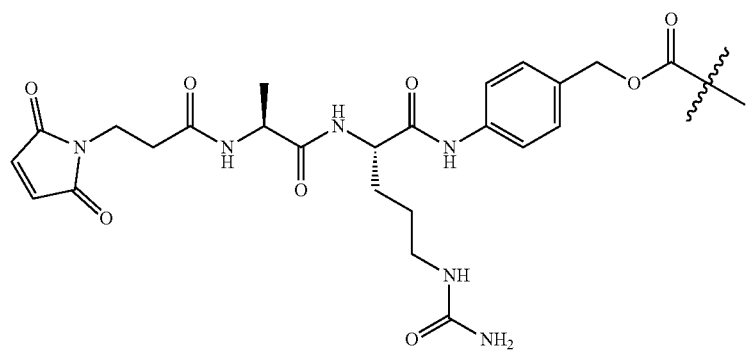
(IVb.2)
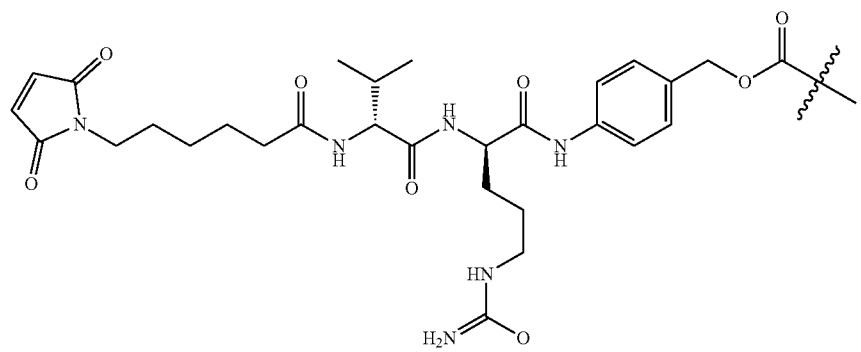
(IVb.3)
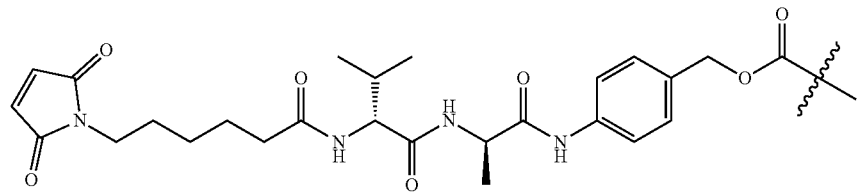

-continued
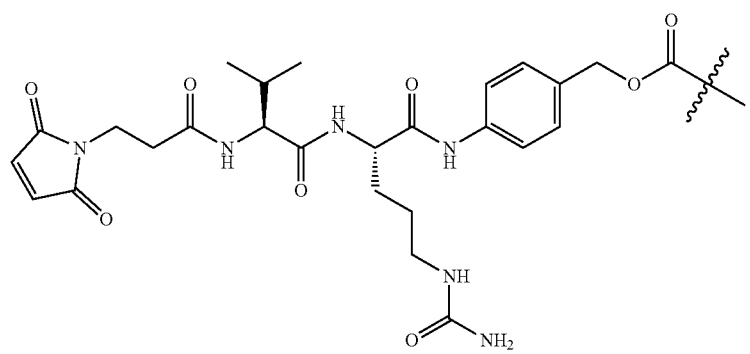
(IVb.4)
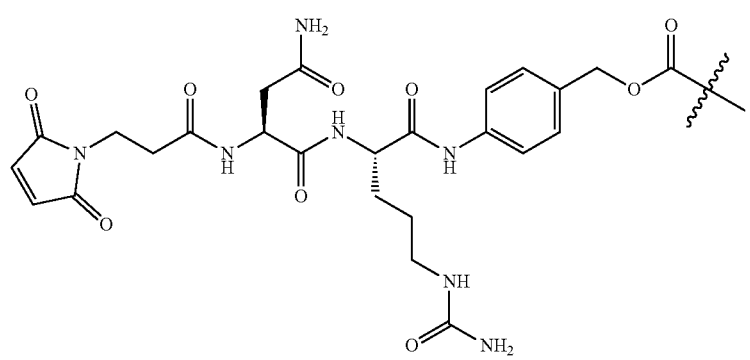
(IVb.5)
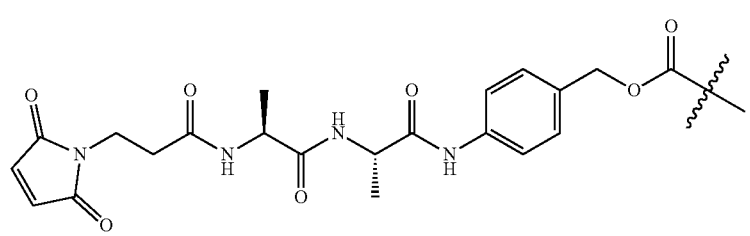
(IVb.6)
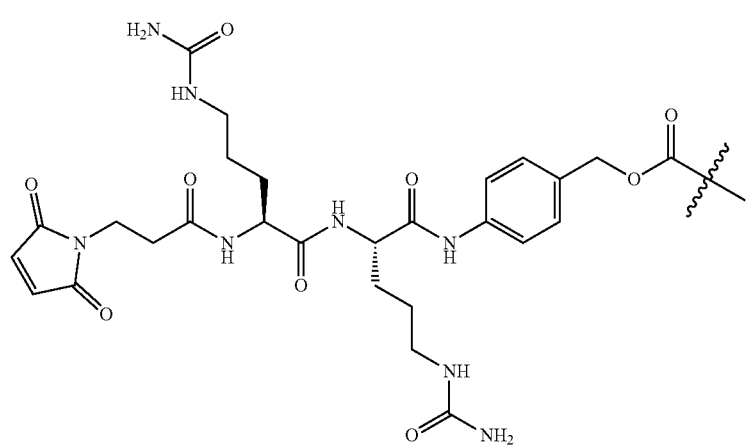
(IVb.7)
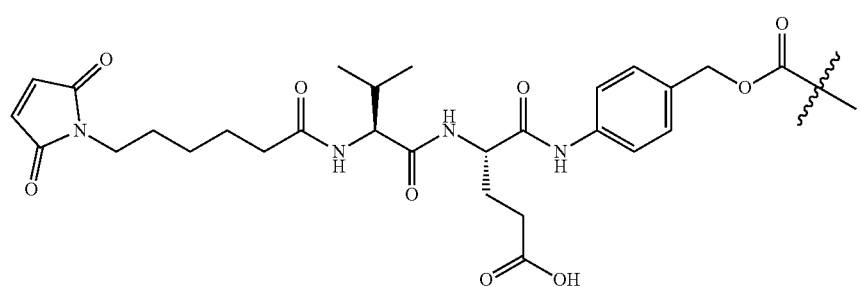
(IVb.8)

-continued
(IVb.9)
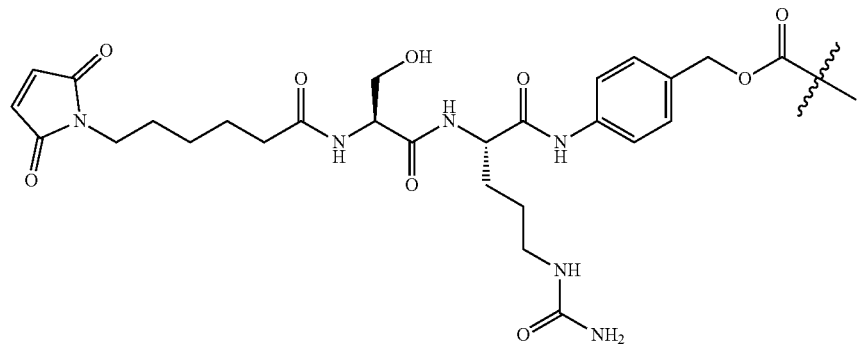
(IVb.10)
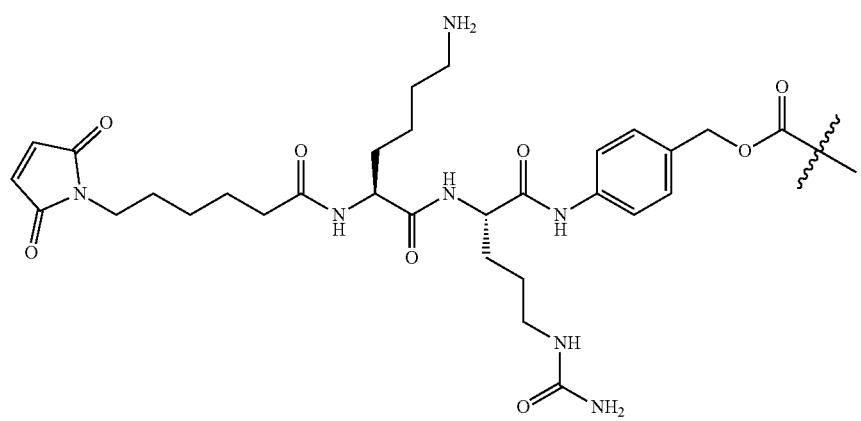
(IVb.11)
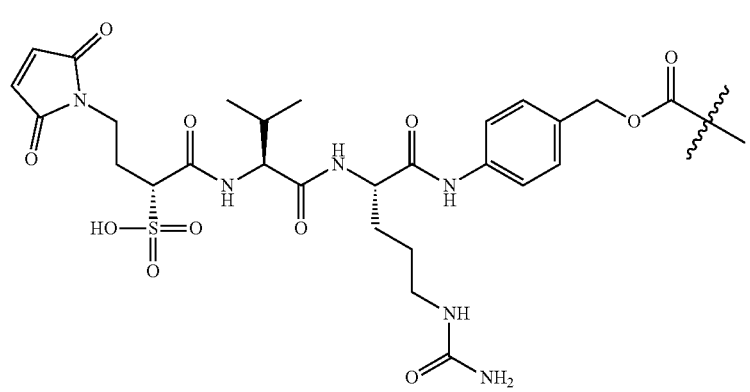
(IVb.12)
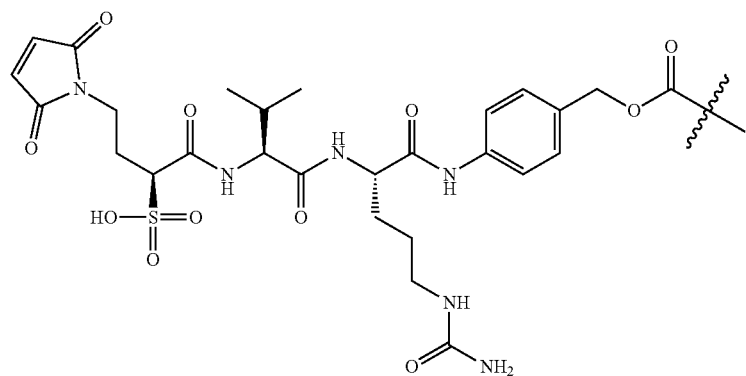

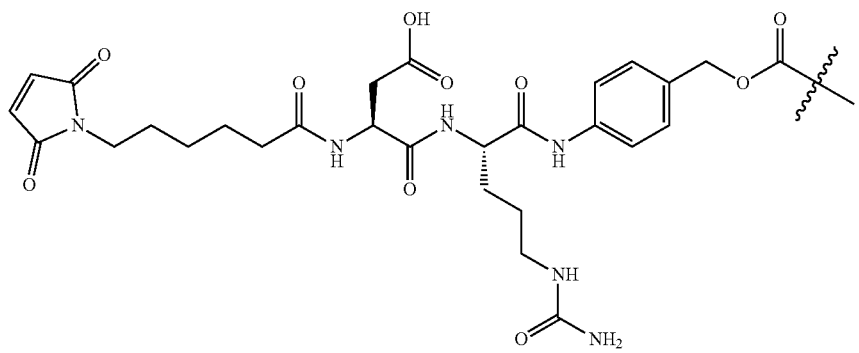
(IVb.13)
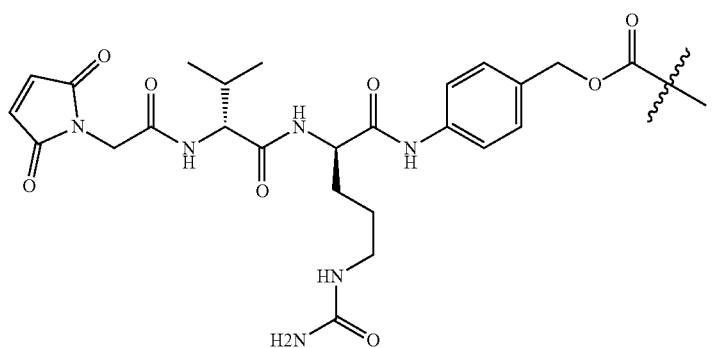
(IVb.14)
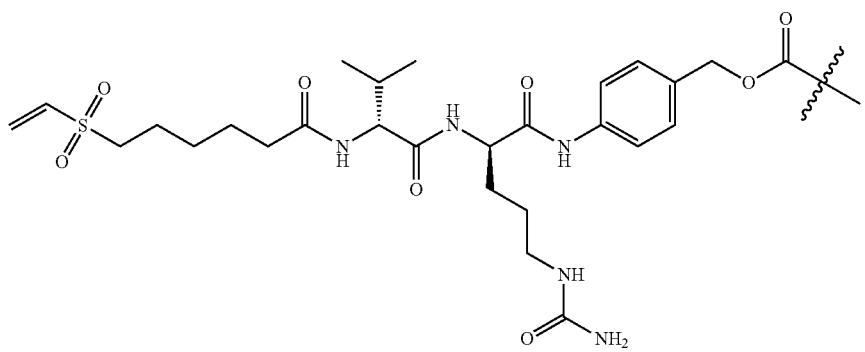
(IVb.15)
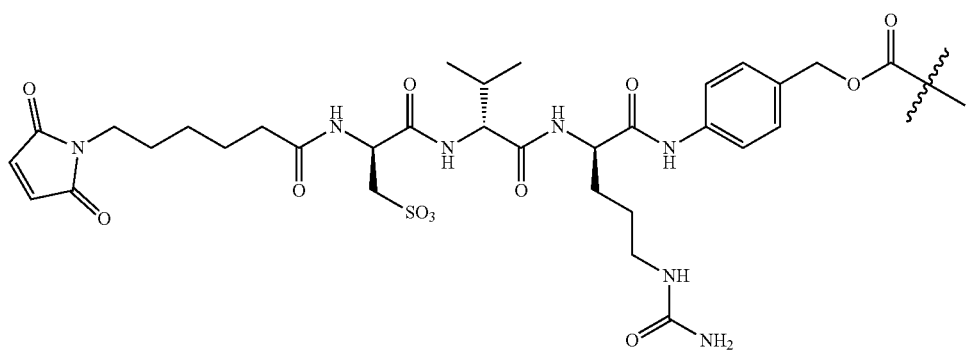
(IVb.16)

(IVb.17)

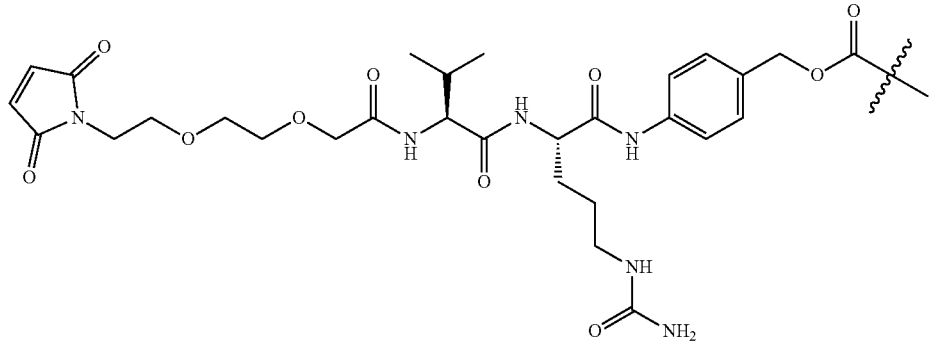

(IVb.18)

(IVb.19)

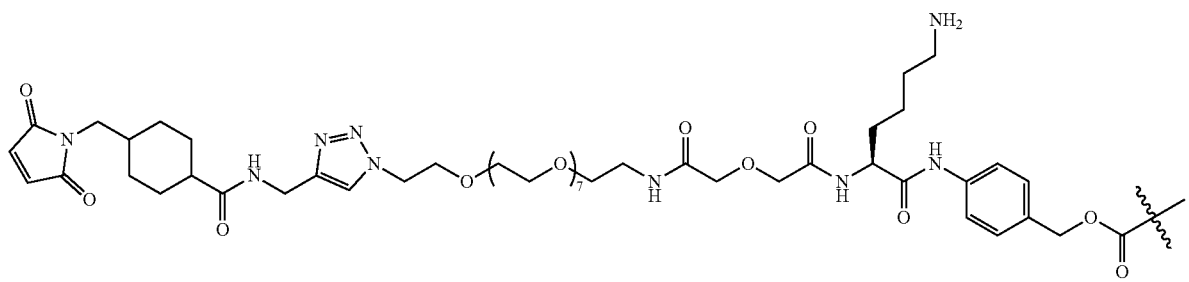

In certain embodiments, the linker comprises an enzymatically cleavable peptide moiety, for example, a linker comprising structural formula (IVc) or (IVd):

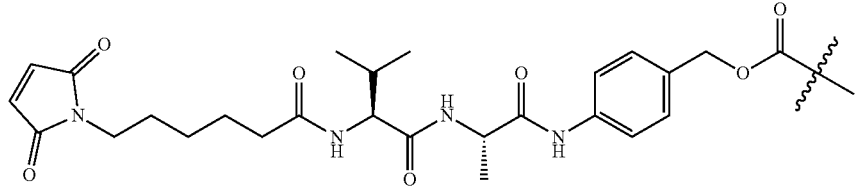

(IVc)

(IVd)

or a salt thereof, wherein: peptide represents a peptide (illustrated C→N and not showing the carboxy and amino "termini") cleavable by a lysosomal enzyme; T represents a polymer comprising one or more ethylene glycol units or an alkylene chain, or combinations thereof; Ra is selected from hydrogen, alkyl, sulfonate and methyl sulfonate; p is an integer ranging from 0 to 5; q is 0 or 1; x is 0 or 1; y is 0 or 1; _x_ represents the point of attachment of the linker to a cytotoxic and/or cytostatic agent; and * represents the point of attachment to the remainder of the linker.

Specific exemplary embodiments of linkers according to structural formula (IVc) that may be included in the anti-glyco-MUC1 ADCs of the disclosure include the linkers illustrated below (as illustrated, the linkers include a group suitable for covalently linking the linker to an antibody):

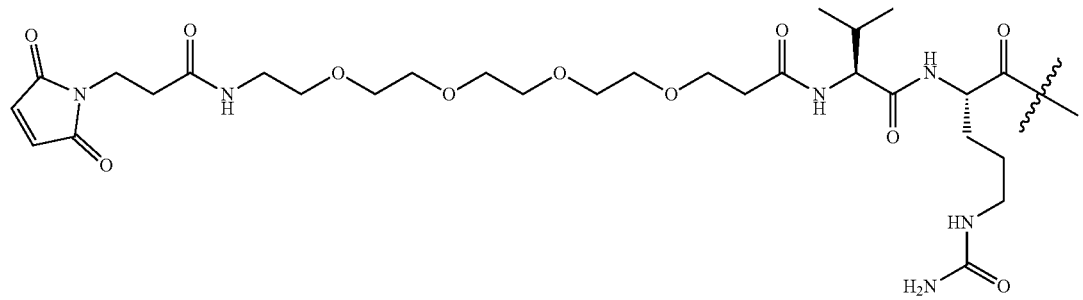
(IVc.1)
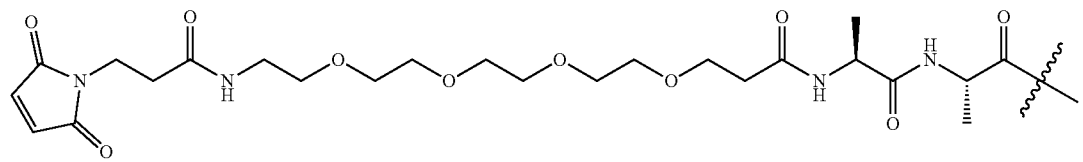
(IVc.2)
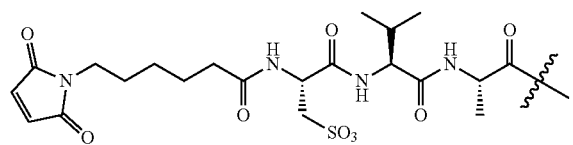
(IVc.3)
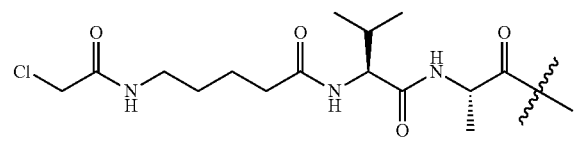
(IVc.4)
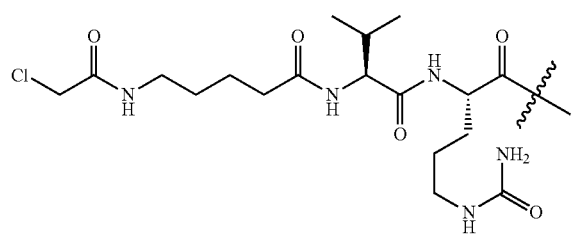
(IVc.5)
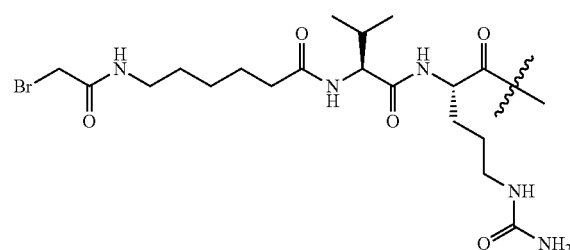
(IVc.6)
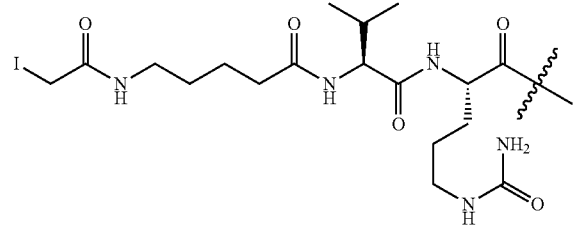
(IVc.7)

Specific exemplary embodiments of linkers according to structural formula (IVd) that may be included in the anti-glyco-MUC1 ADCs of the disclosure include the linkers illustrated below (as illustrated, the linkers include a group suitable for covalently linking the linker to an antibody):
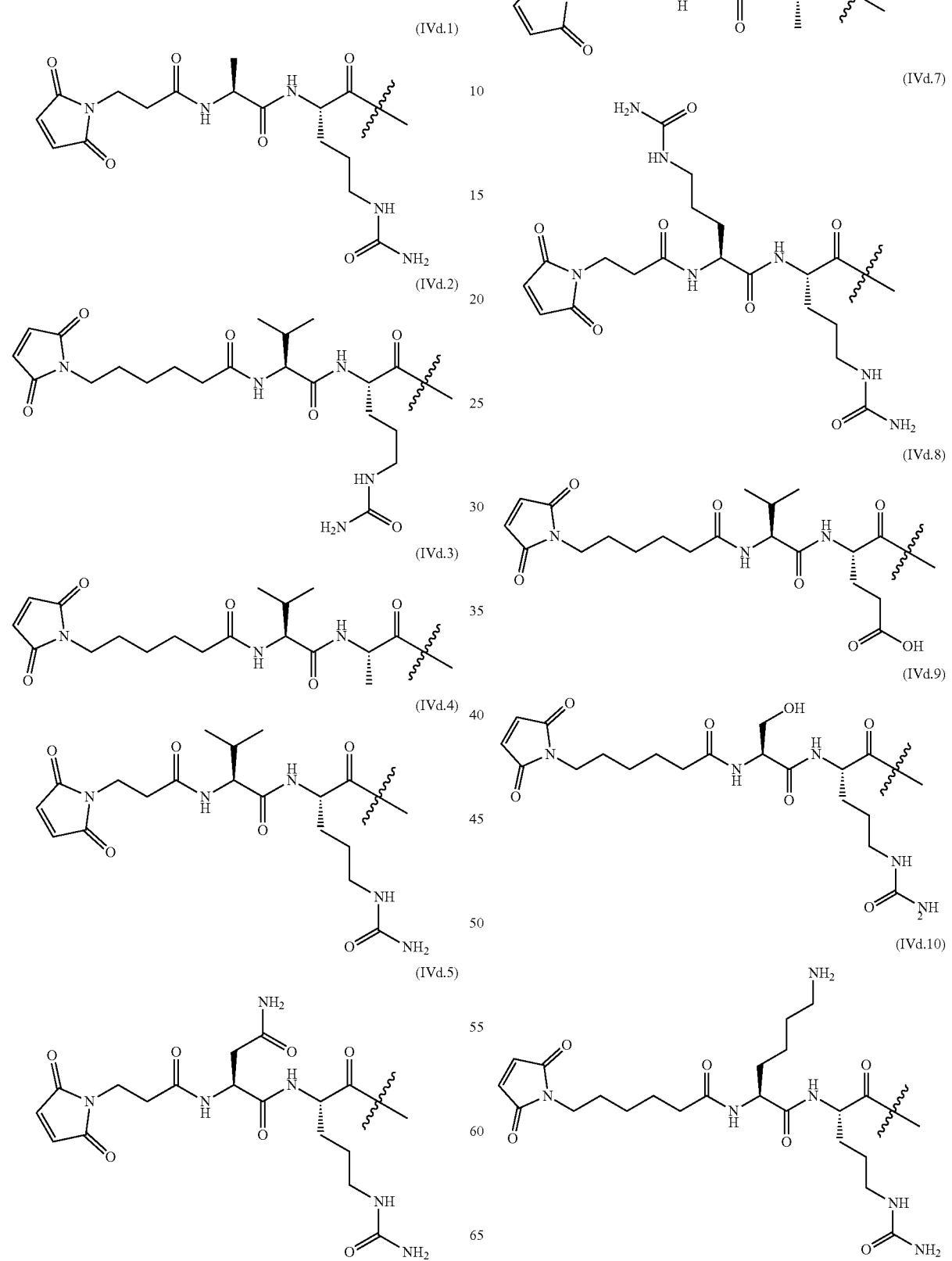

-continued

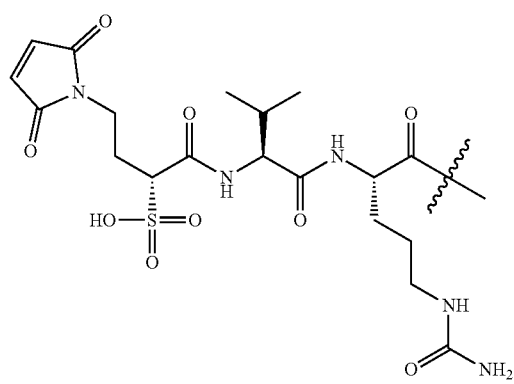
(IVd.11)

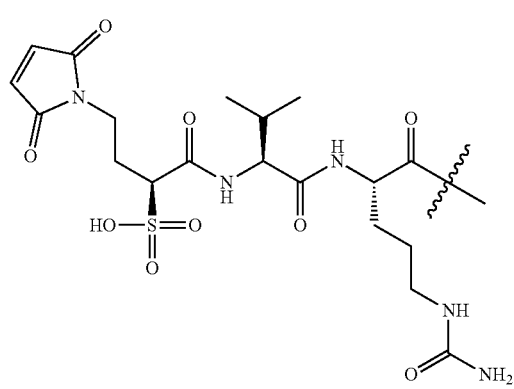
(IVd.12)

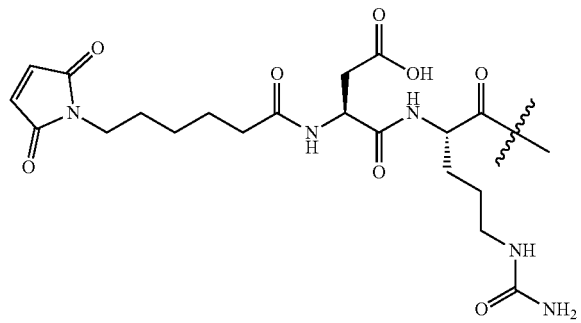
(IVd.13)

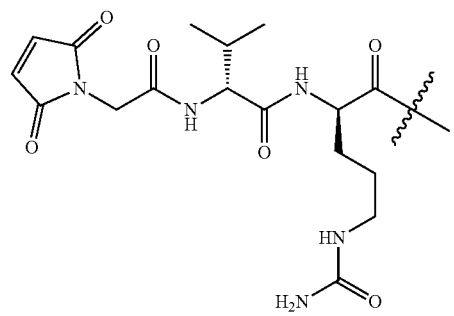
(IVd.14)

-continued

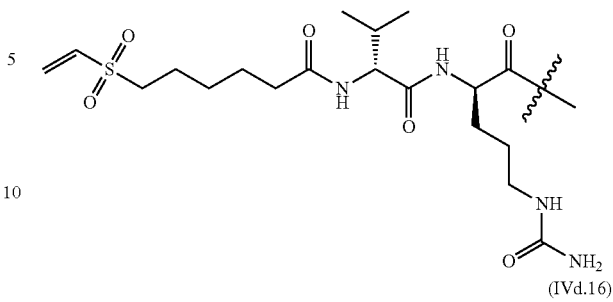
(IVd.15)

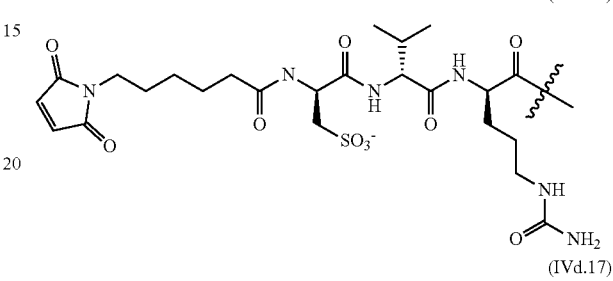
(IVd.16)

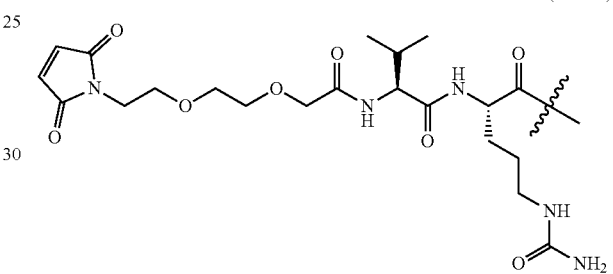
(IVd.17)

In certain embodiments, the linker comprising structural formula (IVa), (IVb), (IVc), or (IVd) further comprises a carbonate moiety cleavable by exposure to an acidic medium. In particular embodiments, the linker is attached through an oxygen to a cytotoxic and/or cytostatic agent.

6.2.4. Non-Cleavable Linkers

Although cleavable linkers may provide certain advantages, the linkers comprising the anti-glyco-MUC1 ADC of the disclosure need not be cleavable. For noncleavable linkers, the release of drug does not depend on the differential properties between the plasma and some cytoplasmic compartments. The release of the drug is postulated to occur after internalization of the ADC via antigen-mediated endocytosis and delivery to lysosomal compartment, where the antibody is degraded to the level of amino acids through intracellular proteolytic degradation. This process releases a drug derivative, which is formed by the drug, the linker, and the amino acid residue to which the linker was covalently attached. The amino acid drug metabolites from conjugates with noncleavable linkers are more hydrophilic and generally less membrane permeable, which leads to less bystander effects and less nonspecific toxicities compared to conjugates with a cleavable linker. In general, ADCs with non-cleavable linkers have greater stability in circulation than ADCs with cleavable linkers. Non-cleavable linkers may be alkylene chains, or maybe polymeric in natures, such as, for example, based upon polyalkylene glycol polymers, amide polymers, or may include segments of alkylene chains, polyalkylene glocols and/or amide polymers.

A variety of non-cleavable linkers used to link drugs to antibodies have been described. See, Jeffrey et al., 2006, Bioconjug. Chem. 17; 831-840; Jeffrey et al., 2007, Bioorg. Med. Chem. Lett. 17:2278-2280; and Jiang et al., 2005, J. Am. Chem. Soc. 127:11254-11255, each of which is incorporated herein by reference. All of these linkers may be included in the anti-glyco-MUC1 ADCs of the disclosure.

In certain embodiments, the linker is non-cleavable in vivo, for example a linker according to structural formula (VIa), (VIb), (VIc) or (VId) (as illustrated, the linkers include a group suitable for covalently linking the linker to an antibody:

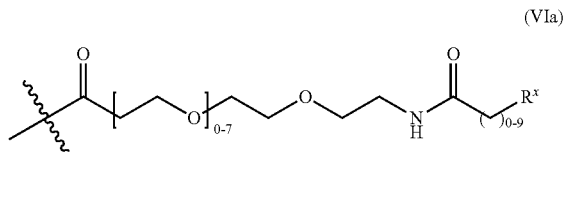

(VIa)

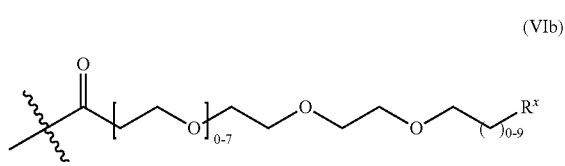

(VIb)

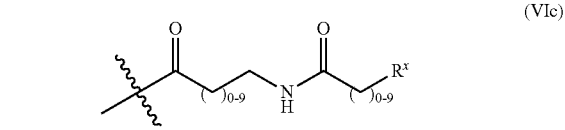

(VIc)

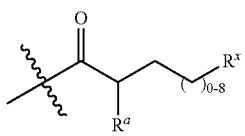

(VId)

or salts thereof, wherein: Ra is selected from hydrogen, alkyl, sulfonate and methyl sulfonate; $R^x$ is a moiety including a functional group capable of covalently linking the linker to an antibody; and ∱ represents the point of attachment of the linker to a cytotoxic and/or cytostatic agent.

Specific exemplary embodiments of linkers according to structural formula (VIa)-(VId) that may be included in the anti-glyco-MUC1 ADCs of the disclosure include the linkers illustrated below (as illustrated, the linkers include a group suitable for covalently linking the linker to an antibody, and ∱ represents the point of attachment to a cytotoxic and/or cytostatic agent):

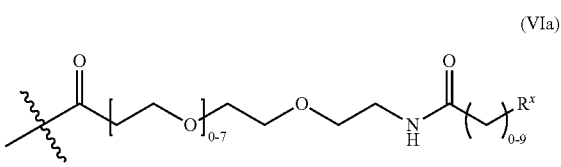

(VIa)

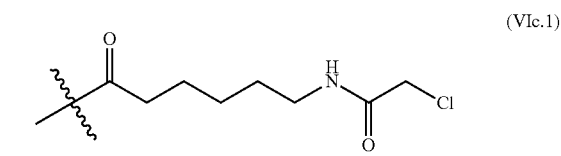

(VIc.1)

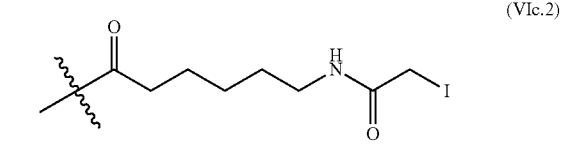

(VIc.2)

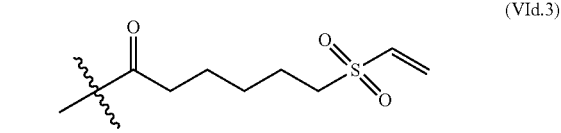

(VId.3)

6.2.5. Groups Used to Attach Linkers to Antibodies

A variety of groups may be used to attach linker-drug synthons to antibodies to yield ADCs. Attachment groups can be electrophilic in nature and include: maleimide groups, activated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure. The specific group used will depend, in part, on the site of attachment to the antibody.

One example of a "self-stabilizing" maleimide group that hydrolyzes spontaneously under antibody conjugation conditions to give an ADC species with improved stability is depicted in the schematic below. See US20130309256 A1; also Lyon et al., Nature Biotech published online, doi: 10.1038/nbt.2968.

Normal System:

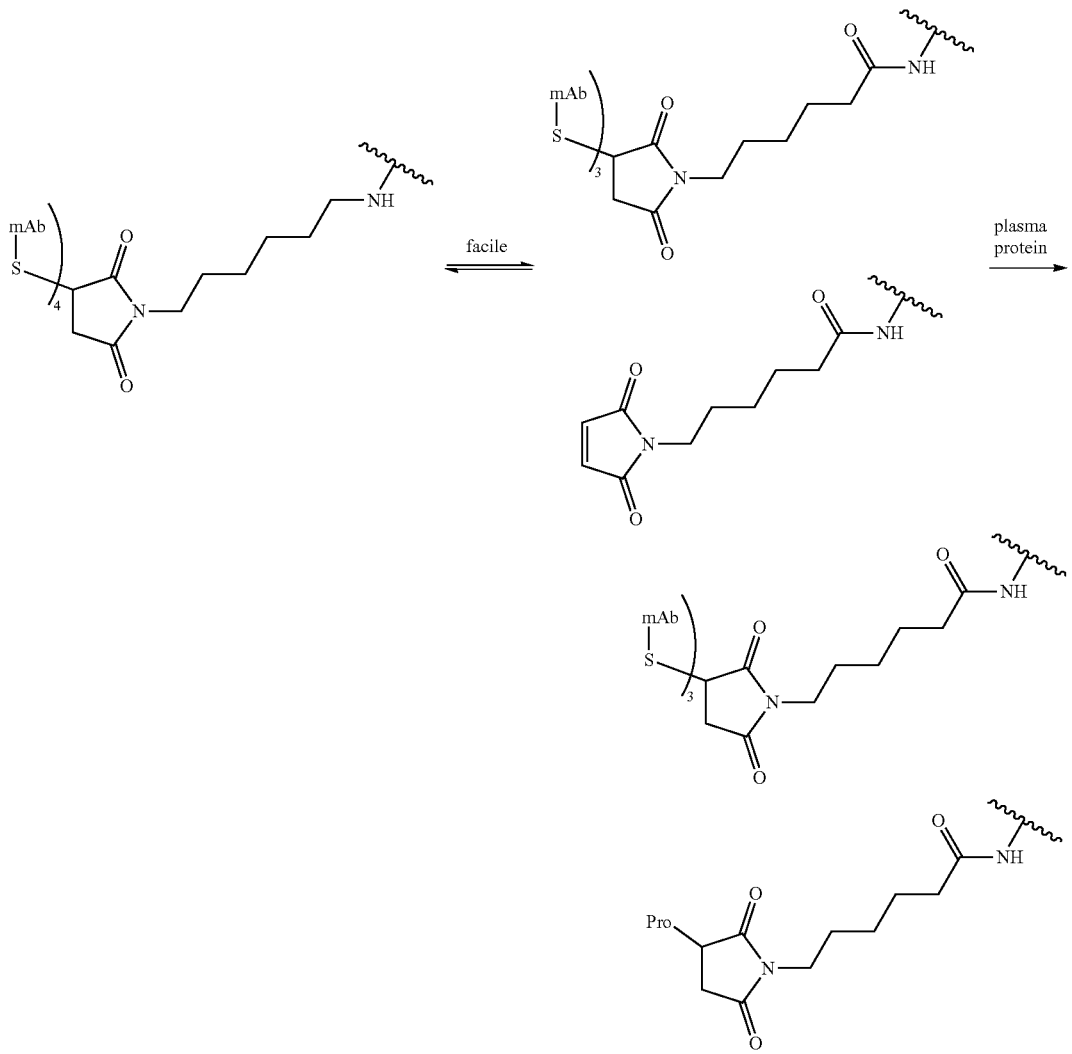

Leads to "DAR loss" over time

SGN MalDPR (Maleimido Dipropylamino) System:

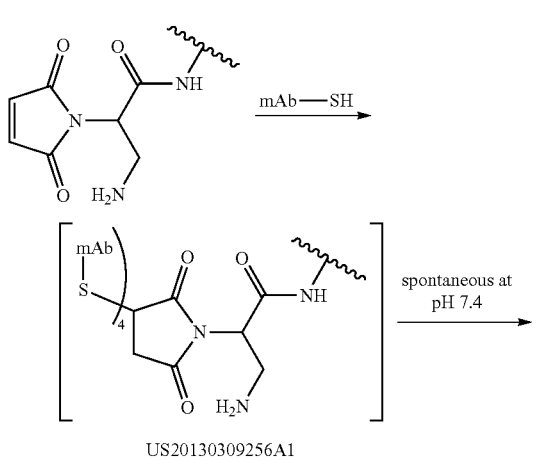

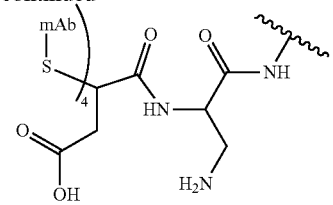

stable in plasma
(retro hetero-Michael
reaction shown above slow)

Polytherics has disclosed a method for bridging a pair of sulfhydryl groups derived from reduction of a native hinge disulfide bond. See, Badescu et al., 2014, Bioconjugate Chem. 25:1124-1136. The reaction is depicted in the schematic below. An advantage of this methodology is the ability to synthesize enriched DAR4 ADCs by full reduction of IgGs (to give 4 pairs of sulfhydryls) followed by reaction with 4 equivalents of the alkylating agent. ADCs containing "bridged disulfides" are also claimed to have increased stability.

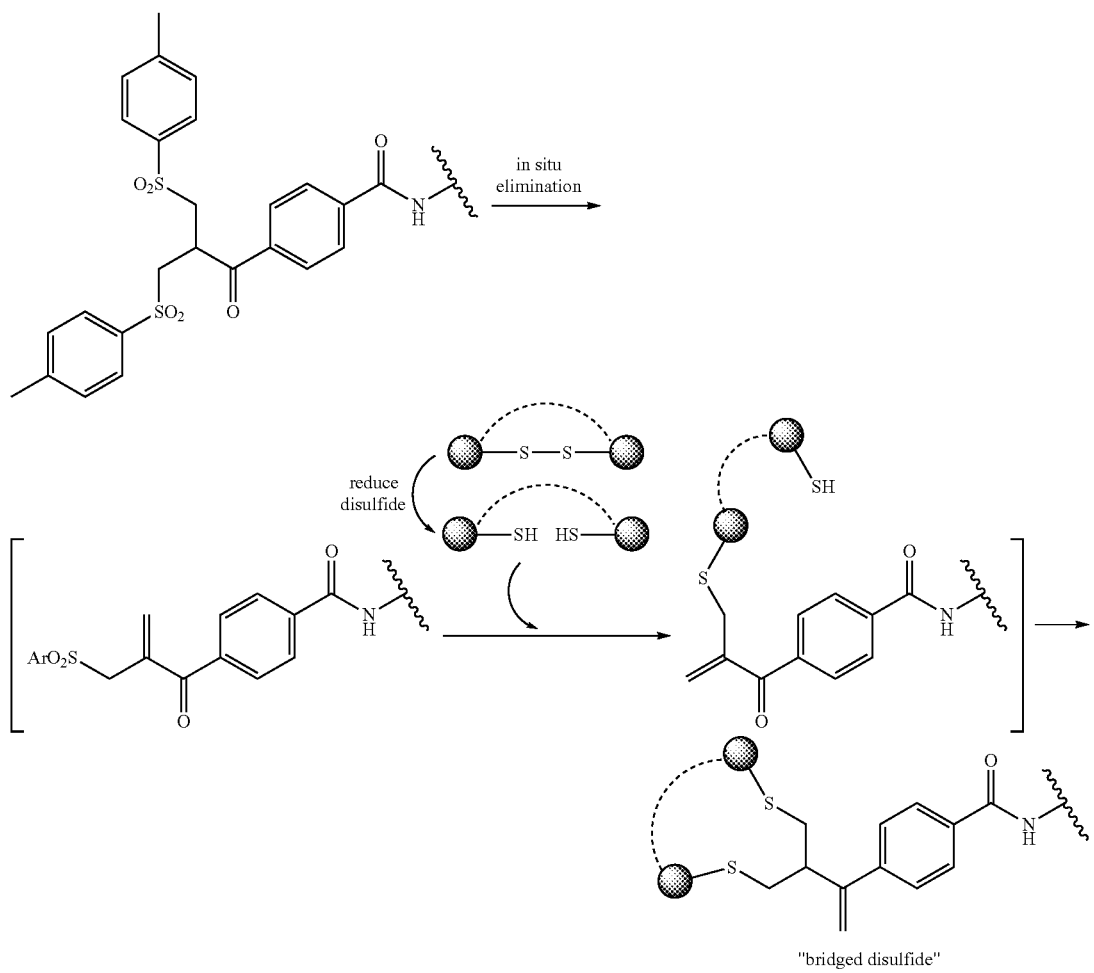

Similarly, as depicted below, a maleimide derivative (1, below) that is capable of bridging a pair of sulfhydryl groups has been developed. See WO2013/085925.

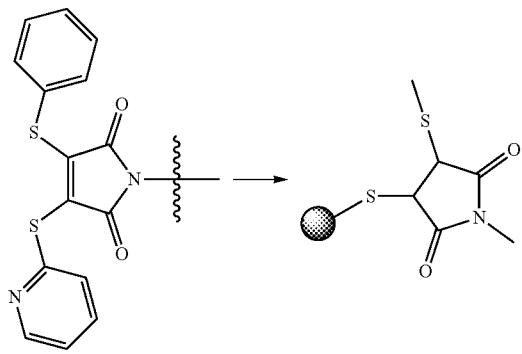 [SMILES: *N1C(=O)C(Sc2ccccc2)=C(Sc2ccccn2)C1=O ; CSC1C(=O)N(C)C(=O)C1SC]

6.2.6. Linker Selection Considerations

As is known by skilled artisans, the linker selected for a particular ADC may be influenced by a variety of factors, including but not limited to, the site of attachment to the antibody (e.g., lys, cys or other amino acid residues), structural constraints of the drug pharmacophore and the lipophilicity of the drug. The specific linker selected for an ADC should seek to balance these different factors for the specific antibody/drug combination. For a review of the factors that are influenced by choice of linkers in ADCs, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013.

For example, ADCs have been observed to effect killing of bystander antigen-negative cells present in the vicinity of the antigen-positive tumor cells. The mechanism of bystander cell killing by ADCs has indicated that metabolic products formed during intracellular processing of the ADCs may play a role. Neutral cytotoxic metabolites generated by metabolism of the ADCs in antigen-positive cells appear to play a role in bystander cell killing while charged metabolites may be prevented from diffusing across the membrane into the medium and therefore cannot affect bystander killing. In certain embodiments, the linker is selected to attenuate the bystander killing effect caused by cellular metabolites of the ADC. In certain embodiments, the linker is selected to increase the bystander killing effect.

The properties of the linker may also impact aggregation of the ADC under conditions of use and/or storage. Typically, ADCs reported in the literature contain no more than 3-4 drug molecules per antibody molecule (see, e.g., Chari, 2008, Acc Chem Res 41:98-107). Attempts to obtain higher drug-to-antibody ratios ("DAR") often failed, particularly if both the drug and the linker were hydrophobic, due to aggregation of the ADC (King et al., 2002, J Med Chem 45:4336-4343; Hollander et al., 2008, Bioconjugate Chem 19:358-361; Burke et al., 2009 Bioconjugate Chem 20:1242-1250). In many instances, DARs higher than 3-4 could be beneficial as a means of increasing potency. In instances where the cytotoxic and/or cytostatic agent is hydrophobic in nature, it may be desirable to select linkers that are relatively hydrophilic as a means of reducing ADC aggregation, especially in instances where DARS greater than 3-4 are desired. Thus, in certain embodiments, the linker incorporates chemical moieties that reduce aggregation of the ADCs during storage and/or use. A linker may incorporate polar or hydrophilic groups such as charged groups or groups that become charged under physiological pH to reduce the aggregation of the ADCs. For example, a linker may incorporate charged groups such as salts or groups that deprotonate, e.g., carboxylates, or protonate, e.g., amines, at physiological pH.

Exemplary polyvalent linkers that have been reported to yield DARs as high as 20 that may be used to link numerous cytotoxic and/or cytostatic agents to an antibody are described in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the content of which are incorporated herein by reference in their entireties.

In particular embodiments, the aggregation of the ADCs during storage or use is less than about 10% as determined by size-exclusion chromatography (SEC). In particular embodiments, the aggregation of the ADCs during storage or use is less than 10%, such as less than about 5%, less than about 4%, less than about 3%, less than about 2%, less than about 1%, less than about 0.5%, less than about 0.1%, or even lower, as determined by size-exclusion chromatography (SEC).

6.2.7. Methods of Making Anti-Glyco-MUC1 ADCs

The anti-glyco-MUC1 ADCs of the disclosure may be synthesized using chemistries that are well-known. The chemistries selected will depend upon, among other things, the identity of the cytotoxic and/or cytostatic agent(s), the linker and the groups used to attach linker to the antibody. Generally, ADCs according to formula (I) may be prepared according to the following scheme:

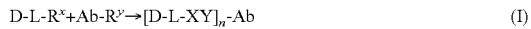

$$D\text{-}L\text{-}R^x + Ab\text{-}R^y \rightarrow [D\text{-}L\text{-}XY]_n\text{-}Ab \quad (I)$$

where D, L, Ab, XY and n are as previously defined, and $R^x$ and $R^y$ represent complementary groups capable of forming a covalent linkages with one another, as discussed above.

The identities of groups $R^x$ and $R^y$ will depend upon the chemistry used to link synthon $D\text{-}L\text{-}R^x$ to the antibody. Generally, the chemistry used should not alter the integrity of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: Monoclonal Antibodies And Cancer Therapy, Reisfeld et al. Eds., Alan R. Liss, Inc., 1985; Hellstrom et al., "Antibodies For Drug Delivery," in: Controlled Drug Delivery, Robinson et al. Eds., Marcel Dekker, Inc., 2nd Ed. 1987; Thorpe, "Antibody Carriers Of Cytotoxic Agents In Cancer Therapy: A Review," in: Monoclonal Antibodies '84: Biological And Clinical Applications, Pinchera et al., Eds., 1985; "Analysis, Results, and Future Prospective of the Therapeutic Use of Radiolabeled Antibody In Cancer Therapy," in: Monoclonal Antibodies For Cancer Detection And Therapy, Baldwin et al., Eds., Academic Press, 1985; Thorpe et al., 1982, Immunol. Rev. 62:119-58; PCT publication WO 89/12624. Any of these chemistries may be used to link the synthons to an antibody.

A number of functional groups $R^x$ and chemistries useful for linking synthons to accessible lysine residues are known, and include by way of example and not limitation NHS-esters and isothiocyanates.

A number of functional groups $R^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups $R^x$ suitable for covalently linking the synthons to these "converted" functional groups are then included in the synthons.

The antibody may also be engineered to include amino acid residues for conjugation. An approach for engineering antibodies to include non-genetically encoded amino acid residues useful for conjugating drugs in the context of ADCs is described by Axup et al., 2012, Proc Natl Acad Sci USA. 109(40):16101-16106, as are chemistries and functional group useful for linking synthons to the non-encoded amino acids.

Typically, the synthons are linked to the side chains of amino acid residues of the antibody, including, for example, the primary amino group of accessible lysine residues or the sulfhydryl group of accessible cysteine residues. Free sulfhydryl groups may be obtained by reducing interchain disulfide bonds.

For linkages where $R^y$ is a sulfhydryl group (for example, when $R^x$ is a maleimide), the antibody is generally first fully or partially reduced to disrupt interchain disulfide bridges between cysteine residues.

Cysteine residues that do not participate in disulfide bridges may engineered into an antibody by mutation of one or more codons. Reducing these unpaired cysteines yields a sulfhydryl group suitable for conjugation. Preferred positions for incorporating engineered cysteines include, by way of example and not limitation, positions S1 12C, S1 13C, A114C, S115C, A176C, S180C, S252C, V286C, V292C, S357C, A359C, S398C, S428C (Kabat numbering) on the human $IgG_1$ heavy chain and positions V110C, S114C, S121C, S127C, S168C, V205C (Kabat numbering) on the human Ig kappa light chain (see, e.g., U.S. Pat. Nos. 7,521,541, 7,855,275 and 8,455,622).

As will appreciated by skilled artisans, the number of cytotoxic and/or cytostatic agents linked to an antibody molecule may vary, such that a collection of ADCs may be heterogeneous in nature, where some antibodies contain one linked agent, some two, some three, etc. (and some none). The degree of heterogeneity will depend upon, among other things, the chemistries used for linking the cytotoxic and/or cytostatic agents. For example, where the antibodies are reduced to yield sulfhydryl groups for attachment, heterogeneous mixtures of antibodies having zero, 2, 4, 6 or 8 linked agents per molecule are often produced. Furthermore, by limiting the molar ratio of attachment compound, antibodies having zero, 1, 2, 3, 4, 5, 6, 7 or 8 linked agents per molecule are often produced. Thus, it will be understood that depending upon context, stated DARs may be averages for a collection of antibodies. For example, "DAR4" can refer to an ADC preparation that has not been subjected to purification to isolate specific DAR peaks and can comprise a heterogeneous mixture of ADC molecules having different numbers of cytostatic and/or cytotoxic agents attached per antibody (e.g., 0, 2, 4, 6, 8 agents per antibody), but has an average drug-to-antibody ratio of 4. Similarly, in some embodiments, "DAR2" refers to a heterogeneous ADC preparation in which the average drug-to-antibody ratio is 2.

When enriched preparations are desired, antibodies having defined numbers of linked cytotoxic and/or cytostatic agents may be obtained via purification of heterogeneous mixtures, for example, via column chromatography, e.g., hydrophobic interaction chromatography.

Purity may be assessed by a variety of methods, as is known in the art. As a specific example, an ADC preparation may be analyzed via HPLC or other chromatography and the purity assessed by analyzing areas under the curves of the resultant peaks.

6.3 Chimeric Antigen Receptors

The present disclosure provides chimeric antigen receptors (CARs) comprising the anti-glyco-MUC1 antibodies or antigen-binding fragments described herein.

The CARs of the disclosure typically comprise an extracellular domain operably linked to a transmembrane domain which is in turn operably linked to an intracellular domain for signaling.

The extracellular domains of the CARs of the disclosure comprise the sequence of an anti-glyco-MUC1 antibody or antigen-binding fragment (e.g., as described in Section 6.1 or embodiments 1 to 145).

Exemplary transmembrane domain sequence and intracellular domain sequences are described in Section 6.3.1 and 6.3.2, respectively.

Several fusion proteins described herein (e.g., embodiments 152 and 153) are CARs, and the CAR-related disclosures apply to such fusion proteins.

6.3.1. Transmembrane Domain

With respect to the transmembrane domain, the CAR can be designed to comprise a transmembrane domain that is operably linked (e.g., fused) to the extracellular domain of the CAR.

The transmembrane domain may be derived either from a natural or from a synthetic source. Where the source is natural, the domain may be derived from any membrane-bound or transmembrane protein. Transmembrane regions of particular use in this disclosure may be derived from (i.e., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain is synthetic (i.e., non-naturally occurring). Examples of synthetic transmembrane domains are peptides comprising predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the disclosure is the CD8 transmembrane domain. In one embodiment, the CD8 transmembrane domain comprises the amino acid sequence YLHLGAL-GRDLWGPSPVTGYHPLL (SEQ ID NO:102).

In one embodiment, the transmembrane domain in the CAR of the disclosure is the CD28 transmembrane domain. In one embodiment, the CD28 transmembrane domain comprises the amino acid sequence FWVLVVVGGVLACYS-LLVTVAFIIFWV (SEQ ID NO:103).

In some instances, the transmembrane domain of the CAR of the disclosure comprises the CD8a hinge domain. In one embodiment, the CD8a hinge domain comprises the amino acid sequence TTTPAPRPPTPAPTIASQPLSLRPEACR-PAAGGAVHTRGLDFAC (SEQ ID NO:104).

6.3.2. Intracellular Domain

The intracellular signaling domain of the CAR of the disclosure is responsible for activation of at least one of the normal effector functions of the immune cell in which the CAR is expressed. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through the TCR alone may be insufficient for full activation of the T cell and a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs of the disclosure include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the disclosure comprises a cytoplasmic signaling sequence from CD3-zeta.

In a preferred embodiment, the cytoplasmic domain of the CAR is designed to include an ITAM containing primary cytoplasmic signaling sequences domain (e.g., that of CD3-zeta) by itself or combined with any other desired cytoplasmic domain(s) useful in the context of the CAR of the disclosure. For example, the cytoplasmic domain of the CAR can include a CD3 zeta chain portion and a costimulatory signaling region.

The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1 BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR of the disclosure may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB.

6.4 Nucleic Acids, Recombinant Vectors and Host Cells

The present disclosure encompasses nucleic acid molecules encoding immunoglobulin light and heavy chain genes for anti-glyco-MUC1 antibodies, vectors comprising such nucleic acids, and host cells capable of producing the anti-glyco-MUC1 antibodies of the disclosure. In certain aspects, the nucleic acid molecules encode, and the host cells are capable of expressing, the anti-glyco-MUC1 antibodies and antibody-binding fragments of the disclosure (e.g., as described in Section 6.1 and embodiments 1 to 145) as well as fusion proteins (e.g., as described in embodiments 146-151) and chimeric antigen receptors (e.g., as described in Section 6.3 and embodiments 152-153) containing them. Exemplary vectors of the disclosure are described in embodiments 166-168 and exemplary host cells are described in embodiments 169-172.

An anti-glyco-MUC1 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel, F. M. et al., eds., Greene Publishing Associates, 1989) and in U.S. Pat. No. 4,816,397.

To generate nucleic acids encoding such anti-glyco-MUC1 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-glyco-MUC1 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_H$- or $V_L$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region.

To create a scFv gene, the $V_H$- and $V_L$-encoding DNA fragments can be operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_H$ and $V_L$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-glyco-MUC1 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-glyco-MUC1 antibody-related light or heavy chain sequences, the expression vector can already carry antibody constant region sequences. For example, one approach to converting the anti-glyco-MUC1 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE—dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-glyco-MUC1 antibody of this disclosure.

For expression of a CAR of the disclosure, for example as described in Section 6.3 and in embodiments 152 and 153, it is preferable that the host cell is a T cell, preferably a human T cell. In some embodiments, the host cell exhibits an anti-tumor immunity when the cell is cross-linked with MUC1 on a tumor cell. Detailed methods for producing the T cells of the disclosure are described in Section 6.4.1

Recombinant DNA technology can also be used to remove some or all of the DNA encoding either or both of the light and heavy chains that is not necessary for binding to glyco-MUC1. The molecules expressed from such truncated DNA molecules are also encompassed by the antibodies of the disclosure.

For recombinant expression of an anti-glyco-MUC1 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-glyco-MUC1 antibody, further alterations or mutations can be introduced into the coding sequence, for example to generate nucleic acids encoding antibodies with different CDR sequences, antibodies with reduced affinity to the Fc receptor, or antibodies of different subclasses.

The anti-glyco-MUC1 antibodies of the disclosure can also be produced by chemical synthesis (e.g., by the methods described in Solid Phase Peptide Synthesis, 2nd ed., 1984 The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-glyco-MUC1 antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-glyco-MUC1 antibodies of the present disclosure and/or binding fragments can be fused to heterologous polypeptide sequences described herein or otherwise known in the art to facilitate purification.

Once isolated, the anti-glyco-MUC1 antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

6.4.1. Recombinant Production of CARs in T Cells

In some embodiments, nucleic acids encoding the anti-glyco-MUC1 CARs of the disclosure are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transponsons.

One advantage of RNA transfection methods of the disclosure is that RNA transfection is essentially transient and a vector-free: an RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly (A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

6.4.1.1 Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. Preferably, subjects are human.

T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art, may be used. In certain embodiments of the present disclosure, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the disclosure, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28'$, $CD4^+$, $CD8^+$, $CD45RA^+$ and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or, lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present disclosure.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAM-PATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation or T cell ablative therapy using either chemotherapy agents such as, fludarabine, external-beam radiation therapy (XRT), cyclophosphamide.

In a further embodiment of the present disclosure, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

6.4.1.2 Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the disclosure are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present disclosure.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present disclosure, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present disclosure, more anti-CD28 antibody is bound to the particles than anti-CD3 antibody, i.e., the ratio of CD3:CD28 is less than one. In certain embodiments of the disclosure, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present disclosure. In particular, ratios will vary depending on particle size and on cell size and type.

In further embodiments of the present disclosure, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 104 to 109 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present disclosure, the mixture may be cultured for several hours (about 3 hours) to about 14 days or any hourly integer value in between. In another embodiment, the mixture may be cultured for 21 days. In one embodiment of the disclosure the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

6.5 Compositions

The anti-glyco-MUC1 antibodies and/or anti-glyco-MUC1 ADCs of the disclosure may be in the form of compositions comprising the anti-glyco-MUC1 antibody and/or ADC and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and/or ADC and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an anti-glyco-MUC1 antibody and/or anti-glyco-MUC1 ADC of the disclosure per dose. The quantity of antibody and/or ADC included in a unit dose will depend on the disease being treated, as well as other factors as are well known in the art. Such unit dosages may be in the form of a lyophilized dry powder containing an amount of antibody and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of antibody and/or ADC suitable for a single administration.

The pharmaceutical compositions may also be supplied in bulk from containing quantities of ADC suitable for multiple administrations.

Pharmaceutical compositions may be prepared for storage as lyophilized formulations or aqueous solutions by mixing an antibody and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of ADC.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.6 Methods of Use

The anti-glyco-MUC1 antibody or binding fragments described herein can be used in various diagnostic assays. For example, the antibodies and binding fragments can be employed in immunoassays, such as competitive binding assays, direct and indirect sandwich assays, and immunoprecipitation assays, including immunohistochemistry, enzyme-linked immunosorbent assay (ELISA), fluorescence-activated cell sorting (FACS), and Western blots.

The anti-glyco-MUC1 antibody or binding fragments described herein also are useful for radiographic in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies.

The anti-glyco-MUC1 antibody or binding fragments, ADCs and CARs described herein are useful for treatment of glyco-MUC1 expressing cancers, including bladder cancer, lung cancer, brain cancer, breast cancer, non-Hodgkin's lymphoma, cervical cancer, ovarian cancer; colorectal cancer, gastric cancer, cholangiocarcinoma, chondrosarcoma, pancreatic cancer, esophageal cancer, prostate cancer, kidney cancer, skin cancer, leukemia, thyroid cancer, liver cancer, uterine cancer, and cervical cancer. In some embodiments, the cancer is an epithelial cancer such as breast cancer, ovarian cancer, pancreatic cancer, or lung cancer.

Thus, the disclosure provides anti-glyco-MUC1 antibodies, binding fragments, ADCs, and CARs as described herein for use as a medicament, for example for use in the treatment of cancer, e.g., any of the cancers identified in the previous paragraph, for use in a diagnostic assay, and for use in radiographic in vivo imaging. The disclosure further provides for the use of the anti-glyco-MUC1 antibodies, binding fragments, ADCs and CARs as described herein in the manufacture of a medicament, for example for the treatment of cancer, e.g., any of the cancers identified in the previous paragraph.

When using the CARs of the disclosure for therapy, the therapeutic methods of the disclosure comprise administering to a subject with a glyco-MUC1-expressing tumor an effective amount of a genetically modified cell engineered to express a CAR of the disclosure, for example as described in Section 6.3 or in embodiment 152 or embodiment 153. Methods of modifying cells, particularly T cells, to express a CAR, are described in Section 6.4.1.

7. EXAMPLES 7.1 Example 1: Identification of Anti-Glyco-Muc1 Antibodies 7.1.1. Materials and Methods
7.1.1.1 Synthesis of Tn MUC1 glycopeptide GST-MUC1 15-mer (Biotin-RPAPGSTAPPAHGVT) (SEQ ID NO:99) peptide was synthesized using standard synthetic peptide chemistry and F-MOC-GalNAc-Ser/Thr for sites of glycosylation to provide a peptide having GalNAc present on the serine and threonine residues identified with bold underlined text, as originally reported by Fontenot et al., 1993, Pept. Res. 6:330-336. This glycopeptide is sometimes referred to herein as "GSTA." Control peptide 70-MUC1 (Biotin-RPAPGSTAPPAHGVT) (SEQ ID NO:99), with no glycosylations, was used for screening. Purified glycopeptides were characterized by MALDI-TOF mass spectrometry on a Voyager DE or Voyager DE Pro MALDI-TOF mass spectrometer (PerSeptive Biosystems) equipped with delayed extraction. The MALDI matrix was 2,5-dihydroxybenzoic acid 10 g/L (Aldrich, Milwaukee, WI) dissolved in 2:1 mixture of 0.1% TFA in 30% aqueous acetonitrile. Samples dissolved in 0.1% TFA to a concentration of ~1 pmol/μL were prepared for analysis by placing 1 μL of sample solution on a probe tip followed by 1 μL of matrix. All mass spectra were obtained in the linear mode. Data processing was carried out using GRAMS/386 software (Galactic Industries, Salem, NH).

7.1.1.2 Immunization Protocol

The GST-glycopeptide was coupled to KLH (Pierce, Rockford, IL) using glutaraldehyde. Efficiency of conjugation was assessed by analyzing the reaction by size exclusion chromatography on a PD-10 column using anti-MUC1 ELISA of fractions. Essentially all reactivity was found with the excluded fraction and insignificant reactivity in the included fractions expected to contain peptides. Further evaluation included comparative titration analysis of the KLH conjugate with the corresponding glycopeptide in ELISA. Both analyses indicated that the conjugation was near complete, which should result in a KLH to glycopeptide ratio of 1:300. Female Balb/c wild-type mice were injected subcutaneously with 10 or 15 μg of (glyco)peptide in a total volume of 200 μL (1:1 mix with Freunds adjuvant, Sigma). Mice received four immunizations 14 days apart, and blood samples were obtained by tail or eye bleeding 1 week following the third and fourth immunization.

7.1.1.3 Generation of Mouse MAb Anti-Tn-MUC1

MAbs from the wild-type Balb/c mice immunized with GST-MUC1 glycopeptide coupled to KLH were screened using glycopeptide ELISA followed by immunocytology with breast cancer cell lines (MCF7 and T47D) and immunohistology with cancer tissues. Selection was based on reactivity pattern similar to total sera of the same mouse. Two antibodies, 1AG and 4AG, were selected for further characterization.

7.2 Example 2: Functional Characterization of 1AG and 4AG Antibodies by ELISA

7.2.1. Overview

1AG and 4AG were characterized by indirect ELISA to test the reactivity of anti-MUC1 mAbs to titrated MUC1 peptides that have different glycosylated sites (including a non-glycosylated peptide) as shown in Table 4.

TABLE 4

| Peptide | Sequence (Bold and Underlined = GalNAc Site) |
|---|---|
| C2 | RPAPGSTAPPAHGVT (SEQ ID NO: 99) |
| C3 | RPAPGSTAPPAHGVT (SEQ ID NO: 99) |
| C4 | RPAPGSTAPPAHGVT (SEQ ID NO: 99) |
| GST | Biotin-RPAPGSTAPPAHGVT (SEQ ID NO: 99) |
| 70 | Biotin-RPAPGSTAPPAHGVT (SEQ ID NO: 99) |

7.2.2. Materials and Methods

ELISA plates were coated with MUC1 peptides titrated in 0.2 M bicarbonate buffer, pH 9.4 over night in concentrations ranging from 0.08 µg/ml to 10 µg/ml. BSA was used as a control/measure of background. The plates were then blocked with SuperBlock™ (Thermo Fisher) for 1 hr at room temperature. After plate washing, 1AG and 4AG hybridoma supernatants were incubated on the ELISA plate for 1 hour. The plates were then washed, and then incubated with secondary antibody (1/3000 Goat Anti-mouse IgG (H+L) HRP (abcam 62-6520)) for 1 hour. The plate was then washed and color was developed with 1-Step™ Ultra TMB (Thermo Fisher) for 2 minutes. Color development was then stopped with 2 N Sulfuric Acid. Absorbance at 450 nm was then measured.

7.2.3. Results

Results are shown in FIG. 1A to FIG. 1F and FIG. 2A to FIG. 2B. As shown in the figures, 1AG and 4AG specifically bind to glycosylated peptides C3, C4 and GST, but do not bind to glycosylated peptide C2 or non-glycosylated peptide 70.

7.3 Example 3: Functional Characterization of 1AG and 4AG Antibodies by Antibody Titration 1AG and 4AG were characterized by an antibody titration assay against a constant concentration of the antigen GSTA.

Results are shown in FIG. 3.

7.4 Example 4: Functional Characterization of 1AG and 4AG Antibodies by Surface Plasmon Resonance

7.4.1. Materials and Methods

Binding of the 1AG and 4AG antibodies to one glycysolated and one non-glycosylated peptide (Table 5) was assessed by surface plasmon resonance (SPR).

TABLE 5

| Peptide | Sequence (Bold and underlined = GalNAc Site) |
|---|---|
| Glycosylated | RPAPGSTAPPAHGVT (SEQ ID NO: 99) |
| Non-Glycosylated | RPAPGSTAPPAHGVT (SEQ ID NO: 99) |

All SPR experiments were performed on a Biacore T200 with a CM5 sensor chip with 10,000 RU anti-mouse antibody on each channel (GE Healthcare) at 25° C. with HBS-P+ as running and sample buffer (10 mM HEPES pH 7.4, 150 mM NaCl, 0.05% Tween 20, and 1 mg/ml BSA) and 10 mM glycine, pH 1.7 as regeneration buffer.

The 1AG and 4AG antibodies were immobilized as a 30 µg/mL solution in 10 mM sodium acetate, pH 5.0 using standard amine coupling chemistry (EDC/NHS activation). Antibody capture was performed using a 10× dilution into reaction buffer for 7 to 10 minutes at 5 µL/min. Immobilization levels of 600 to 1000 RU were used. Peptide samples were prepared as two-fold dilution series with the starting concentration of 100 nM in the running buffer (6.25 nM, 12.5 nM, 25 nM, 50 nM, and 100 nM) and injected in a single-cycle injection at 50 µL/min for 2 minutes. The dissociation was monitored for 5 minutes to 30 minutes.

7.4.2. Results

Results are shown in Table 6. As shown in Table 6, the affinity of 1AG for the glycosylated peptide is in the two digit nanomolar range and the affinity of 4AG for the glycosylated peptide is in the single digit nanomolar range.

TABLE 6

| Antibody | peptide | $k_a$ (1/Ms) | $k_d$ (1/s) | $K_D$ (M) | % Rmax/Rmax theoretical |
|---|---|---|---|---|---|
| 1AG | Glyco | 1.79e5 | 7e−3 | 3.73e−8 | 67 |
| 1AG | Non-Glyco | NB | NB | NB | NA |
| 4AG | Glyco | 2.72e5 | 9.3e−4 | 3.4e−9 | 84 |
| 4AG | Non-Glyco | NB | NB | NB | NA |

$K_a$-association rate constant
$K_d$-dissociation rate constant
$K_D$-equilibrium dissociation constant

7.5 Example 5: Sequence Analysis of Anti-Glyco-Muc1 Antibodies

Rapid Amplification of cDNA Ends (RACE) was performed to determine the heavy chain and light chain nucleotide sequences for 1AG and 4AG.

The nucleotide sequences encoding the heavy and light chain variable regions of 1AG are set forth in SEQ ID NO:21 and SEQ ID NO:22, respectively. The heavy and light chain variable regions encoded by SEQ ID NO:21 and SEQ ID NO:22 are set forth in SEQ ID NO:1 and SEQ ID NO:2, respectively. The predicted heavy chain CDR sequences (IMGT definition) are set forth in SEQ ID NOs: 3-5, respectively, and the predicted light chain CDR sequences (IMGT definition) are set forth in SEQ ID NOs: 6-8, respectively. The predicted heavy chain CDR sequences (Kabat definition) are set forth in SEQ ID NOs:9-11, respectively, and the predicted light chain CDR sequences (Kabat definition) are set forth in SEQ ID NOs:12-14, respectively. The predicted heavy chain CDR sequences (Chothia definition) are set forth in SEQ ID NOs:15-17, respectively, and the predicted light chain CDR sequences (Chothia definition) are set forth in SEQ ID NOs:18-20, respectively.

The nucleotide sequences encoding the heavy and light chain variable regions of 4AG are set forth in SEQ ID NO:43 and SEQ ID NO:44, respectively. The heavy and light chain variable regions encoded by SEQ ID NO:43 and SEQ ID NO:44 are set forth in SEQ ID NO:23 and SEQ ID NO:24, respectively. The predicted heavy chain CDR sequences (IMGT definition) are set forth in SEQ ID NOs: 25-27, respectively, and the predicted light chain CDR sequences (IMGT definition) are set forth in SEQ ID NOs: 28-30, respectively. The predicted heavy chain CDR sequences (Kabat definition) are set forth in SEQ ID NOs: 31-33, respectively, and the predicted light chain CDR sequences (Kabat definition) are set forth in SEQ ID NOs: 34-36, respectively. The predicted heavy chain CDR sequences (Chothia definition) are set forth in SEQ ID NOs:37-39, respectively, and the predicted light chain CDR sequences (Chothia definition) are set forth in SEQ ID NOs:40-42, respectively.

7.6 Example 6: Immunohistochemical Staining of Various Tumor Tissues Using Anti-Glyco-Muc1 Antibodies

7.6.1. Materials and Methods

Human tissue micro array (TMA) BCN721a (US Biomax) was used to screen antibodies 1AG and 4AG for their ability to stain various tumor tissues. The TMA contained tissue samples from 12 types of human organs, including esophagus, stomach, colon, rectum, liver, lung, kidney, breast, uterine cervix, ovary, prostate and pancreas, each type taken from three normal human individuals, single core per case.

The identity of each tissue in the TMA is set forth in Table 7.

TABLE 7

| Position | Age | Sex | Organ (Anatomic Site) | Pathology diagnosis | TNM | Grade | Stage | Type |
|---|---|---|---|---|---|---|---|---|
| A1 | 62 | M | Esophagus | Squamous cell carcinoma | T3N1M0 | 2 | IIIA | Malignant |
| A2 | 56 | M | Esophagus | Squamous cell carcinoma | T3N0M0 | 2 | IIA | Malignant |
| A3 | 72 | F | Esophagus | Squamous cell carcinoma | T2N0M0 | — | IIA | Malignant |
| A4 | 74 | M | Stomach | Adenocarcinoma | T3N1M0 | 3 | IIIA | Malignant |
| A5 | 56 | M | Stomach | Adenocarcinoma | T3N1M0 | 3 | IIIA | Malignant |
| A6 | 55 | F | Stomach | Adenocarcinoma | T3N3M0 | 3 | IIIC | Malignant |
| A7 | 67 | M | Colon | Adenocarcinoma | T3N0M0 | 1 | IIA | Malignant |
| A8 | 58 | M | Colon | Adenocarcinoma | T4N1M1 | 2 | IV | Malignant |
| A9 | 37 | M | Colon | Adenocarcinoma | T4N1M0 | 2 | IIIC | Malignant |
| B1 | 38 | M | Esophagus | Cancer adjacent esophagus tissue | — | — | — | AT |
| B2 | 64 | M | Esophagus | Cancer adjacent esophagus tissue | | — | — | AT |
| B3 | 48 | M | Esophagus | Cancer adjacent esophagus tissue | — | — | — | AT |
| B4 | 54 | M | Stomach | Cancer adjacent stomach tissue | — | — | — | AT |
| B5 | 54 | M | Stomach | Cancer adjacent stomach tissue | — | — | — | AT |
| B6 | 64 | F | Stomach | Cancer adjacent stomach tissue | — | — | — | AT |
| B7 | 56 | F | Colon | Cancer adjacent colon tissue | — | — | — | AT |
| B8 | 70 | F | Colon | Cancer adjacent colon tissue | — | — | — | AT |
| B9 | 64 | F | Colon | Cancer adjacent colon tissue | — | — | — | AT |
| C1 | 55 | M | Rectum | Adenocarcinoma | T3N0M0 | 1 | IIA | Malignant |
| C2 | 67 | M | Rectum | Adenocarcinoma | T4N0M0 | 2 | IIB | Malignant |
| C3 | 44 | F | Rectum | Adenocarcinoma | T3N1M0 | 3 | IIIB | Malignant |
| C4 | 32 | F | Liver | Hepatocellular carcinoma | T3N0M0 | 1 | IIIA | Malignant |
| C5 | 40 | M | Liver | Hepatocellular carcinoma | T3N1M0 | 2 | IVA | Malignant |
| C6 | 55 | F | Liver | Hepatocellular carcinoma | T3N0M0 | 2 | IIIA | Malignant |
| C7 | 66 | M | Lung | Squamous cell carcinoma | T2N0M0 | 2 | I | Malignant |
| C8 | 55 | M | Lung | Squamous cell carcinoma | T2N1M0 | 2 | IIB | Malignant |
| C9 | 55 | M | Lung | Squamous cell carcinoma | T2N1M0 | 2 | IIA | Malignant |
| D1 | 43 | F | Rectum | Cancer adjacent rectum tissue | — | — | — | AT |
| D2 | 52 | M | Rectum | Cancer adjacent rectum tissue | — | — | — | AT |

TABLE 7-continued

| Position | Age | Sex | Organ (Anatomic Site) | Pathology diagnosis | TNM | Grade | Stage | Type |
|---|---|---|---|---|---|---|---|---|
| D3 | 67 | M | Rectum | Cancer adjacent rectum tissue | — | — | — | AT |
| D4 | 63 | M | Liver | Cancer adjacent liver tissue | — | — | — | AT |
| D5 | 55 | M | Liver | Cancer adjacent liver tissue | — | — | — | AT |
| D6 | 56 | M | Liver | Cancer adjacent liver tissue | — | — | — | AT |
| D7 | 68 | F | Lung | Cancer adjacent lung tissue | — | — | — | AT |
| D8 | 65 | M | Lung | Cancer adjacent lung tissue | — | — | — | AT |
| D9 | 68 | M | Lung | Cancer adjacent lung tissue | — | — | — | AT |
| E1 | 70 | M | Kidney | Clear cell carcinoma | T1N0M0 | 1 | I | Malignant |
| E2 | 46 | M | Kidney | Clear cell carcinoma | T1N0M0 | 1 | I | Malignant |
| E3 | 82 | M | Kidney | Clear cell carcinoma | T1N0M0 | 2 | I | Malignant |
| E4 | 29 | F | Breast | Invasive ductal carcinoma | T2N0M0 | 1 | IIA | Malignant |
| E5 | 51 | F | Breast | Invasive ductal carcinoma | T4N0M0 | 2 | IIIB | Malignant |
| E6 | 63 | F | Breast | Invasive ductal carcinoma | T2N0M0 | 3 | IIA | Malignant |
| E7 | 45 | F | Uterine cervix | Squamous cell carcinoma | T2N0M0 | 2 | II | Malignant |
| E8 | 76 | F | Uterine cervix | Squamous cell carcinoma | T2N0M0 | 2 | II | Malignant |
| E9 | 47 | F | Uterine cervix | Squamous cell carcinoma | T2N0M0 | 2 | II | Malignant |
| F1 | 54 | M | Kidney | Cancer adjacent kidney tissue | — | — | — | AT |
| F2 | 56 | M | Kidney | Cancer adjacent kidney tissue | — | — | — | AT |
| F3 | 61 | F | Kidney | Cancer adjacent kidney tissue | — | — | — | AT |
| F4 | 43 | F | Breast | Cancer adjacent breast tissue | — | — | — | AT |
| F5 | 38 | F | Breast | Cancer adjacent breast tissue | — | — | — | AT |
| F6 | 41 | F | Breast | Cancer adjacent breast duct tissue | — | — | — | AT |
| F7 | 39 | F | Uterine cervix | Cancer adjacent cervical canals tissue | — | — | — | AT |
| F8 | 25 | F | Uterine cervix | Cancer adjacent cervical canals tissue | — | — | — | AT |
| F9 | 49 | F | Uterine cervix | Cancer adjacent cervical canals tissue | — | — | — | AT |
| G1 | 55 | F | Ovary | Serous papillary adenocarcinoma | T1AN0M0 | 2 | IA | Malignant |
| G2 | 49 | F | Ovary | Serous adenocarcinoma | T2N0M0 | 3 | II | Malignant |
| G3 | 48 | F | Ovary | Serous adenocarcinoma | T1BN0M0 | 3 | IB | Malignant |
| G4 | 76 | M | Prostate | Adenocarcinoma | T3N0M0 | 2 | III | Malignant |
| G5 | 80 | M | Prostate | Adenocarcinoma | T3N0M0 | 2 | III | Malignant |
| G6 | 82 | M | Prostate | Adenocarcinoma | T2N0M0 | 3 | IIA | Malignant |
| G7 | 55 | M | Pancreas | Duct adenocarcinoma | T3N0M0 | 2 | II | Malignant |
| G8 | 65 | M | Pancreas | Duct adenocarcinoma | T3N0M0 | 2 | IIA | Malignant |
| G9 | 68 | F | Pancreas | Duct adenocarcinoma | T2N0M0 | 2 | IB | Malignant |
| H1 | 53 | F | Ovary | Cancer adjacent ovary tissue | — | — | — | AT |
| H2 | 45 | F | Ovary | Cancer adjacent ovary tissue | — | — | — | AT |
| H3 | 40 | F | Ovary | Cancer adjacent ovary tissue | — | — | — | AT |
| H4 | 63 | M | Prostate | Cancer adjacent prostate tissue | — | — | — | AT |

TABLE 7-continued

| Position | Age | Sex | Organ (Anatomic Site) | Pathology diagnosis | TNM | Grade | Stage | Type |
|---|---|---|---|---|---|---|---|---|
| H5 | 52 | M | Prostate | Cancer adjacent prostate tissue | — | — | — | AT |
| H6 | 35 | M | Prostate | Cancer adjacent prostate tissue | — | — | — | AT |
| H7 | 69 | F | Pancreas | Cancer adjacent pancreas tissue | — | — | — | AT |
| H8 | 64 | M | Pancreas | Cancer adjacent pancreas tissue | — | — | — | AT |
| H9 | 70 | M | Pancreas | Cancer adjacent pancreas tissue | — | — | — | AT |

AT—adjacent tissue

The sections were fixed in cold 10% buffered neutral formalin for 15 min. Immunohistochemistry (IHC) was performed by incubation of slides for 24 hours at 4° C. or 2 hours at room temperature with undiluted hybridoma supernatant or purified Mabs (1AG and 4AG). Bound mAbs were detected with FITC-conjugated rabbit anti-mouse immunoglobulin (1:100; Dako, Denmark) or peroxidase conjugated rabbit anti-mouse immunoglobulin. Slides were mounted with Prolong Gold antifade reagent with DAPI (Invitrogen), and micrographs were obtained on a Leica wide-field fluorescence microscope.

7.6.2. Results

Results for 1AG are shown in FIG. 4. Results for 4AG are shown in FIG. 5. mAb and 1AG and mAb 4AG reacted specifically with the majority of the examined cancer tissues. Staining of healthy tissue demonstrated very limited reactivity with surface structures, although some labeling of intracellular structures was seen especially in gastric tissue.

7.7 Example 7: Immunohistochemical Staining of Ovarian Tumor Tissue Using Anti-Glyco-Muc Antibodies 7.7.1. Materials and Methods Human tissue micro array (TMA) OV241c (US Biomax) was used to screen antibodies 1AG and 4AG for their ability to stain ovarian tumor tissues.

The identity of each tissue in the TMA is set forth in Table 8.

TABLE 8

| Position | Age | Sex | Organ (Anatomic Site) | Pathology diagnosis | TNM | Grade | Stage | Type |
|---|---|---|---|---|---|---|---|---|
| A1 | 26 | F | Ovary | Serous papillary adenocarcinoma | T1CN0M0 | 1 | | Malignant |
| A2 | 26 | F | Ovary | Serous papillary adenocarcinoma | T1CN0M0 | 1 | | Malignant |
| A3 | 44 | F | Ovary | Adjacent normal ovary tissue | — | — | | NAT |
| A4 | 44 | F | Ovary | Adjacent normal ovary tissue | — | — | | NAT |
| A5 | 55 | F | Ovary | Serous papillary adenocarcinoma | T2N1M0 | 2 | | Malignant |
| A6 | 55 | F | Ovary | Serous papillary adenocarcinoma | T2N1M0 | 2 | | Malignant |
| A7 | 45 | F | Ovary | Adjacent normal ovary tissue | — | — | | NAT |
| A8 | 45 | F | Ovary | Adjacent normal ovary tissue | — | — | | NAT |
| B1 | 75 | F | Ovary | Serous papillary adenocarcinoma | T3N1M0 | 1 | | Malignant |
| B2 | 75 | F | Ovary | Serous papillary adenocarcinoma | T3N1M0 | 1 | | Malignant |
| B3 | 44 | F | Ovary | Adjacent normal ovary tissue | — | — | | NAT |
| B4 | 44 | F | Ovary | Adjacent normal ovary tissue | — | — | | NAT |
| B5 | 59 | F | Ovary | Serous papillary adenocarcinoma | T2BN0M0 | 3 | | Malignant |
| B6 | 59 | F | Ovary | Serous papillary adenocarcinoma | T2BN0M0 | 3 | | Malignant |
| B7 | 68 | F | Ovary | Adjacent normal ovary tissue | — | — | | NAT |
| B8 | 68 | F | Ovary | Adjacent normal ovary tissue | — | — | | NAT |
| C1 | 55 | F | Ovary | Serous papillary adenocarcinoma | T1AN0M0 | 3 | | Malignant |
| C2 | 55 | F | Ovary | Serous papillary adenocarcinoma | T1AN0M0 | 3 | | Malignant |
| C3 | 52 | F | Ovary | Adjacent normal ovary tissue | — | — | | NAT |

TABLE 8-continued

| Position | Age | Sex | Organ (Anatomic Site) | Pathology diagnosis | TNM | Grade | Stage | Type |
|---|---|---|---|---|---|---|---|---|
| C4 | 52 | F | Ovary | Adjacent normal ovary tissue | — | — | | NAT |
| C5 | 53 | F | Ovary | Endometrioid adenocarcinoma | T1N0M0 | 2 | | Malignant |
| C6 | 53 | F | Ovary | Endometrioid adenocarcinoma | T1N0M0 | 2 | | Malignant |
| C7 | 46 | F | Ovary | Cancer adjacent ovary tissue | — | — | | AT |
| C8 | 46 | F | Ovary | Cancer adjacent ovary tissue | — | — | | AT |

AT—adjacent tissue
NAT—normal adjacent tissue

The sections were fixed in cold 10% buffered neutral formalin for 15 min. Immunohistochemistry (IHC) was performed by incubation of slides for 24 hours at 4° C. or 2 hours at room temperature with undiluted hybridoma supernatant or purified Mabs (1AG and 4AG). Bound mAbs were detected with FITC-conjugated rabbit anti-mouse immunoglobulin (1:100; Dako, Denmark) or peroxidase conjugated rabbit anti-mouse immunoglobulin. Slides were mounted with Prolong Gold antifade reagent with DAPI (Invitrogen), and micrographs were obtained on a Leica wide-field fluorescence microscope.

7.7.2. Results

Results for 1AG are shown in FIG. 6. Results for 4AG are shown in FIG. 7. mAb 4AG reacted specifically with the majority of the examined tissues from ovarian adenocarcinomas. Staining of adjacent healthy tissue demonstrated some labeling of intracellular structures. No significant labeling was seen with mAb 1AG of ovarian cancer and tumor adjacent tissues under these conditions.

7.8 Example 8: Immunohistochemical Staining of Tumor Tissue Using Anti-Glyco-Muc1 Antibodies 7.8.1. Materials and Methods Human tissue micro array (TMA) BC000119 (US Biomax) was used to screen antibodies 1AG and 4AG for their ability to stain various tumor tissues. The TMA contained 40 cases each of breast invasive ductal carcinoma, lung squamous cell carcinoma, colon adenocarcinoma, prostate adenocarcinoma and pancreas adenocarcinoma. Healthy control samples were evaluated from multiple organ normal tissue array.

The identity of each tissue in the TMA is set forth in Table 9.

TABLE 9

| Position | Age | Sex | Organ (Anatomic Site) | Pathology diagnosis | TNM | Grade | Stage | Type |
|---|---|---|---|---|---|---|---|---|
| A1 | 44 | F | Breast | Invasive ductal carcinoma | T1N0M0 | 1 | I | malignant |
| A2 | 63 | F | Breast | Invasive ductal carcinoma | T4N0M0 | 1 | IIIb | malignant |
| A3 | 40 | F | Breast | Invasive ductal carcinoma | T2N0M0 | 2 | IIa | malignant |
| A4 | 61 | F | Breast | Invasive ductal carcinoma | T2N1M0 | 2 | IIb | malignant |
| A5 | 58 | F | Breast | Invasive ductal carcinoma | T1N0M0 | 1 | I | malignant |
| A6 | 57 | F | Breast | Invasive ductal carcinoma | T4N2M0 | 2 | IIIa | malignant |
| A7 | 53 | F | Breast | Invasive ductal carcinoma | T2N1M0 | 3 | IIb | malignant |
| A8 | 38 | F | Breast | Invasive ductal carcinoma | PT3N1M0 | 3 | IIb | malignant |
| A9 | 40 | F | Breast | Invasive ductal carcinoma (adenosis) | T4N0M0 | — | IIIb | malignant |
| A10 | 63 | F | Breast | Invasive ductal carcinoma | T1N0M0 | 2 | I | malignant |
| A11 | 43 | F | Breast | Invasive ductal carcinoma | T1N0M0 | 2 | I | malignant |
| A12 | 54 | F | Breast | Invasive ductal carcinoma | T3N0M0 | 2 | IIb | malignant |
| A13 | 57 | F | Breast | Invasive ductal carcinoma (fatty tissue) | T2N0M0 | — | IIa | malignant |
| A14 | 51 | F | Breast | Invasive ductal carcinoma | T2N0M0 | 2 | IIa | malignant |
| A15 | 46 | F | Breast | Invasive ductal carcinoma | T1N0M0 | 3 | I | malignant |
| A16 | 49 | F | Breast | Invasive ductal carcinoma | T2N0M0 | 3 | IIa | malignant |

TABLE 9-continued

| Position | Age | Sex | Organ (Anatomic Site) | Pathology diagnosis | TNM | Grade | Stage | Type |
|---|---|---|---|---|---|---|---|---|
| B1 | 36 | F | Breast | Invasive ductal carcinoma | T2N0M0 | 2 | IIa | malignant |
| B2 | 47 | F | Breast | Invasive ductal carcinoma | T2N0M0 | 3 | IIa | malignant |
| B3 | 69 | F | Breast | Invasive ductal carcinoma | T4N0M0 | 3 | IIIb | malignant |
| B4 | 81 | F | Breast | Invasive ductal carcinoma | T4N0M0 | 3 | IIIb | malignant |
| B5 | 57 | F | Breast | Invasive ductal carcinoma | T4N1M0 | 3 | IIIb | malignant |
| B6 | 52 | F | Breast | Invasive ductal carcinoma | T4N1M0 | 3 | IIIb | malignant |
| B7 | 39 | F | Breast | Invasive ductal carcinoma | T4N1M0 | 3 | IIIb | malignant |
| B8 | 42 | F | Breast | Invasive ductal carcinoma (sparse) | T2N0M0 | 2 | IIa | malignant |
| B9 | 45 | F | Breast | Invasive ductal carcinoma (sparse) | T2N0M0 | — | IIa | malignant |
| B10 | 52 | F | Breast | Invasive ductal carcinoma | T2N1M0 | 3 | IIb | malignant |
| B11 | 44 | F | Breast | Invasive ductal carcinoma | T2N1M0 | 2 | IIb | malignant |
| B12 | 38 | F | Breast | Invasive ductal carcinoma | T2N1M0 | 2 | IIb | malignant |
| B13 | 53 | F | Breast | Invasive ductal carcinoma | T3N1M0 | 3 | IIb | malignant |
| B14 | 60 | F | Breast | Invasive ductal carcinoma | T2N0M0 | 3 | IIa | malignant |
| B15 | 39 | F | Breast | Invasive ductal carcinoma | T2N0M0 | 2 | IIa | malignant |
| B16 | 42 | F | Breast | Invasive ductal carcinoma | T2N0M0 | 3 | IIa | malignant |
| C1 | 47 | F | Breast | Invasive ductal carcinoma | T3N0M0 | 2 | IIb | malignant |
| C2 | 31 | F | Breast | Invasive ductal carcinoma | T4N2M0 | 3 | IIIb | malignant |
| C3 | 57 | F | Breast | Invasive ductal carcinoma (fibrofatty tissue) | T2N0M0 | — | IIa | malignant |
| C4 | 60 | F | Breast | Invasive ductal carcinoma | T2N0M0 | 3 | IIa | malignant |
| C5 | 29 | F | Breast | Invasive ductal carcinoma | T2N0M0 | 3 | IIa | malignant |
| C6 | 62 | F | Breast | Invasive ductal carcinoma | T4N0M0 | 3 | IIIb | malignant |
| C7 | 46 | F | Breast | Invasive ductal carcinoma | T2N0M0 | 3 | IIa | malignant |
| C8 | 48 | F | Breast | Invasive ductal carcinoma | T2N0M0 | 3 | IIa | malignant |
| C9 | 54 | M | Lung | Squamous cell carcinoma | T2N0M0 | 1 | I | malignant |
| C10 | 68 | M | Lung | Squamous cell carcinoma | T2N0M0 | 1 | I | malignant |
| C11 | 74 | M | Lung | Squamous cell carcinoma | T3N0M0 | 1 | IIIa | malignant |
| C12 | 44 | M | Lung | Squamous cell carcinoma | T2N1M0 | 2 | II | malignant |
| C13 | 39 | M | Lung | Squamous cell carcinoma | T2N1M0 | 2 | II | malignant |
| C14 | 48 | M | Lung | Squamous cell carcinoma | T2N0M0 | 2 | I | malignant |
| C15 | 65 | M | Lung | Squamous cell carcinoma | T3N0M0 | 1 | IIIa | malignant |
| C16 | 54 | M | Lung | Squamous cell carcinoma | T2N3M0 | 2 | IIIb | malignant |
| D1 | 54 | F | Lung | Squamous cell carcinoma | T2N1M0 | 2 | II | malignant |
| D2 | 59 | M | Lung | Squamous cell carcinoma | T2N1M0 | 2 | II | malignant |
| D3 | 56 | M | Lung | Squamous cell carcinoma | T3N0M0 | 3 | IIIa | malignant |
| D4 | 60 | M | Lung | Squamous cell carcinoma | T2N1M0 | 3 | II | malignant |
| D5 | 74 | M | Lung | Squamous cell carcinoma | T2N1M0 | 2 | II | malignant |

TABLE 9-continued

| Position | Age | Sex | Organ (Anatomic Site) | Pathology diagnosis | TNM | Grade | Stage | Type |
|---|---|---|---|---|---|---|---|---|
| D6 | 68 | M | Lung | Squamous cell carcinoma | T2N1M0 | 3 | II | malignant |
| D7 | 56 | M | Lung | Squamous cell carcinoma (sparse) | T3N0M0 | 2 | IIIa | malignant |
| D8 | 53 | M | Lung | Squamous cell carcinoma | T2N0M0 | 3 | I | malignant |
| D9 | 50 | M | Lung | Squamous cell carcinoma with necrosis | T2N0M0 | 3 | I | malignant |
| D10 | 61 | M | Lung | Squamous cell carcinoma | T2N1M0 | 3 | II | malignant |
| D11 | 47 | M | Lung | Squamous cell carcinoma | T2N1M0 | 2 | II | malignant |
| D12 | 45 | M | Lung | Squamous cell carcinoma | T2N0M0 | 2 | I | malignant |
| D13 | 56 | M | Lung | Squamous cell carcinoma | T2N0M0 | 2 | I | malignant |
| D14 | 65 | M | Lung | Squamous cell carcinoma | T2N0M0 | 2 | I | malignant |
| D15 | 66 | M | Lung | Squamous cell carcinoma | T2N0M0 | 2 | I | malignant |
| D16 | 70 | F | Lung | Squamous cell carcinoma | T2N1M0 | 2 | II | malignant |
| E1 | 63 | M | Lung | Squamous cell carcinoma | T2N1M0 | 3 | II | malignant |
| E2 | 61 | M | Lung | Squamous cell carcinoma with necrosis | T3N1M0 | 3 | IIIa | malignant |
| E3 | 65 | M | Lung | Squamous cell carcinoma | T2N1M0 | 3 | II | malignant |
| E4 | 24 | M | Lung | Squamous cell carcinoma | T2N1M0 | 2 | II | malignant |
| E5 | 60 | M | Lung | Squamous cell carcinoma | T2N0M0 | 2 | I | malignant |
| E6 | 50 | M | Lung | Squamous cell carcinoma | T3N1M0 | 2 | IIIa | malignant |
| E7 | 65 | M | Lung | Squamous cell carcinoma | T2N1M0 | 3 | II | malignant |
| E8 | 69 | M | Lung | Squamous cell carcinoma | T1N0M0 | 3 | I | malignant |
| E9 | 49 | F | Lung | Squamous cell carcinoma (sparse) | T2N1M0 | 3 | II | malignant |
| E10 | 71 | M | Lung | Squamous cell carcinoma | T2N1M0 | 3 | II | malignant |
| E11 | 69 | M | Lung | Squamous cell carcinoma | T2N0M0 | 3 | I | malignant |
| E12 | 49 | M | Lung | Squamous cell carcinoma | T2N0M0 | 3 | I | malignant |
| E13 | 61 | M | Lung | Squamous cell carcinoma | T2N0M0 | 3 | I | malignant |
| E14 | 63 | M | Lung | Squamous cell carcinoma | T3N1M0 | 3 | IIIa | malignant |
| E15 | 68 | M | Lung | Squamous cell carcinoma | T3N0M0 | 3 | IIIa | malignant |
| E16 | 59 | M | Lung | Squamous cell carcinoma | T2N1M0 | 3 | II | malignant |
| F1 | 37 | F | Colon | Mucinous adenocarcinoma | T4N2M0 | 1 | III | malignant |
| F2 | 68 | F | Colon | Mucinous adenocarcinoma | T3N1M0 | 1 | II | malignant |
| F3 | 45 | F | Colon | Papillary adenocarcinoma | T4N2M0 | 1 | II | malignant |
| F4 | 45 | M | Colon | Mucinous adenocarcinoma | T2N0M0 | 2 | I | malignant |
| F5 | 69 | F | Colon | Adenocarcinoma | T3N1M0 | 2 | II | malignant |
| F6 | 82 | M | Colon | Adenocarcinoma (sparse) | T4N0M0 | 2 | II | malignant |
| F7 | 74 | M | Colon | Adenocarcinoma | T4N0M0 | 2 | II | malignant |
| F8 | 52 | F | Colon | Adenocarcinoma | T3N1M0 | 2 | II | malignant |
| F9 | 41 | M | Colon | Adenocarcinoma | T4N0M0 | 2 | II | malignant |
| F10 | 54 | F | Colon | Adenocarcinoma | T4N1M0 | 2 | III | malignant |
| F11 | 79 | F | Colon | Adenocarcinoma | T4N0M0 | 2 | II | malignant |
| F12 | 53 | M | Colon | Adenocarcinoma | T4N0M0 | 2 | II | malignant |
| F13 | 54 | F | Colon | Adenocarcinoma | T4N0M0 | 2 | II | malignant |
| F14 | 46 | M | Colon | Adenocarcinoma | T4N0M0 | 2 | II | malignant |

TABLE 9-continued

| Position | Age | Sex | Organ (Anatomic Site) | Pathology diagnosis | TNM | Grade | Stage | Type |
|---|---|---|---|---|---|---|---|---|
| F15 | 58 | F | Colon | Adenocarcinoma | T4N0M0 | 2 | II | malignant |
| F16 | 46 | M | Colon | Mucinous adenocarcinoma | T3N2M0 | 2 | III | malignant |
| G1 | 66 | M | Colon | Mucinous adenocarcinoma | T4N0M0 | 2 | II | malignant |
| G2 | 56 | M | Colon | Adenocarcinoma (sparse) | T2N0M0 | 2 | II | malignant |
| G3 | 70 | F | Colon | Mucinous adenocarcinoma | T3N1M0 | 1 | II | malignant |
| G4 | 45 | M | Colon | Adenocarcinoma (sparse) | T4N1M0 | 2 | II | malignant |
| G5 | 55 | F | Colon | Adenocarcinoma | T3N1M0 | 1 | II | malignant |
| G6 | 58 | F | Colon | Adenocarcinoma | T4N2M0 | 3 | III | malignant |
| G7 | 64 | M | Colon | Adenocarcinoma | T3N1M0 | 1 | II | malignant |
| G8 | 66 | F | Colon | Adenocarcinoma with necrosis | T4N0M0 | 2 | II | malignant |
| G9 | 47 | F | Colon | Adenocarcinoma with necrosis | T3N1M0 | 2 | II | malignant |
| G10 | 78 | F | Colon | Adenocarcinoma | T3N1M0 | 2 | II | malignant |
| G11 | 71 | M | Colon | Adenocarcinoma | T4N0M0 | 2 | II | malignant |
| G12 | 34 | F | Colon | Adenocarcinoma | T4N0M0 | 2 | II | malignant |
| G13 | 73 | F | Colon | Adenocarcinoma | T4N1M0 | 3 | II | malignant |
| G14 | 74 | F | Colon | Adenocarcinoma (smooth muscle and blood vessel tissue) | T3N0M0 | — | II | malignant |
| G15 | 61 | M | Colon | Mucinous adenocarcinoma | T3N1M0 | 2 | II | malignant |
| G16 | 38 | M | Colon | Adenocarcinoma | T4N0M0 | 3 | II | malignant |
| H1 | 46 | M | Colon | Adenocarcinoma | T4N0M0 | 3 | II | malignant |
| H2 | 70 | M | Colon | Adenocarcinoma (fibrous tissue and blood vessel tissue) | T4N0M0 | — | II | malignant |
| H3 | 37 | M | Colon | Adenocarcinoma | T4N0M0 | 3 | II | malignant |
| H4 | 48 | F | Colon | Adenocarcinoma | T4N2M1 | 3 | IV | malignant |
| H5 | 50 | M | Colon | Adenocarcinoma | T4N0M0 | 3 | II | malignant |
| H6 | 30 | M | Colon | Adenocarcinoma | T4N0M0 | 3 | II | malignant |
| H7 | 70 | F | Colon | Mucinous adenocarcinoma | T3N1M0 | 3 | II | malignant |
| H8 | 48 | M | Colon | Adenocarcinoma | T4N2M1 | 3 | IV | malignant |
| H9 | 76 | M | Prostate | Adenocarcinoma | T2aN0M0 | 1 | II | malignant |
| H10 | 70 | M | Prostate | Adenocarcinoma | T2aN0M0 | 1 | II | malignant |
| H11 | 60 | M | Prostate | Adenocarcinoma | T4N1M1c | 1 | IV | malignant |
| H12 | 70 | M | Prostate | Adenocarcinoma | T2N0M0 | 1 | II | malignant |
| H13 | 66 | M | Prostate | Adenocarcinoma | T3N1M1 | 1-2 | IV | malignant |
| H14 | 62 | M | Prostate | Adenocarcinoma | T2N0M0 | 2 | II | malignant |
| H15 | 82 | M | Prostate | Adenocarcinoma | T2N0M0 | 2 | II | malignant |
| H16 | 78 | M | Prostate | Adenocarcinoma | T4N1M1b | 2 | IV | malignant |
| I1 | 80 | M | Prostate | Adenocarcinoma | T4N1M1c | 2 | IV | malignant |
| I2 | 67 | M | Prostate | Adenocarcinoma | T2N0M1 | 3 | IV | malignant |
| I3 | 69 | M | Prostate | Adenocarcinoma | T3N0M0 | 1 | III | malignant |
| I4 | 73 | M | Prostate | Adenocarcinoma | T2N0M0 | 1 | II | malignant |
| I5 | 64 | M | Prostate | Adenocarcinoma | T3N0M1b | 2 | IV | malignant |
| I6 | 69 | M | Prostate | Adenocarcinoma | T2N0M0 | 3 | II | malignant |
| I7 | 64 | M | Prostate | Adenocarcinoma | T2aN0M0 | 2 | II | malignant |
| I8 | 73 | M | Prostate | Adenocarcinoma | T2N0M0 | 2 | II | malignant |
| I9 | 75 | M | Prostate | Adenocarcinoma | T4N1M1b | 3 | IV | malignant |
| I10 | 85 | M | Prostate | Adenocarcinoma | T3N1M1 | 1 | IV | malignant |
| I11 | 69 | M | Prostate | Adenocarcinoma (smooth muscle and blood vessel tissue) | T4N0M0 | — | III | malignant |
| I12 | 71 | M | Prostate | Adenocarcinoma (sparse) | T2N0M0 | 3 | II | malignant |
| I13 | 70 | M | Prostate | Adenocarcinoma | T2N0M0 | 2 | II | malignant |
| I14 | 64 | M | Prostate | Adenocarcinoma | T2N0M0 | 3 | II | malignant |
| I15 | 51 | M | Prostate | Adenocarcinoma (hyperplasia) | T2N0M0 | — | II | malignant |
| I16 | 70 | M | Prostate | Adenocarcinoma | T2bN0M0 | 3 | II | malignant |
| J1 | 62 | M | Prostate | Adenocarcinoma | T3N1M1b | 2 | IV | malignant |
| J2 | 58 | M | Prostate | Adenocarcinoma | T2N0M0 | 2 | II | malignant |
| J3 | 57 | M | Prostate | Adenocarcinoma (sparse) | T2aN0M0 | 3 | II | malignant |
| J4 | 69 | M | Prostate | Adenocarcinoma | T2N0M0 | 1 | II | malignant |
| J5 | 72 | M | Prostate | Adenocarcinoma | T3N0M0 | 3 | III | malignant |
| J6 | 70 | M | Prostate | Adenocarcinoma | T3N0M0 | 3 | II | malignant |

TABLE 9-continued

| Position | Age | Sex | Organ (Anatomic Site) | Pathology diagnosis | TNM | Grade | Stage | Type |
|---|---|---|---|---|---|---|---|---|
| J7 | 82 | M | Prostate | Adenocarcinoma (smooth muscle and blood vessel tissue) | T2N0M0 | — | II | malignant |
| J8 | 55 | M | Prostate | Adenocarcinoma (hyperplasia) | T2N0M0 | — | II | malignant |
| J9 | 66 | M | Prostate | Adenocarcinoma | T2N0M0 | 3 | II | malignant |
| J10 | 73 | M | Prostate | Adenocarcinoma | T4N1M1c | 3 | IV | malignant |
| J11 | 75 | M | Prostate | Adenocarcinoma | T2N1M1c | 3 | IV | malignant |
| J12 | 63 | M | Prostate | Adenocarcinoma | T2N1M1b | 3 | IV | malignant |
| J13 | 60 | M | Prostate | Adenocarcinoma | T3N1M1b | 3 | IV | malignant |
| J14 | 75 | M | Prostate | Adenocarcinoma | T3N0M0 | 3 | III | malignant |
| J15 | 87 | M | Prostate | Adenocarcinoma | T2N0M0 | 3 | II | malignant |
| J16 | 55 | M | Prostate | Adenocarcinoma (sparse) | T2N0M0 | 3 | II | malignant |
| K1 | 65 | M | Pancreas | Adenocarcinoma (fibrous tissue and inflammatory cell infiltration) | T2N0M0 | — | I | malignant |
| K2 | 68 | F | Pancreas | Adenocarcinoma (fibrous tissue and a little pancreatic islet tissue) | T2N0M0 | — | I | malignant |
| K3 | 53 | F | Pancreas | Duct adenocarcinoma (sparse) | T2N0M0 | — | I | malignant |
| K4 | 54 | F | Pancreas | Duct adenocarcinoma | T3N0M0 | 1 | II | malignant |
| K5 | 42 | F | Pancreas | Duct adenocarcinoma | T3N0M0 | 2 | II | malignant |
| K6 | 57 | M | Pancreas | Duct adenocarcinoma | T3N0M0 | 3 | II | malignant |
| K7 | 62 | F | Pancreas | Mucinous adenocarcinoma | T4N0M0 | 1 | IV | malignant |
| K8 | 50 | M | Pancreas | Duct adenocarcinoma | T2N1M0 | 2 | III | malignant |
| K9 | 60 | M | Pancreas | Duct adenocarcinoma | T3N0M0 | 2 | II | malignant |
| K10 | 53 | F | Pancreas | Duct adenocarcinoma | T3N0M0 | 3 | II | malignant |
| K11 | 75 | F | Pancreas | Duct adenocarcinoma | T3N0M1 | 1 | IV | malignant |
| K12 | 47 | M | Pancreas | Duct adenocarcinoma | T3N0M0 | 2 | II | malignant |
| K13 | 60 | M | Pancreas | Mucinous adenocarcinoma | T2N0M0 | 3 | I | malignant |
| K14 | 64 | M | Pancreas | Adenocarcinoma (lymphatic tissue) | T3N0M0 | — | II | malignant |
| K15 | 38 | M | Pancreas | Duct adenocarcinoma | T3N0M1 | 3 | IV | malignant |
| K16 | 49 | M | Pancreas | Mucinous adenocarcinoma | T3N0M0 | 2 | II | malignant |
| L1 | 64 | F | Pancreas | Duct adenocarcinoma | T3N0M0 | 2 | II | malignant |
| L2 | 49 | M | Pancreas | Duct adenocarcinoma | T2N1M0 | 2-3 | III | malignant |
| L3 | 51 | F | Pancreas | Duct adenocarcinoma | T3N0M0 | 2 | II | malignant |
| L4 | 54 | F | Pancreas | Duct adenocarcinoma | T2N0M0 | 2 | I | malignant |
| L5 | 76 | F | Pancreas | Duct adenocarcinoma | T4N0M0 | 2 | IV | malignant |
| L6 | 60 | M | Pancreas | Duct adenocarcinoma | T3N0M0 | 2 | II | malignant |
| L7 | 55 | M | Pancreas | Duct adenocarcinoma | T3N0M0 | 2 | II | malignant |
| L8 | 51 | F | Pancreas | Duct adenocarcinoma | T3N0M0 | 3 | II | malignant |
| L9 | 67 | M | Pancreas | Duct adenocarcinoma with necrosis | T3N0M0 | 3 | II | malignant |
| L10 | 44 | M | Pancreas | Duct adenocarcinoma | T3N0M0 | 3 | II | malignant |
| L11 | 68 | F | Pancreas | Duct adenocarcinoma | T3N0M0 | 3 | II | malignant |

TABLE 9-continued

| Position | Age | Sex | Organ (Anatomic Site) | Pathology diagnosis | TNM | Grade | Stage | Type |
|---|---|---|---|---|---|---|---|---|
| L12 | 62 | M | Pancreas | Duct adenocarcinoma | T3N0M0 | 3 | II | malignant |
| L13 | 57 | F | Pancreas | Duct adenocarcinoma | T2N0M0 | 3 | I | malignant |
| L14 | 53 | F | Pancreas | Duct adenocarcinoma with necrosis (sparse) | T2N0M0 | 3 | I | malignant |
| L15 | 41 | M | Pancreas | Duct adenocarcinoma | T4N1M0 | 3 | III | malignant |
| L16 | 47 | F | Pancreas | Duct adenocarcinoma (chronic inflammation of pancreas tissue) | T3N1M0 | — | III | malignant |
| M1 | 58 | F | Pancreas | Duct adenocarcinoma | T3N0M0 | 2 | II | malignant |
| M2 | 78 | M | Pancreas | Duct adenocarcinoma | T3N0M0 | 3 | II | malignant |
| M3 | 61 | M | Pancreas | Duct adenocarcinoma | T3N0M1 | 3 | IV | malignant |
| M4 | 56 | M | Pancreas | Duct adenocarcinoma with necrosis | T2N0M0 | 3 | I | malignant |
| M5 | 45 | M | Pancreas | Duct adenocarcinoma | T2N1M0 | 3 | III | malignant |
| M6 | 50 | M | Pancreas | Duct adenocarcinoma with necrosis | T2N0M0 | 3 | I | malignant |
| M7 | 52 | M | Pancreas | Duct adenocarcinoma (sparse) | T2N0M0 | 3 | I | malignant |
| M8 | 55 | M | Pancreas | Duct adenocarcinoma | T3N0M0 | 3 | II | malignant |

The sections were fixed in cold 10% buffered neutral formalin for 15 min. Immunohistochemistry (IHC) was performed by incubation of slides for 24 hours at 4 C or 2 hours at room temperature with undiluted hybridoma supernatant or purified Mabs (1AG and 4AG). Bound mAbs were detected with FITC-conjugated rabbit anti-mouse immunoglobulin (1:100; Dako, Denmark) or peroxidase conjugated rabbit anti-mouse immunoglobulin. Slides were mounted with Prolong Gold antifade reagent with DAPI (Invitrogen), and micrographs were obtained on a Leica wide-field fluorescence microscope.

7.8.2. Results

Results for 1AG are shown in FIG. 8. Results for 4AG are shown in FIG. 9. mAb 1AG reacted specifically with a proportion of tumors from most of the examined cancer tissues, including tissue from breast, lung, colon, and pancreas carcinomas. mAb 4AG reacted strongly and specifically with a significant proportion of tumors from the majority of the examined cancer, including tissue from breast, lung, colon, prostate, and pancreas carcinomas.

7.9 Example 9: Epitope Mapping of 1AG and 4AG Antibodies by Alanine Scanning 7.9.1. Materials and Methods
7.9.1.1 Materials
The following reagents were used in the studies described in this example.

| Reagent | Source, Catalog Number |
|---|---|
| 0.2M bicarbonate buffer pH 9.8 | Thermo Scientific, 28382 |
| ELISA plates | Corning, 9018 |
| 2.5% BSA in 1x PBS pH 7.4 | PBS: Gibco, 10010049 |
|  | BSA: USBiological, A1311 |
| Biotinylated Villa Villosa lectin | Vector Labs, B-1235 |
| 1X TBS/0.05% Tween-20 (TBST) | VWR, K873-1 |
| Goat-anti mouse IgG (H + L)-HRP | Jackson ImmunoResearch, 115-035-062 |
| Streptavidin-HRP | Thermo Scientific, N504 |
| 1-Step TMB substrate | Thermo Scientific, 34028 |
| 2N Sulfuric Acid | VWR, cat no. BDH7500-1L |

7.9.1.2 Walking Alanine Library Synthesis

A walking alanine library containing 12 linear glycopeptides based on a 28-mer section of the MUC1 protein (TAPPAHGVTSAPDTRPAPGSTAPPAHGV (SEQ ID NO:105), where bold, underlined residues are glycosylated with GalNAc) was constructed. The 12 glycopeptides each contain a unique alanine point mutation within positions 13-24 of the 28-mer MUC1 protein. If the native amino acid within position 13-24 was an alanine, this residue was mutated into a glycine residue. Amino acid sequences for the glycopeptides of the library are shown in Table 10A. Glycopeptides were synthesized using Fmoc chemistry. Fmoc-GalNAc-Serine (GalNac-Ser) and Fmoc-GalNAc-Threonine (GalNAc-Thr) building blocks were purchased from Sussex Research (Ottawa, Canada). A non-glycosylated version of the 28-mer MUC1 peptide was synthesized alongside the glycopeptides to serve as a negative control. Peptides were lyophilized after synthesis and resuspended in deionized water to a concentration of 1 mg/ml prior to use.

7.9.1.3 Epitope Mapping of 5E5, 1AG, & 4AG

The library was used in an ELISA format to map the epitopes of the following MUC1-Tn antibodies: 5E5, 1AG and 4AG. The non-glycosylated MUC1 peptide served as a negative control and the peptide RPAPGSTAPPAHGVT (SEQ ID NO:99), glycosylated with GalNAc on the serine and threonine residues shown in bold underlined text, was used as a positive control. An irrelevant glycopeptide was used to measure GalNAc cross reactivity. Control peptide sequences are shown in Table 10B.

TABLE 10A

MUC1 Alanine Library

| Peptide | Amino acid position |
| --- | --- |
| | 1 2 3 4 5 6 7 8 9 10 11 12 13 14 15 16 17 18 19 20 21 22 23 24 25 26 27 28 |
| 1 (SEQ ID NO: 106) | T A P P A H G V _T_ _S_ A P A _T_ R P A P G _S_ _T_ A P P A H G V |
| 2 (SEQ ID NO: 107) | T A P P A H G V _T_ _S_ A P D A R P A P G _S_ _T_ A P P A H G V |
| 3 (SEQ ID NO: 108) | T A P P A H G V _T_ _S_ A P D _T_ A P A P G _S_ _T_ A P P A H G V |
| 4 (SEQ ID NO: 109) | T A P P A H G V _T_ _S_ A P D _T_ R A A P G _S_ _T_ A P P A H G V |
| 5 (SEQ ID NO: 110) | T A P P A H G V _T_ _S_ A P D _T_ R P A P G _S_ _T_ A P P A H G V |
| 6 (SEQ ID NO: 111) | T A P P A H G V _T_ _S_ A P D _T_ R P A A G _S_ _T_ A P P A H G V |
| 7 (SEQ ID NO: 112) | T A P P A H G V _T_ _S_ A P D _T_ R P A P A _S_ _T_ A P P A H G V |
| 8 (SEQ ID NO: 113) | T A P P A H G V _T_ _S_ A P D _T_ R P A P G A _T_ A P P A H G V |
| 9 (SEQ ID NO: 114) | T A P P A H G V _T_ _S_ A P D _T_ R P A P G _S_ A A P P A H G V |
| 10 (SEQ ID NO: 115) | T A P P A H G V _T_ _S_ A P D _T_ R P A P G _S_ _T_ A P P A H G V |
| 11 (SEQ ID NO: 116) | T A P P A H G V _T_ _S_ A P D _T_ R P A P G _S_ _T_ A A P A H G V |
| 12 (SEQ ID NO: 117) | T A P P A H G V _T_ _S_ A P D _T_ R P A P G _S_ _T_ A P A A H G V |

Bold, italic text indicates alanine substitution stie (or glycine in case of naturally occuring alanine)
Bold, underline text indicates GalNAc-Serine or GalNAc-Threonine

TABLE 10B

Control Peptides

| Peptide | Peptide Sequence |
|---|---|
| Negative Control | TAPPAHGVTSAPDTRPAPGSTAPPAHGV (SEQ ID NO: 105) |
| Positive Control or "Wild type" | RPAPGSTAPPAHGVT (SEQ ID NO: 99) |
| Irrelevant Glycopeptide | PPERGAPPSTFKGTPTAENP (SEQ ID NO: 118) |

Bold, underline text indicates GalNAc-Serine or GalNAc-Threonine

Glycopeptides and relevant controls were diluted to 0.25 µg/ml in 0.2 M bicarbonate buffer pH 9.8 and 100 µl was plated onto each well of a high binding ELISA plate. Plates were then incubated overnight at 4° C. After discarding the coating buffer, the plate was blocked with 300 µl per well of blocking buffer (2.5% BSA in 1×PBS) for 1 hr at room temperature. Blocking buffer was then discarded, and 100 µl per well of antibody supernatant for each of 5E5, 1AG, and 4AG (diluted in blocking buffer) was added and incubated for 1 hr at room temperature. Antibody supernatant dilutions were previously optimized for each antibody (data not shown). Biotinylated Villa Villosa lectin (100 µl per well of 1 µg/ml in blocking buffer) was added to the plate as a control to detect the presence of GalNAc modified residues on the peptide. Plates were washed 3 times with 300 µl per well 1×TBS/0.05% Tween-20 (TBST). The secondary antibody Goat-anti mouse IgG (H+L)-HRP was diluted 1/5000 in blocking buffer and 100 µl of the diluted antibody was added per well and incubated on the plate for 1 hr at room temperature. Streptavidin-HRP was diluted 1/3000 in blocking buffer and 100 µl of the diluted streptavidin-HRP was added to wells containing the biotinylated lectin. Following secondary incubation, the plate was washed 4 times with 300 µl of TBST per well and then developed with 75 µl of room temperature 1-Step TMB substrate. After 1 minute, color development was stopped using 75 µl 2 N sulfuric acid. The plate was then read at 450 nm using a plate reader (Molecular Device SpectraMax i3).

7.9.1.4 Data Analysis

Data was analyzed in Microsoft Excel software. The data was interpreted by converting the reactivity of each antibody to the "mutant" peptide as percent binding compared to the wild type peptide. Percent binding was calculated using the formula (OD_MutantPeptide/OD_WildType peptide). Percent binding was then displayed in a bar chart where all values were between 0-1.

7.9.2. Results

The percent binding of 5E5, 1AG, and 4AG to the peptides is shown in FIGS. 10-12, respectively. Alanine substitutions within the region of residues 17-23 greatly reduced binding of 1AG and 4AG. Compared to 5E5, 1AG and 4AG binding was reduced by more alanine substitutions. For each of peptides 5-11, 4AG binding decreased greatly compared to the "wild type" peptide. This suggests the binding epitope of 4AG is within the region of residues 17-23. 1AG binding was even more restrictive, with greatly decreased binding compared to wild type for each of peptides 3-12, which corresponds to the region of residues 15-24. In the region of residues 19-22, 1AG and 4AG binding was almost completely inhibited by a Ser-GalNAc substitution on peptide 8 (2.23% and 1.63%, respectfully), whereas 5E5 could still bind (18%). In contrast, a Thr-GalNAc substitution on peptide 9 almost completely inhibited 5E5 binding (2.93%), while 4AG and 1AG could still bind at 14.62% and 6.07%, respectively. This suggests that the glycosylated serine plays a greater role in 1AG and 4AG binding than GalNAc-Thr, which was opposite for 5E5. Overall, the results of the alanine scan show that the epitopes of 1AG and 4AG appear to different from 5E5. The differences include making a greater number of contacts with glyco-MUC1 which (without being bound by theory) is believed to confer a greater degree of selectivity for the cancer antigen.

8. SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

1. An anti-glyco-MUC1 antibody or antigen binding fragment that competes with an antibody or antigen binding fragment comprising (i) a heavy chain variable (VH) sequence of SEQ ID NO:1 and a light chain variable (VL) sequence of SEQ ID NO:2 or (ii) a heavy chain variable (VH) sequence of SEQ ID NO:23 and a light chain variable (VL) sequence of SEQ ID NO:24 for binding to the MUC1 peptide RPAPGSTAPPAHGVT (SEQ ID NO:99) that has been glycosylated with GalNAc on the serine and threonine residues shown with bold and underlined text.

2. An anti-glyco-MUC1 antibody or antigen binding fragment that competes with an antibody or antigen binding fragment comprising (i) a heavy chain variable (VH) sequence of SEQ ID NO:1 and a light chain variable (VL) sequence of SEQ ID NO:2 or (ii) a heavy chain variable (VH) sequence of SEQ ID NO:23 and a light chain variable (VL) sequence of SEQ ID NO:24 for binding to the breast cancer cell line MCF7 or T47D.

3. An anti-glyco-MUC1 antibody or antigen binding fragment comprising a complementarity determining region (CDR) H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:97, and a CDR-L3 comprising the amino acid sequence of SEQ ID NO:98.

4. The anti-glyco-MUC1 antibody or antigen-binding fragment of embodiment 1 or embodiment 2, comprising a complementarity determining region (CDR) H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:97, and a CDR-L3 comprising the amino acid sequence of SEQ ID NO:98.

5. The anti-glyco-MUC1 antibody or antigen-binding fragment of embodiment 3 or embodiment 4, wherein CDR-H1 comprises the amino acid sequence of SEQ ID NO:3.

6. The anti-glyco-MUC1 antibody or antigen-binding fragment of embodiment 3 or embodiment 4, wherein CDR-H1 comprises the amino acid sequence of SEQ ID NO:9.

7. The anti-glyco-MUC1 antibody or antigen-binding fragment of embodiment 3 or embodiment 4, wherein CDR-H1 comprises the amino acid sequence of SEQ ID NO:15.

8. The anti-glyco-MUC1 antibody or antigen-binding fragment of embodiment 3 or embodiment 4, wherein CDR-H1 comprises the amino acid sequence of SEQ ID NO:25.

9. The anti-glyco-MUC1 antibody or antigen-binding fragment of embodiment 3 or embodiment 4, wherein CDR-H1 comprises the amino acid sequence of SEQ ID NO:31.

10. The anti-glyco-MUC1 antibody or antigen-binding fragment of embodiment 3 or embodiment 4, wherein CDR-H1 comprises the amino acid sequence of SEQ ID NO:37.

11. The anti-glyco-MUC1 antibody or antigen-binding fragment of embodiment 3 or embodiment 4, wherein CDR-H1 comprises the amino acid sequence of SEQ ID NO:45.

12. The anti-glyco-MUC1 antibody or antigen-binding fragment of embodiment 3 or embodiment 4, wherein CDR-H1 comprises the amino acid sequence of SEQ ID NO:51.

13. The anti-glyco-MUC1 antibody or antigen-binding fragment of embodiment 3 or embodiment 4, wherein CDR-H1 comprises the amino acid sequence of SEQ ID NO:57.

14. The anti-glyco-MUC1 antibody or antigen-binding fragment of embodiment 3 or embodiment 4, wherein CDR-H1 comprises the amino acid sequence of SEQ ID NO:63.

15. The anti-glyco-MUC1 antibody or antigen-binding fragment of embodiment 3 or embodiment 4, wherein CDR-H1 comprises the amino acid sequence of SEQ ID NO:69.

16. The anti-glyco-MUC1 antibody or antigen-binding fragment of embodiment 3 or embodiment 4, wherein CDR-H1 comprises the amino acid sequence of SEQ ID NO:75.

17. The anti-glyco-MUC1 antibody or antigen-binding fragment of embodiment 3 or embodiment 4, wherein CDR-H1 comprises the amino acid sequence of SEQ ID NO:81.

18. The anti-glyco-MUC1 antibody or antigen-binding fragment of embodiment 3 or embodiment 4, wherein CDR-H1 comprises the amino acid sequence of SEQ ID NO:87.

19. The anti-glyco-MUC1 antibody or antigen-binding fragment of any one of embodiments 3 to 18, wherein CDR-H2 comprises the amino acid sequence of SEQ ID NO:4.

20. The anti-glyco-MUC1 antibody or antigen-binding fragment of any one of embodiments 3 to 18, wherein CDR-H2 comprises the amino acid sequence of SEQ ID NO:10.

21. The anti-glyco-MUC1 antibody or antigen-binding fragment of any one of embodiments 3 to 18, wherein CDR-H2 comprises the amino acid sequence of SEQ ID NO:16.

22. The anti-glyco-MUC1 antibody or antigen-binding fragment of any one of embodiments 3 to 18, wherein CDR-H2 comprises the amino acid sequence of SEQ ID NO: 26.

23. The anti-glyco-MUC1 antibody or antigen-binding fragment of any one of embodiments 3 to 18, wherein CDR-H2 comprises the amino acid sequence of SEQ ID NO:32.

24. The anti-glyco-MUC1 antibody or antigen-binding fragment of any one of embodiments 3 to 18, wherein CDR-H2 comprises the amino acid sequence of SEQ ID NO:38.

25. The anti-glyco-MUC1 antibody or antigen-binding fragment of any one of embodiments 3 to 18, wherein CDR-H2 comprises the amino acid sequence of SEQ ID NO:46.

26. The anti-glyco-MUC1 antibody or antigen-binding fragment of any one of embodiments 3 to 18, wherein CDR-H2 comprises the amino acid sequence of SEQ ID NO:52.

27. The anti-glyco-MUC1 antibody or antigen-binding fragment of any one of embodiments 3 to 26, wherein CDR-H3 comprises the amino acid sequence of SEQ ID NO:5.

28. The anti-glyco-MUC1 antibody or antigen-binding fragment of any one of embodiments 3 to 26, wherein CDR-H3 comprises the amino acid sequence of SEQ ID NO:11.

29. The anti-glyco-MUC1 antibody or antigen-binding fragment of any one of embodiments 3 to 26, wherein CDR-H3 comprises the amino acid sequence of SEQ ID NO:27.

30. The anti-glyco-MUC1 antibody or antigen-binding fragment of any one of embodiments 3 to 26, wherein CDR-H3 comprises the amino acid sequence of SEQ ID NO:33.

31. The anti-glyco-MUC1 antibody or antigen-binding fragment of any one of embodiments 3 to 26, wherein CDR-H3 comprises the amino acid sequence of SEQ ID NO:47.

32. The anti-glyco-MUC1 antibody or antigen-binding fragment of any one of embodiments 3 to 31, wherein CDR-L1 comprises the amino acid sequence of SEQ ID NO:6.

33. The anti-glyco-MUC1 antibody or antigen-binding fragment of any one of embodiments 3 to 31, wherein CDR-L1 comprises the amino acid sequence of SEQ ID NO:12.

34. The anti-glyco-MUC1 antibody or antigen-binding fragment of any one of embodiments 3 to 31, wherein CDR-L1 comprises the amino acid sequence of SEQ ID NO:18.

35. The anti-glyco-MUC1 antibody or antigen-binding fragment of any one of embodiments 3 to 31, wherein CDR-L1 comprises the amino acid sequence of SEQ ID NO:28.

36. The anti-glyco-MUC1 antibody or antigen-binding fragment of any one of embodiments 3 to 31, wherein CDR-L1 comprises the amino acid sequence of SEQ ID NO:34.

37. The anti-glyco-MUC1 antibody or antigen-binding fragment of any one of embodiments 3 to 31, wherein CDR-L1 comprises the amino acid sequence of SEQ ID NO:40.

38. The anti-glyco-MUC1 antibody or antigen-binding fragment of any one of embodiments 3 to 31, wherein CDR-L1 comprises the amino acid sequence of SEQ ID NO:54.

39. The anti-glyco-MUC1 antibody or antigen-binding fragment of any one of embodiments 3 to 31, wherein CDR-L1 comprises the amino acid sequence of SEQ ID NO:60.

40. The anti-glyco-MUC1 antibody or antigen-binding fragment of any one of embodiments 3 to 39, wherein CDR-L2 comprises the amino acid sequence of SEQ ID NO:13.

41. The anti-glyco-MUC1 antibody or antigen-binding fragment of any one of embodiments 3 to 40, wherein CDR-L3 comprises the amino acid sequence of SEQ ID NO:8.

42. The anti-glyco-MUC1 antibody or antigen-binding fragment of any one of embodiments 1 to 4, which has a VH comprising complementarity determining regions (CDRs) of SEQ ID NOS:3-5 and a VL comprising CDRs of SEQ ID NOS:6-8.

43. The anti-glyco-MUC1 antibody or antigen-binding fragment of any one of embodiments 1 to 4, which has a VH comprising complementarity determining regions (CDRs) of SEQ ID NOS:9-11 and a VL comprising CDRs of SEQ ID NOS:12-14.

44. The anti-glyco-MUC1 antibody or antigen-binding fragment of any one of embodiments 1 to 4, which has a VH comprising complementarity determining regions (CDRs) of SEQ ID NOS:15-17 and a VL comprising CDRs of SEQ ID NOS:18-20.

45. The anti-glyco-MUC1 antibody or antigen-binding fragment of any one of embodiments 1 to 4, which has a VH comprising complementarity determining regions (CDRs) of SEQ ID NOS:25-27 and a VL comprising CDRs of SEQ ID NOS:28-30.

46. The anti-glyco-MUC1 antibody or antigen-binding fragment any one of embodiments 1 to 4, which has a VH comprising complementarity determining regions (CDRs) of SEQ ID NOS:31-33 and a VL comprising CDRs of SEQ ID NOS:34-36.

47. The anti-glyco-MUC1 antibody or antigen-binding fragment of any one of embodiments 1 to 4, which has a VH comprising complementarity determining regions (CDRs) of SEQ ID NOS:37-39 and a VL comprising CDRs of SEQ ID NOS:40-42.

48. The anti-glyco-MUC1 antibody or antigen-binding fragment of any one of embodiments 1 to 4, which has a VH comprising complementarity determining regions (CDRs) of SEQ ID NOS:45-47 and a VL comprising CDRs of SEQ ID NOS:48-50.

49. The anti-glyco-MUC1 antibody or antigen-binding fragment of any one of embodiments 1 to 4, which has a VH comprising complementarity determining regions (CDRs) of SEQ ID NOS:51-53 and a VL comprising CDRs of SEQ ID NOS:54-56.

50. The anti-glyco-MUC1 antibody or antigen-binding fragment of any one of embodiments 1 to 4, which has a VH comprising complementarity determining regions (CDRs) of SEQ ID NOS:57-59 and a VL comprising CDRs of SEQ ID NOS:60-62.

51. The anti-glyco-MUC1 antibody or antigen-binding fragment of any one of embodiments 1 to 4, which has a VH comprising complementarity determining regions (CDRs) of SEQ ID NOS:63-65 and a VL comprising CDRs of SEQ ID NOS:66-68.

52. The anti-glyco-MUC1 antibody or antigen-binding fragment of any one of embodiments 1 to 4, which has a VH comprising complementarity determining regions (CDRs) of SEQ ID NOS:69-71 and a VL comprising CDRs of SEQ ID NOS:72-74.

53. The anti-glyco-MUC1 antibody or antigen-binding fragment of any one of embodiments 1 to 4, which has a VH comprising complementarity determining regions (CDRs) of SEQ ID NOS:75-77 and a VL comprising CDRs of SEQ ID NOS:78-80.

54. The anti-glyco-MUC1 antibody or antigen-binding fragment of any one of embodiments 1 to 4, which has a VH comprising complementarity determining regions (CDRs) of SEQ ID NOS:81-83 and a VL comprising CDRs of SEQ ID NOS:84-86.

55. The anti-glyco-MUC1 antibody or antigen-binding fragment of any one of embodiments 1 to 4, which has a VH comprising complementarity determining regions (CDRs) of SEQ ID NOS:87-89 and the VL comprises CDRs of SEQ ID NOS:90-92.

56. The anti-glyco-MUC1 antibody or antigen-binding fragment of any one of embodiments 1 to 55 which is a chimeric or humanized antibody.

57. The anti-glyco-MUC1 antibody or antigen-binding fragment of any one of embodiments 1 to 56, which has a VH comprising an amino acid sequence having at least 95% sequence identity to SEQ ID NO:1 and a VL comprising an amino acid sequence having at least 95% sequence identity to SEQ ID NO:2.

58. The anti-glyco-MUC1 antibody or antigen-binding fragment of any one of embodiments 1 to 56, which has a VH comprising an amino acid sequence having at least 97% sequence identity to SEQ ID NO:1 and a VL comprising an amino acid sequence having at least 97% sequence identity to SEQ ID NO:2.

59. The anti-glyco-MUC1 antibody or antigen-binding fragment of any one of embodiments 1 to 56, which has a VH comprising an amino acid sequence having at least 99% sequence identity to SEQ ID NO:1 and a VL comprising an amino acid sequence having at least 99% sequence identity to SEQ ID NO:2.

60. The anti-glyco-MUC1 antibody or antigen-binding fragment of any one of embodiments 1 to 4, which has a VH comprising the amino acid sequence of SEQ ID NO:1 and a VL comprising the amino acid sequence of SEQ ID NO:2.

61. The anti-glyco-MUC1 antibody or antigen-binding fragment of any one of embodiments 1 to 56, which has a VH comprising an amino acid sequence having at least 95% sequence identity to SEQ ID NO:23 and a VL comprising an amino acid sequence having at least 95% sequence identity to SEQ ID NO:24.

62. The anti-glyco-MUC1 antibody or antigen-binding fragment of any one of embodiments 1 to 56, which has a VH comprising an amino acid sequence having at least 97% sequence identity to SEQ ID NO:23 and a VL comprising an amino acid sequence having at least 97% sequence identity to SEQ ID NO:24.

63. The anti-glyco-MUC1 antibody or antigen-binding fragment of any one of embodiments 1 to 56, which has a VH comprising an amino acid sequence having at least 99% sequence identity to SEQ ID NO:23 and a VL comprising an amino acid sequence having at least 99% sequence identity to SEQ ID NO:24.

64. The anti-glyco-MUC1 antibody or antigen-binding fragment of any one of embodiments 1 to 4, which has a VH comprising the amino acid sequence of SEQ ID NO:23 and a VL comprising the amino acid sequence of SEQ ID NO:24.

65. The anti-glyco-MUC1 antibody or antigen-binding fragment of any one of embodiments 1 to 4, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAPGATAPPAHGV (SEQ ID NO:113) as measured by ELISA, wherein serine and threonine residues shown with bold and underlined text indicate residues glycosylated with GalNAc.

66. The anti-glyco-MUC1 antibody or antigen-binding fragment of embodiment 65, wherein the binding of the anti-glyco-MUC1 antibody or antigen-binding fragment to the peptide TAPPAHGVTSAPDTRPAPGATAPPAHGV (SEQ ID NO:113) is less than 5% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

67. The anti-glyco-MUC1 antibody or antigen-binding fragment of embodiment 65, wherein the binding of the anti-glyco-MUC1 antibody or antigen-binding fragment to the peptide TAPPAHGVTSAPDTRPAPGATAPPAHGV (SEQ ID NO:113) is less than 3% of the binding of the anti-glyco-MUC1 antibody or antigen-binding fragment to the peptide RPAPGST**APPAHGVT (SEQ ID NO:99) as measured by ELISA, wherein serine and threonine residues shown with bold and underlined text indicate residues glycosylated with GalNAc.

68. The anti-glyco-MUC1 antibody or antigen-binding fragment of any one of embodiments 65 to 67, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAPGSAAPPAHGV (SEQ ID NO: 114) as measured by ELISA, wherein serine and threonine residues shown with bold and underlined text indicate residues glycosylated with GalNAc.

69. The anti-glyco-MUC1 antibody or antigen-binding fragment of embodiment 68, wherein the binding of the anti-glyco-MUC1 antibody or antigen-binding fragment to the TAPPAHGVTSAPDTRPAPGSAAPPAHGV (SEQ ID NO:114) is less than 20% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

70. The anti-glyco-MUC1 antibody or antigen-binding fragment of embodiment 68, wherein the binding of the anti-glyco-MUC1 antibody or antigen-binding fragment to the TAPPAHGVTSAPDTRPAPGSAAPPAHGV (SEQ ID NO:114) is less than 10% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

71. The anti-glyco-MUC1 antibody or antigen-binding fragment of any one of embodiments 68 to 70, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAPGSTGPPAHGV (SEQ ID NO:115) as measured by ELISA, wherein serine and threonine residues shown with bold and underlined text indicate residues glycosylated with GalNAc.

72. The anti-glyco-MUC1 antibody or antigen-binding fragment of embodiment 71, wherein the binding of the anti-glyco-MUC1 antibody or antigen-binding fragment to the peptide TAPPAHGVTSAPDTRPAPGSTGPPAHGV (SEQ ID NO:115) is less than 20% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

73. The anti-glyco-MUC1 antibody or antigen-binding fragment of embodiment 71, wherein the binding of the anti-glyco-MUC1 antibody or antigen-binding fragment to the peptide TAPPAHGVTSAPDTRPAPGSTGPPAHGV (SEQ ID NO:115) is less than 10% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

74. The anti-glyco-MUC1 antibody or antigen-binding fragment of embodiment 71, wherein the binding of the anti-glyco-MUC1 antibody or antigen-binding fragment to the peptide TAPPAHGVTSAPDTRPAPGSTGPPAHGV (SEQ ID NO: 115) is less than 5% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

75. The anti-glyco-MUC1 antibody or antigen-binding fragment of any one of embodiments 71 to 74, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAPGSTAAPAHGV (SEQ ID NO: 116) as measured by ELISA, wherein serine and threonine residues shown with bold and underlined text indicate residues glycosylated with GalNAc.

76. The anti-glyco-MUC1 antibody or antigen-binding fragment of embodiment 75, wherein the binding of the anti-glyco-MUC1 antibody or antigen-binding fragment to the peptide TAPPAHGVTSAPDTRPAPGSTAAPAHGV (SEQ ID NO:1 16) is less than 10% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

77. The anti-glyco-MUC1 antibody or antigen-binding fragment of embodiment 75, wherein the binding of the anti-glyco-MUC1 antibody or antigen-binding fragment to the peptide TAPPAHGVTSAPDTRPAPGSTAAPAHGV (SEQ ID NO:116) is less than 5% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

78. The anti-glyco-MUC1 antibody or antigen-binding fragment of any one of embodiments 75 to 77, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAPGSTAPAAHGV (SEQ ID NO: 117) as measured by ELISA, wherein serine and threonine residues shown with bold and underlined text indicate residues glycosylated with GalNAc.

79. The anti-glyco-MUC1 antibody or antigen-binding fragment of embodiment 78, wherein the binding of the anti-glyco-MUC1 antibody or antigen-binding fragment to the peptide TAPPAHGVTSAPDTRPAPGSTAPAAHGV (SEQ ID NO:1 17) is less than 80% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

80. The anti-glyco-MUC1 antibody or antigen-binding fragment of embodiment 78, wherein the binding of the anti-glyco-MUC1 antibody or antigen-binding fragment to the peptide TAPPAHGVTSAPDTRPAPGSTAPAAHGV (SEQ ID NO:1 17) is less than 70% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

81. The anti-glyco-MUC1 antibody or antigen-binding fragment of embodiment 78, wherein the binding of the anti-glyco-MUC1 antibody or antigen-binding fragment to the peptide TAPPAHGVTSAPDTRPAPGSTAPAAHGV (SEQ ID NO:1 17) is less than 20% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

82. The anti-glyco-MUC1 antibody or antigen-binding fragment of any one of embodiments 65 to 81, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAPASTAPPAHGV SEQ ID NO: 112) as measured by ELISA, wherein serine and threonine residues shown with bold and underlined text indicate residues glycosylated with GalNAc.

83. The anti-glyco-MUC1 antibody or antigen-binding fragment of embodiment 82, wherein the binding of the anti-glyco-MUC1 antibody or antigen-binding fragment to the peptide TAPPAHGVTSAPDTRPAPASTAPPAHGV SEQ ID NO:112) is less than 5% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

84. The anti-glyco-MUC1 antibody or antigen-binding fragment of embodiment 82, wherein the binding of the anti-glyco-MUC1 antibody or antigen-binding fragment to the peptide TAPPAHGVTSAPDTRPAPASTAPPAHGV SEQ ID NO:112) is less than 3% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

85. The anti-glyco-MUC1 antibody or antigen-binding fragment of any one of embodiments 82 to 84, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPAAGSTAPPAHGV (SEQ ID NO:1 11) as measured by ELISA, wherein serine and threonine residues shown with bold and underlined text indicate residues glycosylated with GalNAc.

86. The anti-glyco-MUC1 antibody or antigen-binding fragment of embodiment 85, wherein the binding of the anti-glyco-MUC1 antibody or antigen-binding fragment to the peptide TAPPAHGVTSAPDTRPAAGSTAPPAHGV (SEQ ID NO:111) is less than 10% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

87. The anti-glyco-MUC1 antibody or antigen-binding fragment of embodiment 85, wherein the binding of the anti-glyco-MUC1 antibody or antigen-binding fragment to the peptide TAPPAHGVTSAPDTRPAAGSTAPPAHGV (SEQ ID NO:111) is less than 5% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

88. The anti-glyco-MUC1 antibody or antigen-binding fragment of any one of embodiments 85 to 87, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRPGPGSTAPPAHGV (SEQ ID NO: 110) as measured by ELISA, wherein serine and threonine residues shown with bold and underlined text indicate residues glycosylated with GalNAc.

89. The anti-glyco-MUC1 antibody or antigen-binding fragment of embodiment 88, wherein the binding of the anti-glyco-MUC1 antibody or antigen-binding fragment to the peptide TAPPAHGVTSAPDTRPGPGSTAPPAHGV (SEQ ID NO: 110) is less than 5% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

90. The anti-glyco-MUC1 antibody or antigen-binding fragment of embodiment 88, wherein the binding of the anti-glyco-MUC1 antibody or antigen-binding fragment to the peptide TAPPAHGVTSAPDTRPGPGSTAPPAHGV (SEQ ID NO: 110) is less than 3% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

91. The anti-glyco-MUC1 antibody or antigen-binding fragment of any one of embodiments 88 to 90, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTRAAPGSTAPPAHGV (SEQ ID NO:109) as measured by ELISA, wherein serine and threonine residues shown with bold and underlined text indicate residues glycosylated with GalNAc.

92. The anti-glyco-MUC1 antibody or antigen-binding fragment of embodiment 91, wherein the binding of the anti-glyco-MUC1 antibody or antigen-binding fragment to the peptide TAPPAHGVTSAPDTRAAPGSTAPPAHGV (SEQ ID NO:109) is less than 80% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

93. The anti-glyco-MUC1 antibody or antigen-binding fragment of embodiment 91, wherein the binding of the anti-glyco-MUC1 antibody or antigen-binding fragment to the peptide TAPPAHGVTSAPDTRAAPGSTAPPAHGV (SEQ ID NO:109) is less than 50% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

94. The anti-glyco-MUC1 antibody or antigen-binding fragment of embodiment 91, wherein the binding of the anti-glyco-MUC1 antibody or antigen-binding fragment to the peptide TAPPAHGVTSAPDTRAAPGSTAPPAHGV (SEQ ID NO:109) is less than 20% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

95. The anti-glyco-MUC1 antibody or antigen-binding fragment of embodiment 91, wherein the binding of the anti-glyco-MUC1 antibody or antigen-binding fragment to the peptide TAPPAHGVTSAPDTRAAPGSTAPPAHGV (SEQ ID NO:109) is less than 10% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

96. The anti-glyco-MUC1 antibody or antigen-binding fragment of any one of embodiments 91 to 95, wherein the anti-glyco-MUC1 antibody or antigen-binding fragment binds to the peptide RPAPGSTAPPAHGVT (SEQ ID NO:99) with greater affinity than to the peptide TAPPAHGVTSAPDTAPAPGSTAPPAHGV (SEQ ID NO:108) as measured by ELISA, wherein serine and threonine residues shown with bold and underlined text indicate residues glycosylated with GalNAc.

97. The anti-glyco-MUC1 antibody or antigen-binding fragment of embodiment 96, wherein the binding of the anti-glyco-MUC1 antibody or antigen-binding fragment to the peptide TAPPAHGVTSAPDTAPAPGSTAPPAHGV (SEQ ID NO:108) is less than 80% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

98. The anti-glyco-MUC1 antibody or antigen-binding fragment of embodiment 96, wherein the binding of the anti-glyco-MUC1 antibody or antigen-binding fragment to the peptide TAPPAHGVTSAPDTAPAPGSTAPPAHGV (SEQ ID NO:108) is less than 50% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

99. The anti-glyco-MUC1 antibody or antigen-binding fragment of embodiment 96, wherein the binding of the anti-glyco-MUC1 antibody or antigen-binding fragment to the peptide TAPPAHGVTSAPDTAPAPGSTAPPAHGV (SEQ ID NO:108) is less than 20% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

100. The anti-glyco-MUC1 antibody or antigen-binding fragment of embodiment 96, wherein the binding of the anti-glyco-MUC1 antibody or antigen-binding fragment to the peptide TAPPAHGVTSAPDTAPAPGSTAPPAHGV (SEQ ID NO:108) is less than 10% of the binding of the anti-glyco-MUC1 antibody or antigen-binding fragment to the peptide RPAPGSTAPPAHGVT (SEQ ID NO:99) as measured by ELISA, wherein serine and threonine residues shown with bold and underlined text indicate residues glycosylated with GalNAc.

101. The anti-glyco-MUC1 antibody or antigen-binding fragment of any one of embodiments 65 to 100, wherein the ELISA comprises an ELISA in which the peptides are used at a concentration of 0.25 µg/ml.

102. The anti-glyco-MUC1 antibody or antigen-binding fragment of any one of embodiments 65 to 101, wherein the ELISA comprises an ELISA performed on a cell culture supernatant from a cell line expressing the anti-glyco-MUC1 antibody or antigen-binding fragment.

103. The anti-glyco-MUC1 antibody or antigen-binding fragment of any one of embodiments 65 to 101, wherein the ELISA comprises an ELISA performed on a diluted cell culture supernatant from a cell line that expressing the anti-glyco-MUC1 antibody or antigen-binding fragment.

104. The anti-glyco-MUC1 antibody or antigen-binding fragment of embodiment 103, wherein the diluted cell culture supernatant comprise a cell culture supernatant which is diluted 2 to 20 times with a buffer.

105. The anti-glyco-MUC1 antibody or antigen-binding fragment of any one of embodiments 65 to 104, wherein the concentration of antibody or antigen-binding fragment in the ELISA ranges between 0.1 mg/mL and 2 mg/mL, optionally wherein the concentration of antibody or antigen-binding fragment in the ELISA ranges between 0.5 mg/mL and 1 mg/mL.

106. The anti-glyco-MUC1 antibody or antigen-binding fragment of any one of embodiments 65 to 105, wherein the concentration of antibody or antigen-binding fragment in the ELISA results in binding to the MUC1 peptide RPAPGSTAPPAHGVT (SEQ ID NO:99).

107. The anti-glyco-MUC1 antibody or antigen-binding fragment of any one of embodiments 65 to 106, wherein the ELISA is performed as described in Example 9.

108. An anti-glyco-MUC1 antibody or antigen-binding fragment that competes with a reference antibody or antigen binding fragment comprising (i) a heavy chain variable (VH) sequence of SEQ ID NO:1 and a light chain variable (VL) sequence of SEQ ID NO:2 or (ii) a heavy chain variable (VH) sequence of SEQ ID NO:23 and a light chain variable (VL) sequence of SEQ ID NO:24 for binding to the MUC1 peptide RPAPGSTAPPAHGVT (SEQ ID NO:99) that has been glycosylated with GalNAc on the serine and threonine residues shown with bold and underlined text, the anti-glyco-MUC1 antibody or antigen-binding fragment comprising:
 (a) a VH sequence with first, second and third CDR means within the VH sequence; and
 (b) a VL sequence with fourth, fifth and sixth CDR means within the VL sequence,
wherein the first, second, third, fourth, fifth, and sixth CDR means cooperate to effect binding of the anti-glyco-MUC1 antibody or antigen-binding fragment to the MUC1 peptide that competes with binding of the reference antibody or antigen binding fragment.

109. The anti-glyco-MUC1 antibody or antigen-binding fragment of embodiment 108, wherein the anti-glyco-MUC1 antibody or antigen-binding fragment competes with a reference antibody or antigen binding fragment comprising a VH sequence of SEQ ID NO:23 and a VL sequence of SEQ ID NO:24.

110. The anti-glyco-MUC1 antibody or antigen-binding fragment of embodiment 108, wherein the anti-glyco-MUC1 antibody or antigen-binding fragment competes with a reference antibody or antigen binding fragment comprising a VH sequence of SEQ ID NO:1 and a VL sequence of SEQ ID NO:2.

111. The anti-glyco-MUC1 antibody or antigen-binding fragment of any one of embodiments 1 to 110, which preferentially binds to a glyco-MUC1 epitope that is over-expressed on cancer cells as compared to normal cells.

112. The anti-glyco-MUC1 antibody or antigen-binding fragment of any of embodiments 1 to 111, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 1 nM to 50 nM as measured by surface plasmon resonance.

113. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 3 nM to 50 nM as measured by surface plasmon resonance.

114. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 3 nM to 40 nM as measured by surface plasmon resonance.

115. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 3 nM to 25 nM as measured by surface plasmon resonance.

116. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 5 nM to 50 nM as measured by surface plasmon resonance.

117. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 5 nM to 25 nM as measured by surface plasmon resonance.

118. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 10 nM to 50 nM as measured by surface plasmon resonance.

119. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 10 nM to 25 nM as measured by surface plasmon resonance.

120. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 15 nM to 50 nM as measured by surface plasmon resonance.

121. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 15 nM to 25 nM as measured by surface plasmon resonance.

122. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 20 nM to 50 nM as measured by surface plasmon resonance.

123. The anti-glyco-MUC1 antibody or antigen-binding fragment of embodiment 112, which binds to the MUC1 peptide RPAPGST**APPAHGVT (SEQ ID NO:99) that has been glycosylated with GalNAc on the serine and threonine residues shown with bold and underlined text with a binding affinity ($K_D$) of 25 nM to 50 nM as measured by surface plasmon resonance.

124. The anti-glyco-MUC1 antibody or antigen-binding fragment of any of embodiments 1 to 123, which is multivalent.

125. The anti-glyco-MUC1 antibody or antigen-binding fragment of any of embodiments 1 to 123, which is in the form of a single-chain variable fragment (scFv).

126. The anti-glyco-MUC1 antibody or antigen-binding fragment of embodiment 125 wherein the scFv comprises the heavy chain variable fragment N-terminal to the light chain variable fragment.

127. The anti-glyco-MUC1 antibody or antigen-binding fragment of embodiment 125 or embodiment 126, wherein the scFv heavy chain variable fragment and light chain variable fragment are covalently bound to a linker sequence of 4-15 amino acids.

128. The anti-glyco-MUC1 antibody or antigen-binding fragment of any of embodiments 1 to 123 which is in the form of a multispecific antibody.

129. The anti-glyco-MUC1 antibody or antigen-binding fragment of embodiment 128 wherein the multispecific antibody is a bispecific antibody that binds to a second epitope that is different from the first epitope.

130. The anti-glyco-MUC1 antibody or antigen-binding fragment of embodiment 129, wherein the bispecific antibody is a CrossMab, a Fab-arm exchange antibody, a bispecific T-cell engager (BiTE), or a dual-affinity retargeting molecule (DART).

131. The anti-glyco-MUC1 antibody or antigen-binding fragment of embodiment 130, wherein the bispecific antibody is a CrossMab.

132. The anti-glyco-MUC1 antibody or antigen-binding fragment of embodiment 131, wherein the bispecific antibody is a CrossMab$^{FAB}$.

133. The anti-glyco-MUC1 antibody or antigen-binding fragment of embodiment 131, wherein the bispecific antibody is a CrossMab$^{VH-VL}$.

134. The anti-glyco-MUC1 antibody or antigen-binding fragment of embodiment 131, wherein the bispecific antibody is a CrossMab$^{CH1-CL}$.

135. The anti-glyco-MUC1 antibody or antigen-binding fragment of embodiment 130, wherein the bispecific antibody is a Fab-arm exchange antibody.

136. The anti-glyco-MUC1 antibody or antigen-binding fragment of embodiment 130, wherein the bispecific antibody is a dual-affinity retargeting molecule (DART).

137. The anti-glyco-MUC1 antibody or antigen-binding fragment of embodiment 130, wherein the bispecific antibody is a bispecific T-cell engager (BiTE).

138. The anti-glyco-MUC1 antibody or antigen-binding fragment of any one of embodiments 129 to 137, wherein the second epitope is a MUC1 epitope.

139. The anti-glyco-MUC1 antibody of antigen-binding fragment of any one of embodiments 129 to 137, wherein the second epitope is a MUC1 epitope that is overexpressed on cancer cells as compared to normal cells.

140. The anti-glyco-MUC1 antibody or antigen-binding fragment of any one of embodiments 129 to 137, wherein the second epitope is a T-cell epitope.

141. The anti-glyco-MUC1 antibody or antigen-binding fragment of embodiment 140, wherein the T-cell epitope comprises a CD3 epitope, a CD8 epitope, a CD16 epitope, a CD25 epitope, a CD28 epitope, or an NKG2D epitope.

142. The anti-glyco-MUC1 antibody or antigen-binding fragment of embodiment 141, wherein the T-cell epitope comprises a CD3 epitope, which is optionally an epitope present in human CD3.

143. The anti-glyco-MUC1 antibody or antigen-binding fragment of embodiment 142, wherein the CD3 epitope comprises a CD3 gamma epitope, a CD3 delta epitope, a CD3 epsilon epitope, or a CD3 zeta epitope.

144. The anti-glyco-MUC1 antibody or antigen-binding fragment of any one of embodiments 1 to 143 which is conjugated to a detectable moiety.

145. The anti-glyco-MUC1 antibody or antigen binding fragment of embodiment 144 in which the detectable moiety is an enzyme, a radioisotope, or a fluorescent label.

146. A fusion protein comprising the amino acid sequence of the anti-glyco-MUC1 antibody or antigen-binding fragment of any of embodiments 1 to 145 operably linked to at least a second amino acid sequence.

147. The fusion protein of embodiment 146, wherein the second amino acid sequence is that of 4-1BB, CD3-zeta, or a fragment thereof.

148. The fusion protein of embodiment 146, wherein the second amino acid sequence is that of a fusion peptide.

149. The fusion protein of embodiment 148, wherein the fusion peptide is a CD28-CD3-zeta or 4-1 BB (CD137)-CD3-zeta fusion peptide.

150. The fusion protein of embodiment 146, wherein the second amino acid sequence is that of a modulator of T cell activation or a fragment thereof.

151. The fusion protein of embodiment 150, wherein the modulator of T cell activation is IL-15 or IL-15Ra.

152. A chimeric antigen receptor (CAR) comprising the scFv of any one of embodiments 125 to 127.

153. The CAR of embodiment 152, comprising in amino- to carboxy-terminal order: a human CD8 leader peptide, the scFv, a human CD8 hinge domain, a human CD8 transmembrane domain, and a CD3-zeta signaling domain.

154. An antibody-drug conjugate comprising the anti-glyco-MUC1 antibody or antigen-binding fragment of any of embodiments 1 to 145 or the fusion protein of any one of embodiments 146 to 151 conjugated to a cytotoxic agent.

155. The antibody-drug conjugate of embodiment 154, wherein the cytotoxic agent is an auristatin, a DNA minor groove binding agent, an alkylating agent, an enediyne, a lexitropsin, a duocarmycin, a taxane, a dolastatin, a maytansinoid, or a vinca alkaloid.

156. The antibody-drug conjugate of embodiment 155, wherein the anti-glyco-MUC1 antibody or antigen-binding fragment or bispecific antibody is conjugated to the cytotoxic agent via a linker.

157. The antibody-drug conjugate of embodiment 156, wherein the linker is cleavable under intracellular conditions.

158. The antibody-drug conjugate of embodiment 157, wherein the cleavable linker is cleavable by an intracellular protease.

159. The antibody-drug conjugate of embodiment 158, wherein the linker comprises a dipeptide.

160. The antibody-drug conjugate of embodiment 159, wherein the dipeptide is val-cit or phe-lys.

161. The antibody-drug conjugate of embodiment 157, wherein the cleavable linker is hydrolyzable at a pH of less than 5.5.

162. The antibody-drug conjugate of embodiment 161, wherein the hydrolyzable linker is a hydrazone linker.

163. The antibody-drug conjugate of embodiment 157, wherein the cleavable linker is a disulfide linker.

164. A nucleic acid comprising a coding region for an anti-glyco-MUC1 antibody or antigen-binding fragment of any of embodiments 1 to 145, the fusion protein of any one of embodiments 146 to 151, or the CAR of embodiment 152 or embodiment 153.

165. The nucleic acid of embodiment 164 in which the coding region is codon-optimized for expression in a human cell.

166. A vector comprising the nucleic acid of embodiment 164 or embodiment 165.

167. The vector of embodiment 166 which is a viral vector.

168. The vector of embodiment 167 wherein the viral vector is a lentiviral vector.

169. A host cell engineered to express the nucleic acid of embodiment 164 or embodiment 165.

170. The host cell of embodiment 169, which is a human T-cell engineered to express the CAR of embodiment 152 or embodiment 153.

171. A host cell comprising the vector of any one of embodiments 166 to 168.

172. The host cell of embodiment 171 which is a T-cell and wherein the vector encodes the CAR of embodiment 152 or embodiment 153.

173. A pharmaceutical composition comprising (a) the anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, or the host cell of embodiment any one of embodiments 169 to 172, and (b) a physiologically suitable buffer, adjuvant or diluent.

174. A method of treating cancer comprising administering to a subject in need thereof an effective amount of the anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173.

175. The method of embodiment 174, wherein the subject is suffering from breast cancer, lung cancer, prostate cancer, pancreatic cancer, esophageal cancer, colorectal cancer, ovarian cancer, uterine cancer, cervical cancer, bladder cancer, brain cancer, non-Hodgkin's lymphoma, cervical cancer, gastric cancer, cholangiocarcinoma, chondrosarcoma, kidney cancer, skin cancer, leukemia, thyroid cancer, or liver cancer.

176. The method of embodiment 175, wherein the subject is suffering from breast cancer.

177. The method of embodiment 175, wherein the subject is suffering from lung cancer.

178. The method of embodiment 177, wherein the lung cancer is non-small cell lung cancer.

179. The method of embodiment 175, wherein the subject is suffering from prostate cancer.

180. The method of embodiment 175, wherein the subject is suffering from pancreatic cancer.

181. The method of embodiment 175, wherein the subject is suffering from esophageal cancer.

182. The method of embodiment 175, wherein the subject is suffering from colorectal cancer.

183. The method of embodiment 175, wherein the subject is suffering from ovarian cancer.

184. The method of embodiment 175, wherein the subject is suffering from uterine cancer.

185. The method of embodiment 175, wherein the subject is suffering from cervical cancer.

186. The method of embodiment 175, wherein the subject is suffering from bladder cancer.

187. The method of embodiment 175, wherein the subject is suffering from brain cancer.

188. The method of embodiment 175, wherein the subject is suffering from non-Hodgkin's lymphoma.

189. The method of embodiment 175, wherein the subject is suffering from cervical cancer.

190. The method of embodiment 175, wherein the subject is suffering from gastric cancer.

191. The method of embodiment 175, wherein the subject is suffering from cholangiocarcinoma.

192. The method of embodiment 175, wherein the subject is suffering from chondrosarcoma.

193. The method of embodiment 175, wherein the subject is suffering from kidney cancer.

194. The method of embodiment 175, wherein the subject is suffering from skin cancer.

195. The method of embodiment 175, wherein the subject is suffering from leukemia.

196. The method of embodiment 175, wherein the subject is suffering from thyroid cancer.

197. The method of embodiment 175, wherein the subject is suffering from liver cancer.

198. A method of detecting cancer in a biological sample, comprising contacting a sample with an anti-glyco-MUC1 antibody or antigen-binding fragment according to any one of embodiments 1 to 145 and detecting binding of the anti-glyco-MUC1 antibody or antigen-binding fragment.

199. The method of embodiment 198, further comprising quantitating the binding of the anti-glyco-MUC1 antibody or antigen-binding fragment.

200. The method of embodiment 198 or embodiment 199, wherein the binding is compared to a normal tissue control as a negative/baseline control and/or to a cancerous tissue control as a positive control.

201. The method of any one of embodiments 198 to 200, wherein the cancer is breast cancer, lung cancer, prostate cancer, pancreatic cancer, esophageal cancer, colorectal cancer, ovarian cancer, uterine cancer, cervical cancer, bladder cancer, brain cancer, non-Hodgkin's lymphoma, cervical cancer, gastric cancer, cholangiocarcinoma, chondrosarcoma, kidney cancer, skin cancer, leukemia, thyroid cancer, or liver cancer.

202. The method of embodiment 201, wherein the cancer is breast cancer.

203. The method of embodiment 201, wherein the cancer is lung cancer.

204. The method of embodiment 203, wherein the lung cancer is non-small cell lung cancer.

205. The method of embodiment 201, wherein the cancer is prostate cancer.

206. The method of embodiment 201, wherein the cancer is pancreatic cancer.

207. The method of embodiment 201, wherein the cancer is esophageal cancer.

208. The method of embodiment 201, wherein the cancer is colorectal cancer.

209. The method of embodiment 201, wherein the cancer is ovarian cancer.

210. The method of embodiment 201, wherein the cancer is uterine cancer.

211. The method of embodiment 201, wherein the cancer is cervical cancer.

212. The method of embodiment 201, wherein the cancer is bladder cancer.

213. The method of embodiment 201, wherein the cancer is brain cancer.

214. The method of embodiment 201, wherein the cancer is non-Hodgkin's lymphoma.

215. The method of embodiment 201, wherein the cancer is cervical cancer.

216. The method of embodiment 201, wherein the cancer is gastric cancer.

217. The method of embodiment 201, wherein the cancer is cholangiocarcinoma.

218. The method of embodiment 201, wherein the cancer is chondrosarcoma.

219. The method of embodiment 201, wherein the cancer is kidney cancer.

220. The method of embodiment 201, wherein the cancer is skin cancer.

221. The method of embodiment 201, wherein the cancer is leukemia.

222. The method of embodiment 201, wherein the cancer is thyroid cancer.

223. The method of embodiment 201, wherein the cancer is liver cancer.

224. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use as a medicament.

225. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of cancer, optionally wherein the cancer is breast cancer, lung cancer, prostate cancer, pancreatic cancer, esophageal cancer, colorectal cancer, ovarian cancer, uterine cancer, cervical cancer, bladder cancer, brain cancer, non-Hodgkin's lymphoma, cervical cancer, gastric cancer, 226. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of breast cancer.

227. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of lung cancer.

228. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of prostate cancer.

229. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of pancreatic cancer.

230. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of esophageal cancer.

231. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of colorectal cancer.

232. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of ovarian cancer.

233. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of uterine cancer.

234. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of cervical cancer.

235. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of bladder cancer.

236. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of brain cancer.

237. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of non-Hodgkin's lymphoma.

238. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of cervical cancer.

239. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of gastric cancer.

240. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of cholangiocarcinoma.

241. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of chondrosarcoma.

242. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of kidney cancer.

243. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of skin cancer.

244. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of leukemia.

245. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of thyroid cancer.

246. The anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for use in the treatment of liver cancer.

247. Use of the anti-glyco-MUC1 antibody or antigen binding fragment of any of embodiments 1 to 145, the fusion protein of any one of embodiments 146 to 151, the CAR of embodiment 152 or embodiment 153, the antibody-drug conjugate of any one of embodiments 154 to 163, the nucleic acid of embodiment 164 or embodiment 165, the vector of any one of embodiments 166 to 168, the host cell of embodiment any one of embodiments 169 to 172, or the pharmaceutical composition of embodiment 173 for the manufacture of a medicament for the treatment of cancer, optionally wherein the cancer is breast cancer, lung cancer, prostate cancer, pancreatic cancer, esophageal cancer, colorectal cancer, ovarian cancer, uterine cancer, cervical cancer, bladder cancer, brain cancer, non-Hodgkin's lymphoma, cervical cancer, gastric cancer, cholangiocarcinoma, chondrosarcoma, kidney cancer, skin cancer, leukemia, thyroid cancer, or liver cancer.

248. The use according to embodiment 247, wherein the cancer is breast cancer

249. The use according to embodiment 247, wherein the cancer is lung cancer.

250. The use according to embodiment 247, wherein the cancer is prostate cancer.

251. The use according to embodiment 247, wherein the cancer is pancreatic cancer.

252. The use according to embodiment 247, wherein the cancer is esophageal cancer.

253. The use according to embodiment 247, wherein the cancer is colorectal cancer.

254. The use according to embodiment 247, wherein the cancer is ovarian cancer.

255. The use according to embodiment 247, wherein the cancer is uterine cancer.

256. The use according to embodiment 247, wherein the cancer is cervical cancer.

257. The use according to embodiment 247, wherein the cancer is bladder cancer.

258. The use according to embodiment 247, wherein the cancer is brain cancer.

259. The use according to embodiment 247, wherein the cancer is non-Hodgkin's lymphoma.

260. The use according to embodiment 247, wherein the cancer is cervical cancer.

261. The use according to embodiment 247, wherein the cancer is gastric cancer.

262. The use according to embodiment 247, wherein the cancer is cholangiocarcinoma.

263. The use according to embodiment 247, wherein the cancer is chondrosarcoma.

264. The use according to embodiment 247, wherein the cancer is kidney cancer.

265. The use according to embodiment 247, wherein the cancer is skin cancer.

266. The use according to embodiment 247, wherein the cancer is leukemia.

267. The use according to embodiment 247, wherein the cancer is thyroid cancer.

268. The use according to embodiment 247, wherein the cancer is liver cancer.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

The invention claimed is:

1. An anti-glyco-MUC1 antibody or antigen binding fragment comprising a complementarity determining region (CDR) H1 comprising the amino acid sequence of SEQ ID NO:93, a CDR-H2 comprising the amino acid sequence of SEQ ID NO:94, a CDR-H3 comprising the amino acid sequence of SEQ ID NO:95, a CDR-L1 comprising the amino acid sequence of SEQ ID NO:96, a CDR-L2 comprising the amino acid sequence of SEQ ID NO:97, and a CDR-L3 comprising the amino acid sequence of SEQ ID NO:98.

2. The anti-glyco-MUC1 antibody or antigen-binding fragment of claim 1, which has:
   (a) a VH comprising complementarity determining regions (CDRs) of SEQ ID NOS:3-5 and a VL comprising CDRs of SEQ ID NOS:6-8;
   (b) a VH comprising complementarity determining regions (CDRs) of SEQ ID NOS:9-11 and a VL comprising CDRs of SEQ ID NOS:12-14;
   (c) a VH comprising complementarity determining regions (CDRs) of SEQ ID NOS:15-17 and a VL comprising CDRs of SEQ ID NOS:18-20;
   (d) a VH comprising complementarity determining regions (CDRs) of SEQ ID NOS:25-27 and a VL comprising CDRs of SEQ ID NOS:28-30;
   (e) a VH comprising complementarity determining regions (CDRs) of SEQ ID NOS:31-33 and a VL comprising CDRs of SEQ ID NOS:34-36;
   (f) a VH comprising complementarity determining regions (CDRs) of SEQ ID NOS:37-39 and a VL comprising CDRs of SEQ ID NOS:40-42;
   (g) a VH comprising complementarity determining regions (CDRs) of SEQ ID NOS:45-47 and a VL comprising CDRs of SEQ ID NOS:48-50;
   (h) a VH comprising complementarity determining regions (CDRs) of SEQ ID NOS:51-53 and a VL comprising CDRs of SEQ ID NOS:54-56;
   (i) a VH comprising complementarity determining regions (CDRs) of SEQ ID NOS:57-59 and a VL comprising CDRs of SEQ ID NOS:60-62;
   (j) a VH comprising complementarity determining regions (CDRs) of SEQ ID NOS:63-65 and a VL comprising CDRs of SEQ ID NOS:66-68;
   (k) a VH comprising complementarity determining regions (CDRs) of SEQ ID NOS:69-71 and a VL comprising CDRs of SEQ ID NOS:72-74;
   (l) a VH comprising complementarity determining regions (CDRs) of SEQ ID NOS:75-77 and a VL comprising CDRs of SEQ ID NOS:78-80;
   (m) a VH comprising complementarity determining regions (CDRs) of SEQ ID NOS:81-83 and a VL comprising CDRs of SEQ ID NOS:84-86; or
   (n) a VH comprising complementarity determining regions (CDRs) of SEQ ID NOS:87-89 and a VL comprising CDRs of SEQ ID NOS:90-92.

3. The anti-glyco-MUC1 antibody or antigen-binding fragment of claim 1, which has
   a VH comprising an amino acid sequence having at least 95% sequence identity to SEQ ID NO:1 and a VL comprising an amino acid sequence having at least 95% sequence identity to SEQ ID NO:2.

4. The anti-glyco-MUC1 antibody or antigen-binding fragment of claim 1, which has a VH comprising the amino acid sequence of SEQ ID NO:1 and a VL comprising the amino acid sequence of SEQ ID NO:2.

5. The anti-glyco-MUC1 antibody or antigen-binding fragment of claim 1, which has
   a VH comprising an amino acid sequence having at least 95% sequence identity to SEQ ID NO:23 and a VL comprising an amino acid sequence having at least 95% sequence identity to SEQ ID NO:24.

6. The anti-glyco-MUC1 antibody or antigen-binding fragment of claim 1, which has a VH comprising the amino acid sequence of SEQ ID NO:23 and a VL comprising the amino acid sequence of SEQ ID NO:24.

7. The anti-glyco-MUC1 antibody or antigen-binding fragment of claim 1, which is multivalent.

8. The anti-glyco-MUC1 antibody or antigen-binding fragment of claim 1, which is in the form of a single-chain variable fragment (scFv).

9. A chimeric antigen receptor (CAR) comprising the scFv of claim 8.

10. The anti-glyco-MUC1 antibody or antigen-binding fragment of claim 1, which is in the form of a multispecific antibody.

11. The anti-glyco-MUC1 antibody or antigen-binding fragment of claim 10, wherein the multispecific antibody is a bispecific antibody that binds to a first epitope and a second epitope that is different from the first epitope.

12. The anti-glyco-MUC1 antibody or antigen-binding fragment of claim 11, wherein the bispecific antibody is a CrossMab, a Fab-arm exchange antibody, a bispecific T-cell engager (BiTE), or a dual-affinity retargeting molecule (DART).

13. The anti-glyco-MUC1 antibody or antigen-binding fragment of claim 11, wherein the second epitope is a T-cell epitope.

14. The anti-glyco-MUC1 antibody or antigen-binding fragment of claim 13, wherein the T-cell epitope comprises a CD3 epitope, a CD8 epitope, a CD16 epitope, a CD25 epitope, a CD28 epitope, or an NKG2D epitope.

15. A fusion protein comprising the amino acid sequence of the anti-glyco-MUC1 antibody or antigen-binding fragment of claim 1 operably linked to at least a second amino acid sequence.

16. An antibody-drug conjugate comprising the anti-glyco-MUC1 antibody or antigen-binding fragment of claim 1 conjugated to a cytotoxic agent.

17. A nucleic acid comprising a coding region for an anti-glyco-MUC1 antibody or antigen-binding fragment of claim 1.

18. A vector comprising the nucleic acid of claim 17.

19. A host cell comprising the vector of claim 18.

20. A host cell engineered to express the nucleic acid of claim 17.

21. A pharmaceutical composition comprising (a) the anti-glyco-MUC1 antibody or antigen binding fragment of claim 1 and (b) a physiologically suitable buffer, adjuvant or diluent.

22. A method of treating cancer comprising administering to a subject in need thereof an effective amount of the anti-glyco-MUC1 antibody or antigen binding fragment of claim 1.

* * * * *